(12) United States Patent
Grandi

(10) Patent No.: US 12,054,521 B2
(45) Date of Patent: Aug. 6, 2024

(54) FhuD2 FUSION PROTEINS FOR THE OUTER MEMBRANE VESICLE (OMV) DELIVERY OF HETEROLOGOUS POLYPETIDES AND IMMUNOGENIC COMPOSITIONS THEREOF

(71) Applicant: BIOMVIS SRL, Siena (IT)

(72) Inventor: Alberto Grandi, Siena (IT)

(73) Assignee: BIOMVIS SRL, Siena (IT)

( * ) Notice: Subject to any disclaimer, the term of this patent is extended or adjusted under 35 U.S.C. 154(b) by 1000 days.

(21) Appl. No.: 16/978,807

(22) PCT Filed: Mar. 7, 2019

(86) PCT No.: PCT/EP2019/055787
§ 371 (c)(1),
(2) Date: Sep. 8, 2020

(87) PCT Pub. No.: WO2019/170837
PCT Pub. Date: Sep. 12, 2019

(65) Prior Publication Data
US 2020/0405835 A1    Dec. 31, 2020

(30) Foreign Application Priority Data

Mar. 9, 2018 (EP) .................................... 18160991

(51) Int. Cl.
| | |
|---|---|
| *C07K 14/31* | (2006.01) |
| *A61K 38/16* | (2006.01) |
| *A61K 39/00* | (2006.01) |
| *A61P 35/00* | (2006.01) |
| *A61P 37/04* | (2006.01) |
| *C07K 14/195* | (2006.01) |
| *C07K 14/47* | (2006.01) |
| *C07K 14/71* | (2006.01) |
| *C12N 15/62* | (2006.01) |
| *C07K 14/705* | (2006.01) |

(52) U.S. Cl.
CPC ............ *C07K 14/31* (2013.01); *A61K 38/164* (2013.01); *A61K 39/0011* (2013.01); *A61K 39/001104* (2018.08); *A61K 39/001166* (2018.08); *A61P 35/00* (2018.01); *A61P 37/04* (2018.01); *C07K 14/195* (2013.01); *C07K 14/4748* (2013.01); *C07K 14/71* (2013.01); *C12N 15/62* (2013.01); *A61K 2039/55555* (2013.01); *A61K 2039/6068* (2013.01); *C07K 14/705* (2013.01); *C07K 2319/03* (2013.01); *C07K 2319/035* (2013.01)

(58) Field of Classification Search
CPC .. C07K 14/195; C07K 14/31; C07K 14/4748; C07K 2319/035; A61K 38/164; A61K 39/0011; A61K 2039/55555
See application file for complete search history.

(56) References Cited

U.S. PATENT DOCUMENTS

2018/0207255 A1 * 7/2018 Grandi .................... C07K 14/31

FOREIGN PATENT DOCUMENTS

| WO | WO-2015144691 A1 * | 10/2015 | ............. A61K 35/74 |
| WO | 2016184860 A1 | 11/2016 | |

OTHER PUBLICATIONS

Gerritzen M.J.H. et al., "Bioengineering bacterial outer membrane vesicles as vaccine platform", Biotechnology Advances, vol. 35, No. 5, May 15, 2017, pp. 565-574.
Grandi A. et al., "Synergistic protective activity of tumor-specific epitopes engineered in bacterial outer membrane vesicles", Frontier in Oncology, Frontiers Research Foundation, CH, Vo. 7, No. NOV Nov. 7, 2017, pp. 1-12.
Podkowa K., et al., "Crystal and solution structure analysis of FhuD2 from *Staphylococcus aureus* in multiple unlinganded conformations and bound to ferrioxamine-B", Biochemistry, vol. 53, No. 12, Apr. 2014, pp. 2017-2031.
Search Report and Written Opinion of PCT/EP2019/055787 of Apr. 17, 2019.

* cited by examiner

*Primary Examiner* — Zachary C Howard
(74) *Attorney, Agent, or Firm* — Silvia Salvadori, P.C.; Silvia Salvadori

(57) ABSTRACT

There are disclosed fusion proteins comprising the bacterial protein FhuD2 and one or more copies of a heterologous polypeptide, polynucleotides and expression vectors encoding the fusion proteins and bacterial outer membrane vesicles containing them. Other aspects of the invention regard immunogenic compositions comprising the outer membrane vesicles and their use in the prevention or treatment of tumors.

12 Claims, 30 Drawing Sheets
Specification includes a Sequence Listing.

LS: Secretion leader sequence
LP: lipobox

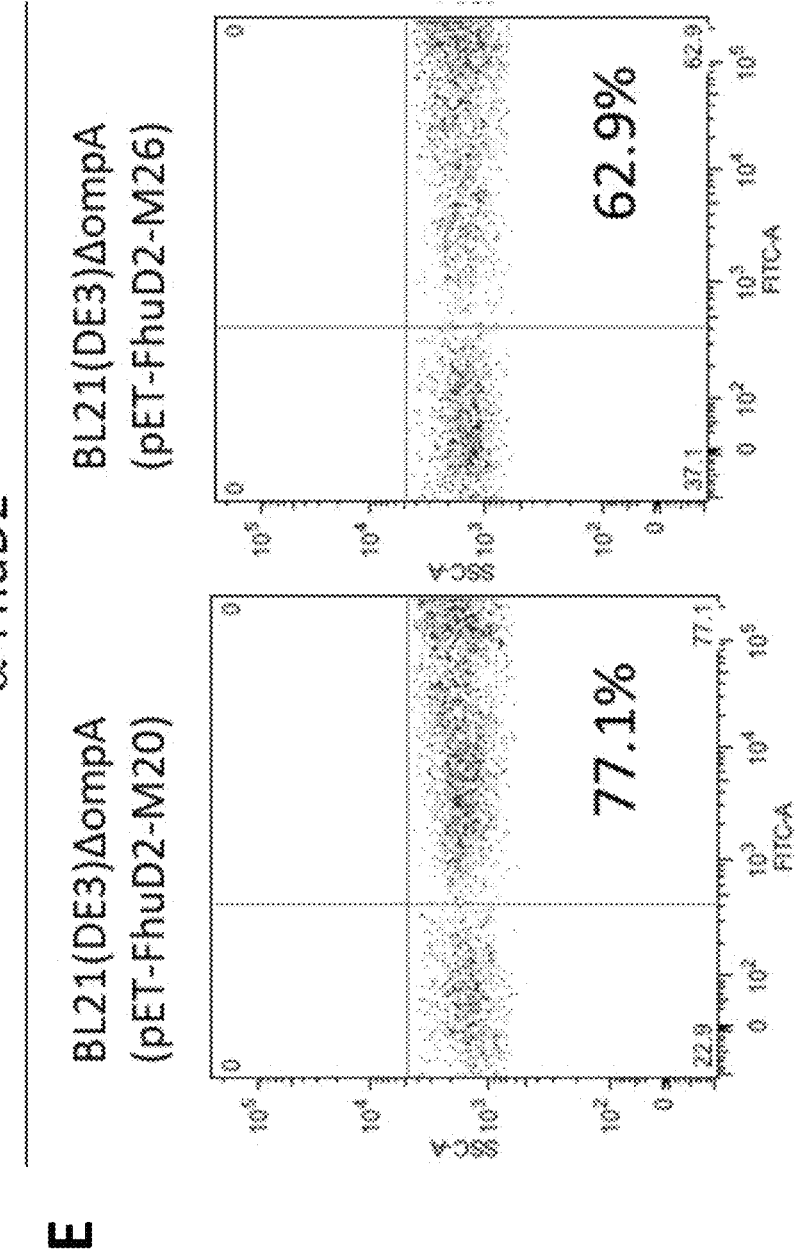

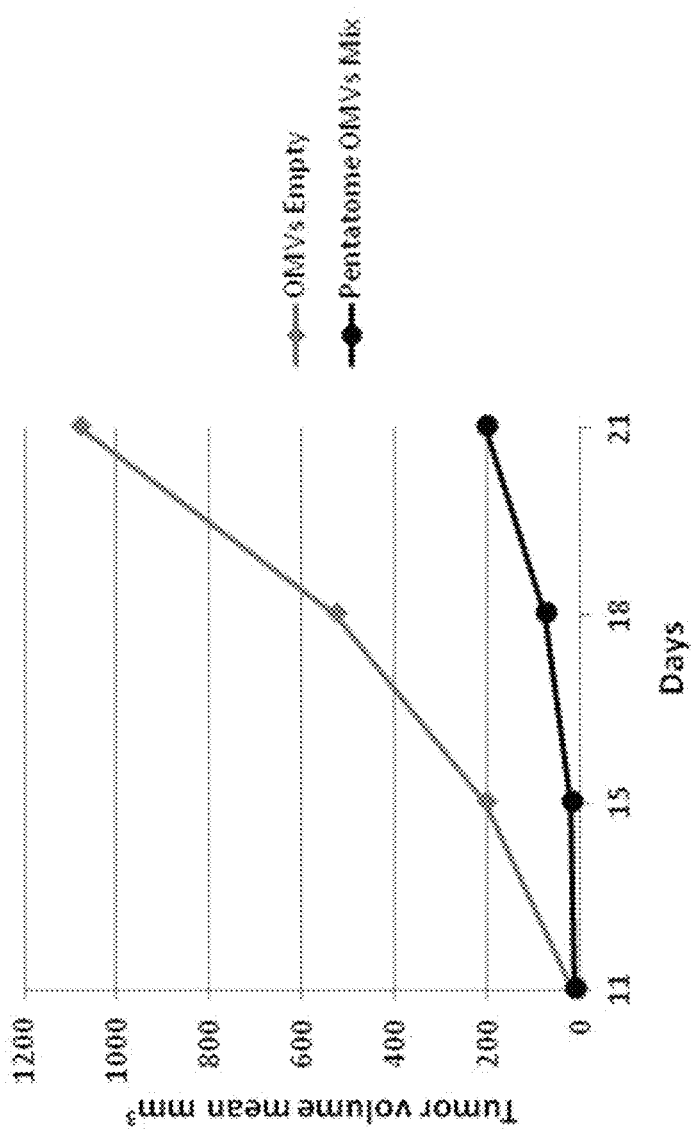

FhuD2 FUSION PROTEINS FOR THE OUTER MEMBRANE VESICLE (OMV) DELIVERY OF HETEROLOGOUS POLYPETIDES AND IMMUNOGENIC COMPOSITIONS THEREOF

This application is a U.S. national stage of PCT/EP2019/055787 filed on 7 Mar. 2019, which claims priority to and the benefit of European Application No. 18160991.8 filed on 9 Mar. 2018, the contents of which are incorporated herein by reference in their entireties.

This invention relates to the delivery of heterologous polypeptides to the surface of bacteria and outer membrane vesicles (OMVs). Heterologous polypeptides are chaperoned to the surface as fusions to lipidated FhuD2. Accordingly, the invention provides fusion proteins comprising the bacterial protein FhuD2 and one or more copies of a heterologous polypeptide fused thereto, and bacterial outer membrane vesicles containing them. Vesicles carrying fused polypeptides are particularly useful in the preparation of immunogenic compositions for the prevention or treatment of tumors.

BACKGROUND ART

Bacterial Protein Secretion and Lipoproteins

In cells from both prokaryotes and eukaryotes more than one third of the proteome is secreted across, or inserted into, biological membranes. Secretory proteins exert a plethora of functions that are essential for life.

Evolution has produced a remarkable array of mechanisms to export proteins. Of these the Sec pathway is ubiquitous and essential for viability in all living organisms. In bacteria, export by the Sec pathway relies on a hydrophobic signal sequence at the N-terminus of the secreted proteins, known as leader sequence of signal sequence (LP), which is typically 20 amino acids in length and contains 3 regions: a positively charged amino terminal (1-3 residues), a hydrophobic core, consisting of a stretch of 14-20 neutral, primarily hydrophobic amino acids, and a polar carboxyl-terminal. (Papanikou et al. (2007) Nature Reviews Microbiology, 5, 839-851). Soon after the LP emerges from the translation machinery, it is recognized by the SecB protein which brings the newly synthesized secretory protein (usually not fully translated yet and unfolded) to the membrane associated SecYEG transport machinery, that allows protein translocation using an ATP-dependent process. Finally, secretory proteins are released from the membrane through the action of a leader peptidase that cleaves and removes the LP.

One specific family of bacterial secretory proteins are lipoproteins. Bacterial lipoproteins are a class of peripherally anchored membrane proteins, which play key roles in basic bacterial physiology as well as in pathogenic mechanisms such as adhesion, colonization, invasion and immune evasion.

While in Gram-positive bacteria lipoproteins cross the membrane and remain attached on its external side through their lipid chains, in Gram-negative bacteria they can be found in three different cellular compartments: 1) attached to the periplasmic side of the inner membrane, 2) attached to the periplasmic side of the outer membrane, and 3) exposed on the surface of the outer membrane (OM).

Lipoproteins are synthesized in the bacterial cytosol as precursors (pre-prolipoproteins) carrying a LP very similar to all SecB-dependent LPs but with the unique property to have the specific conserved sequence Leu-(Ala/Ser)-(Gly-Ala)-Cys at its C-terminal region, known as "lipobox" (Kovacs-Simon, A., et al. 2011; Hutchings, M. I., et al., 2009). Once crossed the inner membrane, pre-prolipoproteins are first modified by a diacylglyceryl transferase (Lgt), which transfers a diacylglyceride to the cysteine sulfhydryl of the lipobox, forming a prolipoprotein. Subsequently, a specific signal peptidase (Lsp) cleaves the amide bond preceding the cysteine residue and the resulting diacylated apolipoprotein remains anchored to the membrane via the acyl moieties. Finally, an N-acyltransferase (Lnt) attaches a third acyl group to the free amino group of the N-terminal cysteine, creating a mature tri-acylated lipoprotein. Once tri-acylated, lipoproteins are ready to be translocated to the inner leaflet of the outer membrane. The transport is mediated by the Lol system, consisting of a transmembrane protein complex (LolCDE), an ATP-binding cassette (ABC) transporter, a periplasmic chaperone (LolA) and an outer-membrane receptor (LolB) (Tokuda, H., et al. 2009). All lipoproteins undergo the Lol-dependent translocation unless the lipidated cysteine is followed by specific amino acids (Tokuda, H. and S. Matsuyama, 2004; Bos, M. P., et al. 2007). In particular, the presence at position+2 of an aspartic acid has been shown to be sufficient to prevent most of lipoproteins from being transported to the outer membrane. While the final destination of many lipoproteins is the inner leaflet of the outer membrane, a group of lipoproteins reaches the bacterial surface. For instance, some lipoproteins are transported through the OM using the Type II Secretion System (T2SS) (for instance, the *K. oxytoca* PulA [d'Enfert, C., A. Ryter, and A. P. Pugsley (1987) EMBO J, 1987, 6, 3531]) and the Type V Secretion System (T5SS) (for instance, the *N. meningtidis* NalP [van Ulsen, P., et al., (2003) Mol Microbiol, 50, 1017; Oomen, C. J., et al., (2004) EMBO J, 23, 1257]). Other lipoproteins can reach the surface using the Bam complex (Konovalova, A., et al., (2014) Proc Natl Acad Sci USA, 111, 4350). A third group of lipoproteins cross the outer membrane using lipoprotein-specific flippases (Schulze, R. J., et al. (2010), Mol Microbiol, 76, 1266; Hooda, Y., et al. (2016) Nature Microbiology, 1, 16009). Finally, a last group of lipoproteins, here referred to as "promiscuous lipoproteins", are transported all the way to the bacterial surface using a transport process eventually conserved among some Gram-negative species. Promiscuous lipoproteins appear to be very rare, as indicated by the fact that the publications reporting them are limited to few examples. They include *Salmonella* YaiW and *Vibrio cholerae* VolA that were reported to maintain their surface location when transplanted from their natural host to *E. coli* (Arnold, M. F., et al., *J Bacteriol*, 2014, 196:436-444; Pride, A. C., et al., *MBio,* 2013, 4: e00305-13).

Whatever mechanism lipoproteins use to reach external side of the outer membrane; surface-exposed lipoproteins can theoretically be used to chaperone heterologous polypeptides to the surface of Gram-negative bacteria. For instance, it was recently demonstrated that two promiscuous lipoproteins from *Neisseria meningitidis* (Nm-fHbp and NHBA) and one from *Aggregatibacter actinomycetemcomitans* (Aa-fHbp) can expose proteins/protein domains on the *E. coli* surface (Fantappie' L. et al., *Mol Cell Proteomics,* 2017, 16:1348-1364). However, the efficiency with which lipoprotein fusions accumulate in the outer membrane and expose the heterologous polypeptides to bacterial surface can vary quite substantially, depending upon the nature of both the carrier lipoprotein and the passenger polypeptide. Therefore, the discovery of novel carrier lipoproteins has important biotechnological applications since such carriers could be exploited as chaperons to deliver foreign proteins and polypeptides to the surface of bacteria and bacterial Outer Membrane Vesicles. The biotechnological applications include enzymatic reactions, selective capturing of molecules, efficient elicitation of immune responses.

Bacterial Outer Membrane Vesicles (OMVs)

All Gram-negative bacteria spontaneously release outer membrane vesicles (OMVs) during growth both in vitro and in vivo. OMVs are closed spheroid particles, 20-300 nm in diameter, generated through a "budding out" of the bacterial outer membrane. Consistent with that, the majority of OMV components are represented by LPS, glycerophospho lipids, outer membrane proteins, lipoproteins and periplasmic proteins (A. Kulp and Kuehn M. J. (2010) *Annu. Rev. Microbiol.* 64, 163-184; T. N. Ellis and Kuehn M. J. (2010) *Microbiol. Mol. Biol. Rev.* 74, 81-94).

OMVs represent a distinct secretory pathway with a multitude of functions, including inter and intra species cell-to-cell cross-talk, biofilm formation, genetic transformation, defense against host immune responses and toxin and virulence factor delivery to host cells (A. Kulp and Kuehn M. J. (2010) *Annu. Rev. Microbiol.* 64, 163-184). OMVs interaction to host cells can occur by endocytosis after binding to host cell receptors or lipid rafts. Alternatively, OMVs have been reported to fuse to host cell membrane, leading to the direct release of their content into the cytoplasm of the host cells (A. Kulp and Kuehn M. J. (2010) *Annu. Rev. Microbiol.* 64, 163-184; T. N. Ellis and Kuehen M. J. (2010) *Micrbiol. Mol. Biol. Rev.* 74, 81-94).

OMVs purified from several pathogens, including *Neisseria, Salmonella, Pseudomonas, Vibrio cholerae Burkholderia,* and *E. coli*, induce potent protective immune responses against the pathogens they derive from (B. S. Collins (2011) *Discovery Medicine,* 12 7-15), and highly efficacious anti-*Neisseria* OMV-based vaccines are already available for human use (J. Holst et al. (2009) *Vaccine,* 27S, B3-B12). Such remarkable protection is attributed to two main properties of OMVs. First, they carry the proper immunogenic and protective antigens which, in extracellular pathogens, usually reside on the surface and therefore are naturally incorporated in OMVs. Indeed, OMV immunization induces potent antibody responses against the major membrane-associated antigens. However, OMV immunogenicity is not restricted to antibody responses. For instance, mice immunized with *Salmonella* OMVs develop robust *Salmonella*-specific B and T cell responses, and OMVs stimulate IFN-γ production by a large proportion of CD4+ T cells from mice previously infected with *Salmonella*, indicating that OMVs are an abundant source of antigens recognized by *Salmonella*-specific CD4+ T cells (R. C. Alaniz et al., (2007) *J. Immunol.* 179, 7692-7701). Second, OMVs possess a strong "built-in" adjuvanticity since they carry many of the bacterial Pathogen-Associated-Molecular Patterns (PAMPs) which, by binding to pathogen recognition receptors (PRRs), play a key role in stimulating innate immunity and in promoting adaptive immune responses. OMV-associated PAMPs include LPS which, in concert with MD-2 and CD14, binds TLR-4, lipoproteins whose acylpeptide derivatives interact with TLR-1/2 and 2/6 heterodimers, and peptidoglycan whose degradation products bind to intracellular NODI/2 (A. Moshiri et al., *Hum. Vaccines. Immunother.* (2012) 8, 953-955; T. N. Ellis et al., (2010) *Inn. Immun.* 78, 3822-3831; M. Kaparakis et al., (2010) *Cell. Miocrobiol.* 12, 372-385). The engagement of this group of PPRs results in the activation of transcription factors (NF-kB) and the consequent expression of specific cytokines. Interestingly, LPS, lipoproteins and peptidoglycan can work synergistically, thus potentiating the built-in adjuvanticity of OMVs (D. J. Chen et al., (2010) *PNAS,* 107, 3099-3104).

OMVs also have the capacity to induce protection at the mucosal level. Protection at the mucosal sites is known to be at least partially mediated by the presence of pathogen-specific IgAs and Th17 cells. In particular, a growing body of evidence suggests that Th17 cells have evolved to mediate protective immunity against a variety of pathogens at different mucosal sites. Interestingly, Th17 cells have recently also been shown to play a crucial role in the generation of vaccine-induced protective responses. For instance, it has been reported that in mice whole cell pertussis vaccines (Pw) induce Th17 cells and neutralization of IL-17 after vaccination reduces protection against a pulmonary challenge with *B. pertussis*. Similarly, in a CD4+ T cell dependent, antibody-independent model of vaccine-induced protection following *S. pneumoniae* challenge, treatment with anti-IL-17 antibodies resulted in reduced immunity to pneumococcal colonization compared to the control serum treated mice (Malley R, et al. (2006) *Infect Immun.,* 74:2187-95). Elicitation of IgAs and Th17 cells by OMVs has been well documented and this can explain mechanistically the good protective activities of OMVs against several mucosal pathogens. For instance, immunization with *Vibrio cholerae*-derived OMVs protects rabbits against *Vibrio cholerae* oral challenge (Roy N. et al. (2010) *Immunol. Clinical Microbiol.* 60, 18-27) and *Pasteurella multocida*-derived and *Mannheimia haemolytica*-derived OMVs protect mice from oral challenge with *P. multocida* (Roier S. et al., (2013) *Int. J. Med. Microbiol.* 303, 247-256). In addition, intranasal immunization with *Porphyromonas gingivalis* OMVs elicits potent IgA production at both serum and mucosal level and immunization with *Escherichia coli*-derived OMVs prevent bacteria-induced lethality. Protective effect of *Escherichia coli*-derived OMVs is primarily mediated by OMV-specific, IFN-γ and IL-17 producing, T cells (Kim O Y et al., (2013) *J. Immunol.* 190, 4092-4102).

In addition to their "built-in" adjuvanticity, OMVs are becoming a promising vaccine platform for two main reasons.

1. OMVs are amenable for large scale production—In general, the amount of OMVs released by Gram-negative bacteria when grown under laboratory conditions is too low to allow their exploitation in biotechnological applications. However, two approaches can be used to enhance the yields of OMVs and make them compatible with industrial applications. The first one exploits the addition of mild detergents to the bacterial biomass to promote the vesiculation process and, at the same time, to decrease the level of OMV reactogenicity by removing a substantial amount of LPS (Fredriksen J. H. et al, (1991) NIPH Ann. 14, 67-79). Although this process has been proved to produce safe and effective vaccines against Meningococcal B (Granoff D. (2010), *Clin. Infect. Dis.* 50, S54-S65; Crum-Cianflone N, Sullivan E. (2016) Meningococcal vaccinations. *Infect Dis Ther.,* 5, 89-112) its main drawback is that the detergent treatment favors bacterial cell lysis with the consequence that the OMV preparations are heavily contaminated with cytoplasmic proteins (Ferrari et al., (2006) Proteomics, 6, 1856-1866). The second approach to enhance OMV production is to insert into the genome of the OMV-producing strain mutations that enhance vesiculation. For instance, in *Neisseria meningitidis*, a mutation in the gna33 gene, encoding a glucosyltransferase, has been shown to drive the release of several milligrams of vesicles per liter in the culture supernatant (Ferrari et al., (2006) Proteomics, 6, 1856-1866). Similar quantities of vesicles are obtained from *Escherichia coli* strains carrying deletions in the genes encoding the Tol/Pal system (a protein complex involved in the connection of the inner membrane with the outer membrane) (Bernadac A. et al., (1998) *J. Bacteriol.* 180, 4872-4878) and in the ompA gene, encoding one of the major outer membrane proteins of *E. coli* (Fantappiè et al., (2014) *Journal of Extracellular Vesicles*, 3, 24015). Such quantities make the production process of OMVs highly efficient and inexpensive. A number of other mutations have been described that enhance the production of OMVs in several Gram negative bacteria, including *Salmonella* and *E. coli* (Deatherage B. L. et al. (2009) *Mol. Microbiol.* 72, 1395-1407; McBroom A. J. and Kuehen M. J. (2007) *Mol. Microbiol.* 63, 545-558; Kulp et al., (2015) *PLos ONE* 10, e0139200).

As far as the purification of OMVs from the culture supernatant is concerned, centrifugation and tangential flow filtration (TFF) are commonly used. The yield of OMV production using centrifugation couple to TFF can easily exceed 100 mg/liter of culture (Berlanda Scorza F. et al., (2012) *Plos One* 7, e35616) and therefore the process is perfectly compatible with large scale production.

2. OMVs can be manipulated in their protein content by genetic engineering. This feature was demonstrated for the first time by Kesty and Kuehn who showed that *Yersinia enterocolitica* outer membrane protein Ail assembled on OMVs surface when expressed in *E. coli*, and that the GFP fluorescence protein fused to the "twin arginine transport (Tat)" signal sequence was incorporated in the OMV lumen (N. C. Kesty and Kuhen M. J. (2004) *J. Biol. Chem.* 279, 2069-2076). Following the observation by Kesty and Kuehn, an increasing number of heterologous proteins have been successfully delivered to OMVs using a variety of strategies. For instance, heterologous antigens have been delivered to the surface of OMVs by fusing them to the β-barrel forming autotransporter AIDA and to hemolysin ClyA, two proteins that naturally compartmentalized into *E. coli* OMVs (J. Schroeder and Aebischer T. (2009) *Vaccine*, 27, 6748-6754; D. J. Chen et al., (2010) *PNAS*, 107, 3099-3104). Recently, heterologous antigens from Group A *Streptococcus* and Group B *Streptococcus* were delivered to the lumen of *E. coli* vesicles by fusing their coding sequences to the leader peptide of *E. coli* OmpA. Interestingly, when the recombinant vesicles were used to immunize mice, they elicited high titers of functional antibodies against the heterologous antigens, despite their luminal location (Fantappiè et al., (2014) *Journal of Extracellular Vesicles*, 3, 24015).

Many strategies have been successfully used to deliver heterologous antigens to the vesicle compartment. However, a universal system working for any protein antigen has not been described yet. A strategy that is effective for one specific antigen in terms of level of expression and elicitation of immune responses can be inefficient with other antigens.

Therefore, the identification of novel strategies to deliver antigens to the OMV compartment is highly needed.

Cancer Vaccines

The notion that the immune system can recognize and mount a response against tumors was postulated in the late nineteenth century by Coley who demonstrated that attenuated bacteria or bacterial products injected into tumor-bearing patients in some cases resulted in tumor regression (Coley W B (1893) Am. J. Med. Sci. 105: 487-511). Nearly a century later, it was demonstrated that immunization of mice with mutated tumor cells could induce a protective anti-tumor immune response against non-immunogenic tumor (Van and Boon, (1982) PNAS, 79, 4718-4722). Together, these studies set a foundation for cancer immunotherapy research and demonstrated the therapeutic potential of strategies targeting immune modulation for tumor eradication and protection against tumor recurrences. Therefore, the development of cancer vaccines capable of generating an active tumor-specific immune response serves as a promising venue for cancer therapy.

Probably the best example that illustrates the potential of the immune system to fight cancer is given by Sipuleucel-T, the recently approved vaccine for prostate cancer patients. The vaccine is produced by isolating an individual patient's CD54+ white cells via leukapheresis, exposing the isolated cells ex vivo to PA2024, a protein antigen expressed in over 95% of prostate cancers, and infusing the vaccine back into the patient. Sipuleucel-T therefore consists of personalized primed APCs and of a mixed cell suspension containing also monocytes, macrophages, B and T cells, exposed to activated APCs (Lu C. et al. (2011) Exp. Opin. Biol. Ther. 11, 99-108). Although complicated and expensive to produce the vaccine clearly indicates that, if properly stimulated, the immune system can control tumor growth and progression.

Other promising cell-based vaccines are being developed by collecting Tumor Infiltrating Lymphocytes (TILs) from freshly dissected tumors, expanding them upon stimulation with tumor antigens (total tumor extracts or selected tumor antigens) and infusing TILs back into the patients (Restifo et al., (2012) Nature Rev. Immunol. 12, 269-281). Also this approach has shown to reduce tumor growth and to prolong overall survival.

A more practical way to develop cancer vaccines is to stimulate patient's immune system by injecting into patients specific cancer antigens formulated with proper adjuvants/immune potentiators (Berinstein N L (2007) Vaccine 25S, B72-B88). This approach has the great advantage to avoid the complication of collecting immune cells from each patient and of re-injecting them back after activation and/or amplification.

Several trials are ongoing exploiting this strategy. Among the most promising ones are two peptide-based vaccines, Her2-E75 (Nelipepimut-S) (Mittendorff E A et al., (2014) Annals of Oncology 25: 1735-1742) and EGFRvIII (Rindopepimut) (Del Vecchio C A et al. (2012), Expert Rev. Vaccines 11, 133-144) against Her2-positive breast cancer and glioblastoma, respectively. These vaccines, which are formulated with the immune stimulator GM-CSF, appear to have different mechanisms of action. The first primarily induces cytotoxic CD8+ T cells while the other mostly elicits humoral response.

However, despite demonstrated efficacy in various murine models, till recently cancer vaccines have found little success in the clinic. Although several factors may contribute to the failure of therapeutic cancer vaccines in the clinic, the most important ones are i) the weak immunogenicity of Tumor Associated Antigens (TAAs), ii) central and peripheral immune tolerance to self TAAs, and iii) various immune evasion mechanisms employed by the progressing tumor.

Therefore, the success of therapeutic cancer vaccines may require formulations that induce potent immune responses that overcome immune tolerance to TAAs as well as reverse or inhibit tumor-mediated immune evasion mechanisms.

Enthusiasm for therapeutic cancer vaccines has been recently rejuvenated by two major discoveries. First, it has been shown that the large number of mutations occurring in most tumors (Vogelstein, B. et al., (2013) *Science*, 339, 1546-1558) creates "neo-epitopes", which can become the targets of both CD4+ and CD8+ T cells. Neo-epitope-specific T cells have been found among tumor infiltrating lymphocytes (TILs) and when amplified ex vivo from tumor biopsies and introduced back into patients, TILs can exert anti-tumor activities (Rosenberg S. A. and Restifo N. P. (2015) *Science*, 348, 62-68). Moreover, the impressive therapeutic effect of checkpoint inhibitor antibodies observed in a fraction of patients has been shown to correlate with the number of tumor-associated mutations (Rizvi N A et al., (2015) *Science* 348, 124-128; Snyder A. et al., (2014) *N. Engl. J. Med.* 371, 2189-2199; Van Allen E M et al., (2014) *Science* 350, 207-211). Consequently, vaccines formulated with neo-epitopes have recently been created and shown to be highly effective in preventing tumor growth in different preclinical settings (Kreiter S et al., (2015) *Nature*, 520, 692-6962). Second, Kranz and co-workers (Kranz L M. Et al., (2016) *Nature*, 534, 396-401) have demonstrated that when administered intra venous (i.v.) in melanoma patients, negatively charged liposomes carrying TAA-encoding synthetic RNAs were efficiently taken up by splenic DCs, resulting in a potent elicitation of TAA-specific CD4+ and CD8+ T cells. Overall, these data support the hypothesis that personalized cancer vaccines based on patient-specific, mutation-derived neoepitopes can drive protective anti-tumor immune responses when formulated with the appropriate combination of adjuvant(s) and delivery system.

The strategy to develop neoepitope-based cancer vaccines envisages: 1) tumor resection and whole genome/transcriptome sequencing, 2) bioinformatics identification of tumor-specific mutations, 3) bioinformatics prediction of T cell neoepitopes generated by the tumor-specific mutations, 4) in silico and/or experimental selection of the most immunogenic neoepitopes, 5) preparation of the patient-specific, neoepitope-based vaccine 6) vaccination of the patient from which the tumor has been removed and sequenced.

The first-in-human testing of such an approach has been conducted by Sahin and coworkers (Nature (2017) 547, 222) in 13 stage III/IV melanoma patients. Ten mutation-derived CD4+ T cells epitopes per patient were selected and all patients received a treatment with a maximum of 20 doses of RNA-based neo-epitope vaccine. Comparison of documented cancer recurrences in treated patients before and after neo-epitope vaccination showed a significant reduction of cumulative recurrent metastatic events (P<0.0001), translating into good progression-free survival.

A second milestone paper demonstrating the efficacy of neo-epitope based cancer vaccine has been published by Ott and coworkers (Nature (2017) 547, 217). In a phase I study patients with previously untreated high-risk melanoma (stage IIIB/C and IVM1a/b) were vaccinated with synthetic peptides covering several neo-epitopes in the presence of Hiltonol as adjuvant. Of the six vaccinated patients, four had no recurrence at 25 months post vaccination, and the two of them with recurring disease were treated with Pembrolizumab showing then complete tumor regression.

As said above, the success of therapeutic cancer vaccines requires formulations that induce potent immune responses that reverse or inhibit tumor-mediated immune evasion mechanisms. Moreover, in the case of personalized cancer vaccines, it is mandatory that the time from neoepitope identification to the preparation of the final vaccine formulation ready to be administered to patients is as short as possible, ideally no longer than two months. Therefore, the availability of new vaccine platforms which induce strong cancer-specific immune responses against both B and T cell epitopes and which allow the rapid formulation of cancer vaccines for personalized medicine is an urgent medical need.

STATE OF THE ART

WO2016/184860 discloses fusion proteins comprising a bacterial protein and a tumor antigen, and isolated bacterial outer membrane vesicles containing said fusion proteins, wherein the bacterial protein is selected from Factor H Binding Protein (fHbp), *Neisseria* heparin binding antigen (NHBA), Maltose Binding Protein (MBP), Outer Membrane Protein-F (ompF) and *Aggregatibacter actinomycetemcomitans* Factor H binding protein (Aa-fHbp).

WO2015/144691 discloses outer membrane vesicles isolated from a Gram-negative bacterium, wherein the OMV comprises at least one S. *Aureus* antigen, which can be FhuD2. The same antigen can be lipidated, e.g. with an acylated N-terminus cysteine.

WO2010/130899 discloses an outer membrane vesicle isolated from a Gram-negative bacterium, wherein the OMV comprises a lipoprotein consisting of the TbpB heterologous protein carrying an acylated N-terminal residue.

WO2006/024954 discloses fusion proteins for use as vaccine comprising a bacterial protein and an antigen, and outer membrane vesicles containing them.

WO2014/106123 discloses bacterial signal peptides/secretion chaperones as N-terminal fusion partners in translational reading frame with recombinant encoded tumor protein antigens, for use in stimulating an immune response.

DISCLOSURE OF THE INVENTION

The inventors have found that, differently from several other proteins, the *Staphylococcus aureus* FhuD2 expressed in Gram-negative bacteria, and in particular in *E. coli*, fused to lipoprotein leader sequences, not only reaches the outer membrane and is incorporated into OMVs, but also and surprisingly is transported to bacterial and OMV surface with high efficiency. Even more surprisingly, and particularly important for the purposes of this invention, the inventors have found that in such configuration FhuD2 mediates the surface translocation of a large number of heterologous polypeptides when fused thereto by genetic manipulation. Furthermore, and likewise surprisingly, the inventors have found that OMVs decorated with heterologous antigens/polypeptides fused to the FhuD2 are able to elicit antigen/polypeptide-specific immune responses when administered to a mammal.

Thus the invention provides a fusion protein containing the bacterial protein FhuD2 and one or more copies of a heterologous polypeptide. The latter can be fused at either the FhuD2 C- or N-terminus, but fusions at the FhuD2 C-terminus are preferred.

In a further embodiment, the invention provides a Gram-negative bacterium expressing on its surface said fusion protein and wherein said bacterium is used for biotechnological applications such as enzymatic reactions, selective capturing of molecules, elicitation of immune responses.

In a yet further embodiment the invention provides an outer membrane vesicle (OMV) from a Gram-negative bacterium, wherein the OMV comprises a fusion protein as herein defined and it is capable of eliciting an immune response toward the fusion protein and, in particular, the heterologous antigen, when administered to a mammal.

The OMVs of the invention can be obtained from any suitable Gram-negative bacterium. The Gram-negative bacterium is typically *E. coli*. However, other Gram-negative bacteria can be used.

In one embodiment the Gram-negative bacterium is a "hyperblebbing" strain in which the gene encoding OmpA, one of the major *E. coli* outer membrane proteins, has been inactivated or deleted. However, several other mutations leading to "hyper vesiculation" can be used.

In a preferred embodiment the FhuD2 fusion proteins are expressed on the surface using an expression vector comprising a nucleic acid sequence encoding the fusion proteins linked to a nucleic acid sequence encoding a signal sequence of a lipoprotein. The lipoprotein signal sequence is preferably linked to the FhuD2 encoding sequence, thereby allowing the production of fusion proteins lipidated at the FhuD2 N-terminal Cys residue, which are most efficiently transported to the OMV surface.

Any lipoprotein signal sequence can be used. For instance, signal sequences from lipoproteins expressed in any of following genera can be used: *Escherichia, Shigella, Neisseria, Moraxella, Bordetella, Borrelia, Brucella, Chlamydia, Haemophilus, Legionella, Pseudomonas, Yersinia, Helicobacter, Salmonella, Vibrio*, etc. For example, the signal sequence may be from *Bordetella pertussis, Borrelia burgdorferi, Brucella melitensis, Brucella ovis, Chlamydia psittaci, Chlamydia trachomatis, Moraxella catarrhalis, Escherichia coli* (including extraintestinal pathogenic strains), *Haemophilus influenzae* (including non-typeable stains), *Legionella pneumophila, Neisseria gonorrhoeae, Neisseria meningitidis, Neisseria lactamica, Pseudomonas aeruginosa, Yersinia enterocolitica, Helicobacter pylori, Salmonella enterica* (including serovar *typhi* and *typhimurium*), *Vibrio cholerae, Shigella dysenteriae, Shigella flexneri, Shigella boydii* or *Shigella sonnei*.

In a particular embodiment the FhuD2 fusion proteins are expressed on the surface using an expression vector comprising a nucleic acid sequence encoding the fusion proteins linked to a nucleic acid sequence encoding a signal sequence of any secretory protein followed by the lipobox (LB), having preferentially the sequence Leu-(Ala/Ser)-(Gly-Ala)-Cys. For instance, signal sequences from any of following genera can be used: *Escherichia, Shigella, Neisseria, Moraxella, Bordetella, Borrelia, Brucella, Chlamydia, Haemophilus, Legionella, Pseudomonas, Yersinia, Helicobacter, Salmonella, Vibrio*, etc. For example, the signal sequence may be from *Bordetella pertussis, Borrelia burgdorferi, Brucella melitensis, Brucella ovis, Chlamydia psittaci, Chlamydia trachomatis, Moraxella catarrhalis, Escherichia coli* (including extraintestinal pathogenic strains), *Haemophilus influenzae* (including non-typeable stains), *Legionella pneumophila, Neisseria gonorrhoeae, Neisseria meningitidis, Neisseria lactamica, Pseudomonas aeruginosa, Yersinia enterocolitica, Helicobacter pylori, Salmonella enterica* (including serovar *typhi* and *typhimurium*), *Vibrio cholerae, Shigella dysenteriae, Shigella flexneri, Shigella boydii* or *Shigella sonnei*.

In a particular embodiment the FhuD2 fusions are expressed on the surface using an expression vector comprising a nucleic acid sequence encoding the fusion proteins linked to a nucleic acid sequence encoding a signal sequence of the murein lipoprotein Lpp (MKATKLVLGAVILGSTL-LAGC, SEQ ID NO:76). However, any other suitable lipoprotein signal sequence can be used.

In a particular embodiment the FhuD2 fusions are cloned into the expression vector pET21b-derived plasmid. However, any other plasmid backbone suitable for bacterial gene expression known in the art can be used. Suitable plasmids include pGEX, pUC19, pALTR, pET, pQE, pLEX, pHAT or any other plasmid vector that is capable of replication in Gram-negative bacteria.

In another embodiment the FhuD2 fusion proteins can be integrated into the *E. coli* genome to create a stable strain expressing the fusion proteins of interest.

In another embodiment of the invention the heterologous protein can be an amino acid polymer of any length. The amino acid polymer may be linear or branched, it may comprise modified amino acids and it may be interrupted by non-amino acids. The polymer may have been modified naturally or by intervention (for example by disulfide bond formation, glycosylation, acetylation, phosphorylation). As used herein the term "heterologous" means that the protein is from a species that is different from the species of bacterium from which the OMV is obtained (the heterologous organism). Typically, the protein is an antigen from a pathogen genus different from the genus of bacterium from which the OMV is obtained. The protein may also be a human protein, and any portion of it, such as a tumor-associated and tumor-specific antigen, polypeptide and epitope.

In another embodiment of the invention the heterologous polypeptide can be any portion of a human protein that carries a specific amino acid mutation and where such mutation generates an immunogenic CD4+ and/or CD8+ T cell epitope.

In a specific embodiment of the invention, the fusion protein is an immunogenic protein which can elicit an immune response in a mammal. The protein can elicit an immune response against a protist, a bacterium, a virus, a fungus or any other pathogen and any cancer cell type. The immune response may comprise an antibody response (usually including IgG) and/or a cell-mediated immune response, such as antigen-specific CD4+ and CD8+ T cells. The antigens will typically elicit an immune response against the corresponding bacterial, viral, fungal or parasite polypeptide and cancer.

Any tumor antigen can be potentially used to construct the fusion protein according to the invention and particularly the following:

(a) cancer-testis antigens including NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12, which can be used, for example, to address melanoma, lung, head and neck, NSCLC, breast, gastrointestinal, and bladder tumours; (b) mutated antigens, including p53, associated with various solid tumours, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; MA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; PRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gplOO; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Me1-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, pl 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS.

The OMVs of the present invention comprise at least one FhuD2 fusion protein on the surface. The OMVs may contain more than one heterologous protein.

The invention also provides an isolated bacterial outer membrane vesicles (OMVs) loaded with a fusion protein as above defined. The isolated OMVs can contain a fusion protein carrying one species of tumor antigen or a plurality of fusion proteins carrying different tumor antigens.

The OMVs can be isolated and purified from Gram-negative bacteria, including species from any of genera *Escherichia, Shigella, Neisseria, Moraxella, Bordetella, Borrelia, Brucella, Chlamydia, Haemophilus, Legionella, Pseudomonas, Yersinia, Helicobacter, Salmonella, Vibrio,* etc. For example, the vesicles may be from *Bordetella pertussis, Borrelia burgdorferi, Brucella melitensis, Brucella ovis, Chlamydia psittaci, Chlamydia trachomatis, Moraxella catarrhalis, Escherichia coli* (including extraintestinal pathogenic strains), *Haemophilus influenzae* (including non-typeable stains), *Legionella pneumophila, Neisseria gonorrhoeae, Neisseria meningitidis, Neisseria lactamica, Pseudomonas aeruginosa, Yersinia enterocolitica, Helicobacter pylori, Salmonella enterica* (including serovar *typhi* and *typhimurium*), *Vibrio cholerae, Shigella dysenteriae, Shigella flexneri, Shigella boydii* or *Shigella sonnei.*

A particularly useful choice for the production of OMVs is *E. coli* BL21(DE3) strain and any derivative of this strain carrying specific gene mutations. Particularly useful are mutations in genes such as ompA and tol/Pal, that improve vesiculation. Other useful mutations are those involving genes of the lipopolysaccharide (LPS) synthetic pathway, such as the msbB gene, that reduce the reactogenicity of OMVs.

Other useful choices for the production of OMVs decorated with FhuD2 fusions are strains carrying one or more mutations in genes encoding non-essential proteins naturally present in OMVs. Such strains can facilitate the accumulation of the FhuD2 fusions in the OMV compartment and/or can enhance the immune responses against the heterologous antigen fused to FhuD2.

Bacterial vesicles can conveniently be separated from whole bacterial culture by filtration e.g. through a 0.22 µm filter. Bacterial filtrates may be clarified by centrifugation, for example high speed centrifugation (e.g. 200,000×g for about 2 hours). Another useful process for OMV preparation is described in WO2005/004908 and involves ultrafiltration on crude OMVs, instead of high speed centrifugation. The process may involve a step of ultracentrifugation after the ultrafiltration takes place. A simple process for purifying bacterial vesicles comprising: (i) a first filtration step in which the vesicles are separated from the bacteria based on their different sizes, and (ii) tangential flow filtration using membranes that retain vesicles, thus allowing their concentration.

In a further embodiment, the invention provides an immunogenic composition comprising a bacterial outer membrane vesicle as herein disclosed, together with pharmaceutical acceptable vehicles and excipients. The immunogenic composition may contain a mixture of outer membrane vesicles differing from each other for the type of tumor antigen fused to FhuD2.

In a further embodiment, OMVs or a mixture of outer membrane vesicles carry cancer-specific T cell epitopes generated by gene mutations and such mixture of vesicles is used as personalized cancer vaccine.

The compositions of the invention are suitable for administration to subjects and they are preferably vaccine compositions. Vaccines according to the invention may either be prophylactic (e.g. to prevent cancer) or therapeutic {e.g. to treat cancer). Pharmaceutical compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated {e.g. non-human primate, primate, etc.), the capacity of the individual's immune system to stimulate antibody production, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. The amount of OMVs in compositions of the invention may generally be between 10 and 500 µg, preferably between 25 and 200 µg, and more preferably about 50 µg or about 100 µg.

Compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops, and intranasal vesicle vaccines are known in the art. Injectables for intramuscular administration are typical. Injection may be via a needle (e.g. a hypodermic needle), but needle-free injection may alternatively be used.

The OMVs and the immunogenic compositions according to the invention are conveniently used for the stimulation of an immune response against tumor in a subject in need thereof. Particularly they can be used for the prevention or treatment of different types of tumor, including but not limited to bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, prostate cancer or lymphocytic leukaemias.

In a preferred embodiment, the isolated bacterial outer membrane vesicles or the immunogenic composition are used in the prevention or treatment of tumors selected from breast, brain, head-and-neck, non-small cell lung, renal, ovarian, kidney, stomach, prostate and colon cancer, oral cancer, astrocytoma, glioblastoma, ductal carcinoma, cholangiocarcinoma, hepatocarcinoma, acute myeloid leukemia, acute lymphoblastic leukemia, melanoma, pancreatic cancer and prostate cancer.

Figure 1:
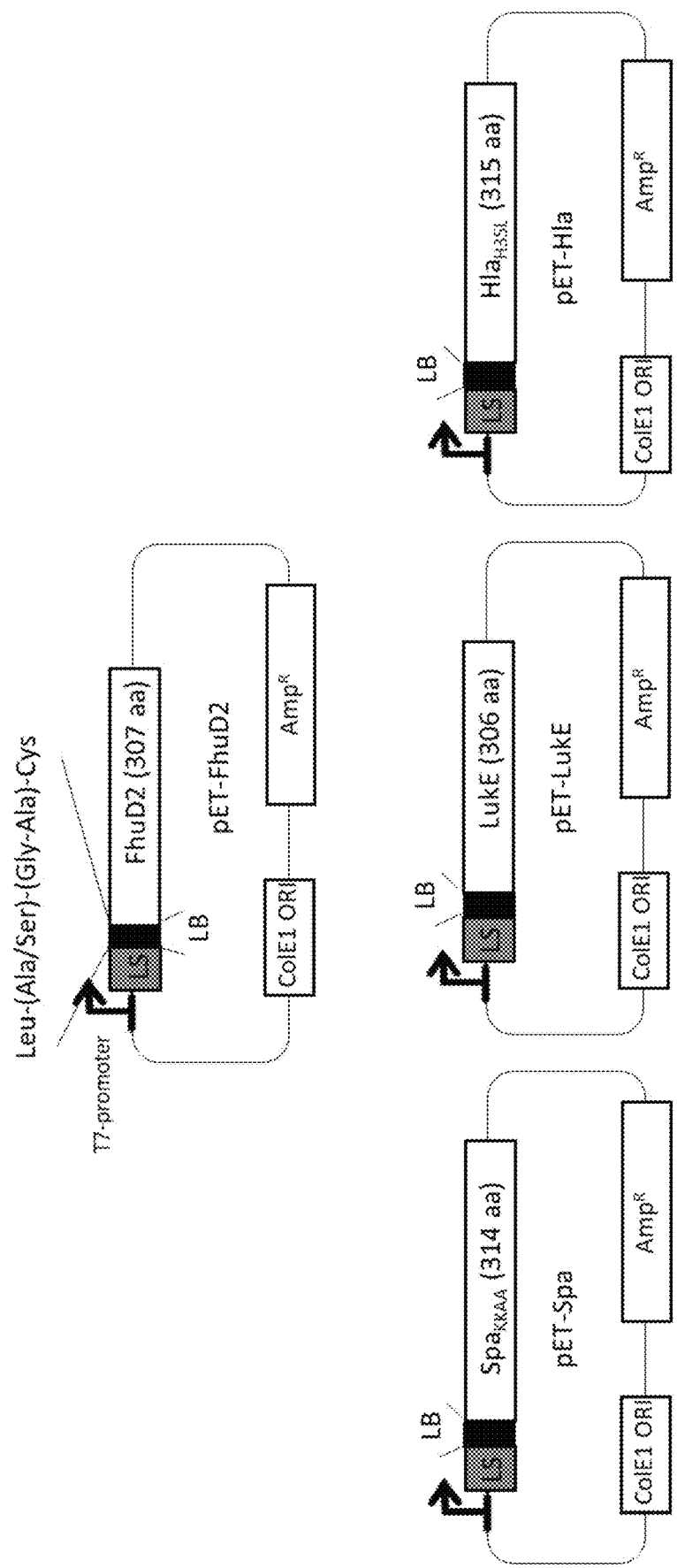
FIG. 1

Schematic representation of the plasmids expressing heterologous proteins fused to a lipoprotein leader sequence— The genes encoding the *S. aureus* proteins Spa (encoding sequence SEQ ID NO:5; amino acid sequence SEQ ID NO:21), $Hla_{H35L}$ (encoding sequence SEQ ID NO:3; amino acid sequence SEQ ID NO:19), FhuD2 (encoding sequence SEQ ID NO:1; amino acid sequence SEQ ID NO:17; lipidated-FhuD2: encoding sequence SEQ ID NO:2, amino acid sequence SEQ ID NO:18) and LukE (encoding sequence SEQ ID NO:7; amino acid sequence SEQ ID NO:23) were chemically synthesized and fused to the 3' end of the sequence coding for a lipoprotein leader sequence. Gene expression was driven by an inducible T7 promoter.

FIG. 2

SDS-PAGE of total lysates and OMVs from BL21(DE3) ΔompA strains expressing *S. aureus* lipoproteins—Total cell lysates and OMVs purified from BL21(DE3)ΔompA recombinant strains expressing the *S. aureus* proteins Spa, $Hla_{H35L}$, FhuD2 and LukE as lipoproteins were separated by SDS-PAGE and stained with Coomassie brilliant blue. Arrows highlight the bands corresponding to the lipoproteins. "Empty" OMVs were purified from BL21(DE3) ΔompA strain transformed with pET21b empty vector and were used as negative control.

FIG. 3

Analysis of surface exposition of: (A) FhuD2 in BL21 (DE3)ΔompA(pET-FhuD2) recombinant strain, (B) Hla, in BL21(DE3)ΔompA(pET-Hla) recombinant strain, (C) LukE in BL21(DE3)ΔompA(pET-LukE) recombinant strain and (D) Spa in BL21(DE3)ΔompA(pET-Spa) recombinant strain, evaluated by flow cytometry and confocal microscopy analysis—Localization of FhuD2, HlaH35L, LukE and Spa expressed as heterologous lipoproteins was evaluated on bacterial cells after 2 h induction with 0.1 mM IPTG. Cells were stained with anti-FhuD2, anti-Hla, anti-LukE or anti-Spa rabbit polyclonal antibodies followed by anti-rabbit-FITC or alexa fluor 594-labelled anti-rabbit (for confocal analysis) secondary antibodies. BL21(DE3)ΔompA(pET) strain was used as a negative control. Fluorescence was measured by flow cytometry and by confocal microscopy. Grey areas represent the background fluorescence signals obtained incubating the cells with the secondary antibody only.

FIG. 4

Cloning strategy used to fuse three copies of human and murine D8-FAT1 epitopes to the C-terminus of FhuD2—The DNA sequences coding for three copies of human and murine FAT1 epitopes were PCR amplified from pET-MBP-hFAT1 plasmid and pET-MBP-mFAT1 plasmid, respectively (for simplicity, the two plasmids are referred to as pET-MBP-FAT1). The pET-FhuD2 vector was linearized by PCR using the primers nohis flag F/FhuD2-V-R. Finally, the PCR products were mixed together and used to transform HK-100 competent cells, obtaining plasmids pET-FhuD2-D8-hFAT1-3x (encoding sequence SEQ ID NO:9; amino acid sequence SEQ ID NO:25) and pET-FhuD2-D8-mFAT1-3x (encoding sequence SEQ ID NO:10; amino acid sequence SEQ ID NO:26) (for simplicity, the two plasmids are referred to as pET-FhuD2-D8-FAT1-3x).

FIG. 5

Representation of pET-FhuD2-D8-hFAT1-3x and pET-FhuD2-D8-mFAT1-3x plasmids.

Plasmid pET-FhuD2-D8-hFAT1-3x, Seq ID NO: 9, encoding amino acid sequence SEQ ID NO: 25 and represents plasmid pET-FhuD2-D8-mFAT1-3x encoding sequence ID NO: 10, amino acid sequence SEQ ID NO:26.

The DNA sequences refer to the 3' end of the gene fusion encoding three copies of D8-hFAT1 or D8-mFAT1.

FIG. 6

Cloning strategy used to fuse three copies of EGRF-vIII epitope to FhuD2—To fuse three copies of EGFR-vIII to FhuD2, pET-FhuD2 plasmid was PCR-amplified using primers nohisflag/FhUD2-V-R while the DNA sequence coding for three copies of EGFR-vIII epitope (vIII-x3) was PCR-amplified from pUC-vIII-x3 using primers vIII-FhuD2-F/vIII-FhuD2-R. Finally, the PCR products were used to transform *E. coli* HK100 cells to allow the recombination of the complementary ends, obtaining pET-FhuD2-EGFR-vIII-3x (encoding sequence SEQ ID NO:11; amino acid sequence SEQ ID NO:27) plasmid.

FIG. 7

Schematic representation of pET-FhuD2-EGRF-vIII-3x plasmid.

Plasmid pET-FhuD2 EGFR-vIII-x3, encoding sequence SEQ ID NO:11, amino acid sequence SEQ ID NO:27). The DNA sequence refers to the 3' end of the gene fusion encoding three copies of EGFR-vIII.

FIG. 8

Cloning strategy used to fuse three copies of $OVA_{257-264}$ and M03, M20, M26, M27, M68 single epitope to the FhuD2 lipoprotein—Two DNA fragments one coding for the M03, M20, M26, M27, M68 epitopes and the other for three copies of $OVA_{257-264}$ peptide were chemically synthetized as synthetic DNA string (Thermo Fisher). Each single epitope and the three copies of OVA was then amplified by PCR from the synthetic DNA using specific forward and reverse primers. These primers generated extremities complementary to the vector pET-FhuD2 donor plasmid. The pET-FhuD2 vector was linearized by PCR amplification using the divergent primers nohis flag F/FhuD2-V-R. Finally, the PCR products were mixed together and used to transform HK-100 competent cells, obtaining plasmids pET-FhuD2-epitope.

FIG. 9

Schematic representation of pET-FhuD2-M03 (encoding sequence SEQ ID NO:12; amino acid sequence SEQ ID NO:28), pET-FhuD2-M20 (encoding sequence SEQ ID NO:13; amino acid sequence SEQ ID NO:29) and pET-FhuD2-M26 (encoding sequence SEQ ID NO:14; amino acid sequence SEQ ID NO:30) plasmids—The DNA sequence refers to the 3' end of the gene fusion encoding each epitope.

FIG. 10

Schematic representation of pET-FhuD2-M27 (encoding sequence SEQ ID NO:15; amino acid sequence SEQ ID NO:31), pET-FhuD2-M68 (encoding sequence SEQ ID NO:16; amino acid sequence SEQ ID NO:32) and pET-FhuD2-OVA-3X (encoding sequence SEQ ID NO:77;

amino acid sequence SEQ ID NO:78) (plasmids—The DNA sequence refers to the 3' end of the gene fusions encoding each epitope.

FIG. 11

SDS-PAGE of OMVs from BL21(DE3)ΔompA strains expressing different epitopes fused to FhuD2 protein—OMVs were purified from BL21(DE3)ΔompA recombinant strains, each expressing one specific FhuD2 fusion (FhuD2-D8-hFAT1-3x, FhuD2-D8-mFAT1-3x, FhuD2-EGRF-vIII-3x, FhuD2-M03, FhuD2-M20, FhuD2-M26, FhuD2-M27, FhuD2-M68, FhuD2-OVA-3X). Total OMV proteins were separated by SDS-PAGE and stained with Coomassie brilliant blue. Arrows highlight the bands corresponding to recombinant antigens.

FIG. 12

Flow cytometry analysis of BL21(DE3)ΔompA cells expressing epitopes fused to the FhuD2 lipoprotein—Surface exposition of FhuD2 fusion proteins was evaluated on bacterial cells after 2 h induction with 0.1 mM IPTG. Cells were stained with: (D), (E) and (F), anti-FhuD2 antibodies (cells expressing FhuD2-M03, FhuD2-M20, FhuD2-M26, FhuD2-M27 and FhuD2-M68), (C) anti-EGFR-vIII antibodies (cells expressing FhuD2-EGRF-vIII-3x), A anti-D8-hFAT1 antibodies (cells expressing FhuD2-D8-hFAT1-x3), or B anti D8-mFAT1 antibodies (cells expressing FhuD2-D8-mFAT1-x3) followed by incubation with FITC secondary antibodies. Fluorescence was measured by flow cytometry. Grey areas represent the background fluorescence signals obtained incubating the cells with the secondary antibody only.

FIG. 13

Epitope-specific antibody titers in mice immunized with OMVs from recombinant strains expressing FhuD2-D8-mFAT1-3x, FhuD2-D8-hFAT1-3x and FhuD2-EGFR-vIII-3x—(A) Schematic representation of immunization schedule in CD1 mice. (C) Anti-D8-hFAT1 in CD1 mice immunized with "empty" OMVs (negative control) or with FhuD2-D8-mFAT1-3x-OMVs, (B) Anti anti-D8-mFAT1 in CD1 mice immunized with "empty" OMVs (negative control) or with FhuD2-D8-hFAT1-3x-OMVs and (D) Anti EGRF-vIII antibody titers in CD1 mice immunized with "empty" OMVs (negative control) or with FhuD2-EGFR-vIII-3x-OMVs. Sera from mice immunized as reported in the immunization schedule were pooled and total IgGs were measured by ELISA, on plates coated with the corresponding synthetic peptide.

FIG. 14

Analysis of specific CD4+ and CD8+ T cells induced in mice immunized with OMVs decorated with FhuD2-M03, FhuD2-M20, FhuD2-M26, FhuD2-M27, FhuD2-M68 and FhuD2-OVA-3X fusion proteins—(A) Immunization schedule in Balb/c mice. Mice were immunized twice i.p. at days 0 and 7 with 4 ug each of OMVs purified from E. coli strains transformed with pET-FhuD2-M03, pET-FhuD2-M20, pET-FhuD2-M26, pET-FhuD2-M27, pET-FhuD2-M68 and 20 ug of OMVs purified from E. coli strain transformed with pET-FhuD2-OVA-3X. Five days after the second immunization, splenocytes were stimulated with either an irrelevant peptide (negative control) or with the mix of the five selected peptides and OVA peptide. The double positive T cells population IFNγ+/CD4+ and IFNγ+/CD8+ was analyzed by flow cytometry (B). (C) and D) Example of flow cytometry analysis of stimulated splenocytes isolated from a single immunized mouse. The gated cells correspond to the specific CD4+ and CD8+ T cells specific for the selected epitopes.

FIG. 15

Protective activity of FhuD2-D8-mFAT1-3x-OMVs and FhuD2-M03, FhuD2-M20, FhuD2-M26, FhuD2-M27, FhuD2-M68 OMVs mix in mice challenged with CT26—(A) Immunization schedule. Four groups of 6 Balb/c mice were i.p. immunized three times every two weeks with 20 ug/mouse of "empty" OMVs (Gr1 and Gr2—control groups) and 20 ug/mouse of FhUD2-D8-mFAT1-3x-OMVs (Gr3 and Gr4). A week after the last immunization, mice were challenged with $2.5 \times 10^5$ CT26 cells per mouse. The following day and for about twenty days groups 2 and 4 were i.p. immunized every three days with 20 μg "empty" OMVs absorbed to 20 μg each of M03, M20, M26, M27 and M68 synthetic peptides mix. (B) Tumor volumes were measured every 3 days up to day 27.

(C) Immunization schedule. Two groups of 6 Balb/c mice were challenged with $2.5 \times 10^5$ CT26 cells per mouse and the day after were i.p. immunized 20 ug/mouse of "empty" OMVs (Gr1) and 4 μg each of a mixture of five OMVs decorated with one of the fusion proteins FhUD2-M03, FhuD2-m20, FhuD2-M26, FhuD2-M27, FhuD2-68 epitopes. Mice were immunized six times every 3 days and (D) tumor volumes measured at day 11, 15, 18 and 21 post challenge.

DETAILED DESCRIPTION OF THE INVENTION

Lipidated FhuD2 has the Peculiar Property to Protrude Out of the Surface of Gram-Negative Bacteria Some proteins have the property to be successfully expressed in heterologous bacterial hosts as lipoproteins. For instance, when expressed in E. coli fused to a leader sequence carrying a canonical "lipobox", a selected group of proteins from Group A Streptococcus and Staphylococcus aureus were lipidated, could reach the membrane compartment and could be incorporated into OMVs (Patent application EP16195315). At present, the intrinsic structural properties requested to a protein to enter the lipoprotein expression and secretory pathway of a heterologous host are not known and therefore whether or not a heterologous protein can be efficiently expressed in the membrane compartment in a lipidated form has to be experimentally tested. Even more unpredictable is its final destination once the membrane compartment is reached. Considering that in E. coli almost all endogenous lipoproteins (more than 90 lipoproteins are annotated in the E. coli genome) are exclusively retained in the outer membrane and face the periplasmic space (Okuda & Tokuda, 2011—Annu. Rev. Microbiol. 65:239-59), it is reasonable to believe that a similar topological organization is adopted by most if not all heterologous lipidated proteins expressed in E. coli.

To address the question of the topological organization of heterologous proteins expressed in E. coli as lipoproteins, the localization of four proteins from Staphylococcus aureus was analyzed. These four proteins, $Hla_{H35L}$ (encoding sequence SEQ ID NO:3; amino acid sequence SEQ ID NO:19) (Menzies, B. E., and D. S. Kernodle. (1996) Infect. Immun. 64:1839-1841, (Wardenburg and Schneewind (2008) J. Exp. Med. 205:287-294), FhuD2 (encoding sequence SEQ ID NO:1; amino acid sequence SEQ ID NO:17; lipidated-FhuD2: encoding sequence SEQ ID NO:2, amino acid sequence SEQ ID NO:18) (Mishra et al. J. Infect. Dis. 2016, 1041-1049), $Spa_{KKAA}$ (encoding sequence SEQ ID NO:5; amino acid sequence SEQ ID NO:21) (Kim et al., (2010) J. Exp. Med. 207, 1863), and LukE (encoding sequence SEQ ID NO:7; amino acid sequence SEQ ID NO:23) (Alonzo et al., (2013) PLoS Pathog.; 9:e1003143;

Reyes-Robles et al., (2013) Cell Host Microbe. October 16; 14(4):453-9, Alonzo & Torres, (2014) Microbiol Mol Biol Rev. 2014 June; 78(2):199-230), had been previously shown to enter the lipoprotein secretory pathway of E. coli when fused to a lipoprotein leader sequence but their cellular localization was unknown. The DNAs coding for the four genes were chemically synthesized and the synthetic genes were inserted into an expression vector downstream from a lipoprotein leader sequence. In so doing, fusion proteins were generated in which the lipoprotein leader sequence was fused to the N-terminus of each heterologous antigen. The schematic representation of the four plasmids expressing the four heterologous lipoproteins is reported in FIG. 1. Also, the nucleotide sequences and the amino acid sequences of the four genes and corresponding proteins in the non-lipidated and lipidated forms are reported (SEQ ID NO 1, 2, 5, 7, 17, 18, 21, 23). It is important to point out that different experimental procedures can be used to obtain the fusions proteins. Such procedures are well known to those skills in the art, and include PCR for instance amplifications of the protein coding sequences from chromosomal DNA, use of restriction enzymes, use of different expression plasmids.

Figure 2:
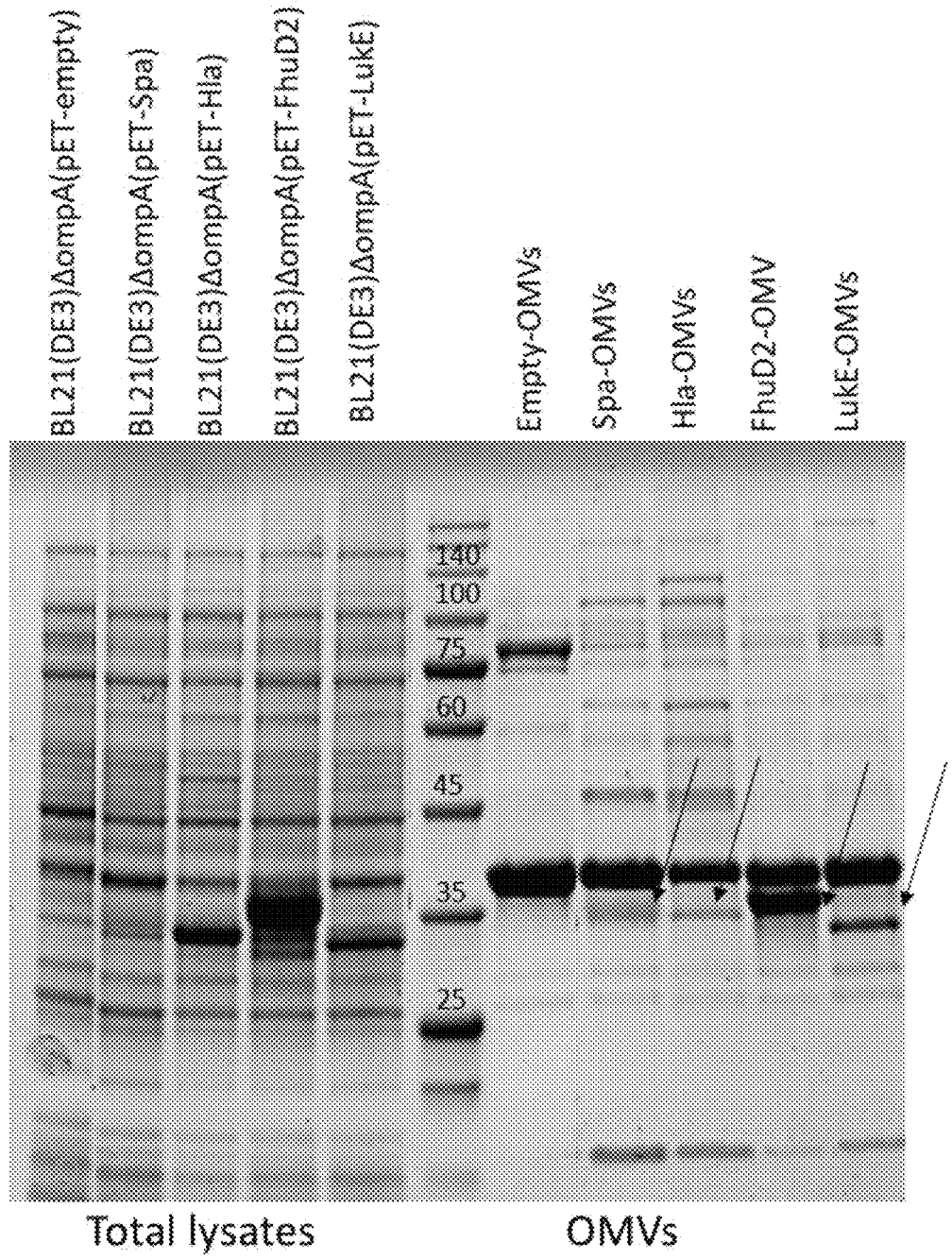

The recombinant plasmids reported in FIG. 1 were used to transform E. coli strain BL21(DE3)ΔompA, obtaining the four recombinant strains BL21(DE3)ΔompA(pET-FhuD2), BL21(DE3)ΔompA(pET-Hla), BL21(DE3)ΔompA(pET-LukE), and BL21(DE3)ΔompA(pET-Spa). Each strain was grown in LB medium and when the cultures reached an $OD_{600}$ value=0.5, IPTG was added at 1 mM final concentration. After two additional hours of growth at 37° C., the expression of the heterologous proteins was analyzed in bacterial cells collected by centrifugation and in the OMVs purified from the culture supernatant by filtration through a 0.22 μm pore size filter (Millipore) and by high-speed centrifugation (200,000×g for 2 hours). As shown in FIG. 2 all antigens could be visualized by Coomassie Blue in both total cell extracts and OMVs.

Figure 3:
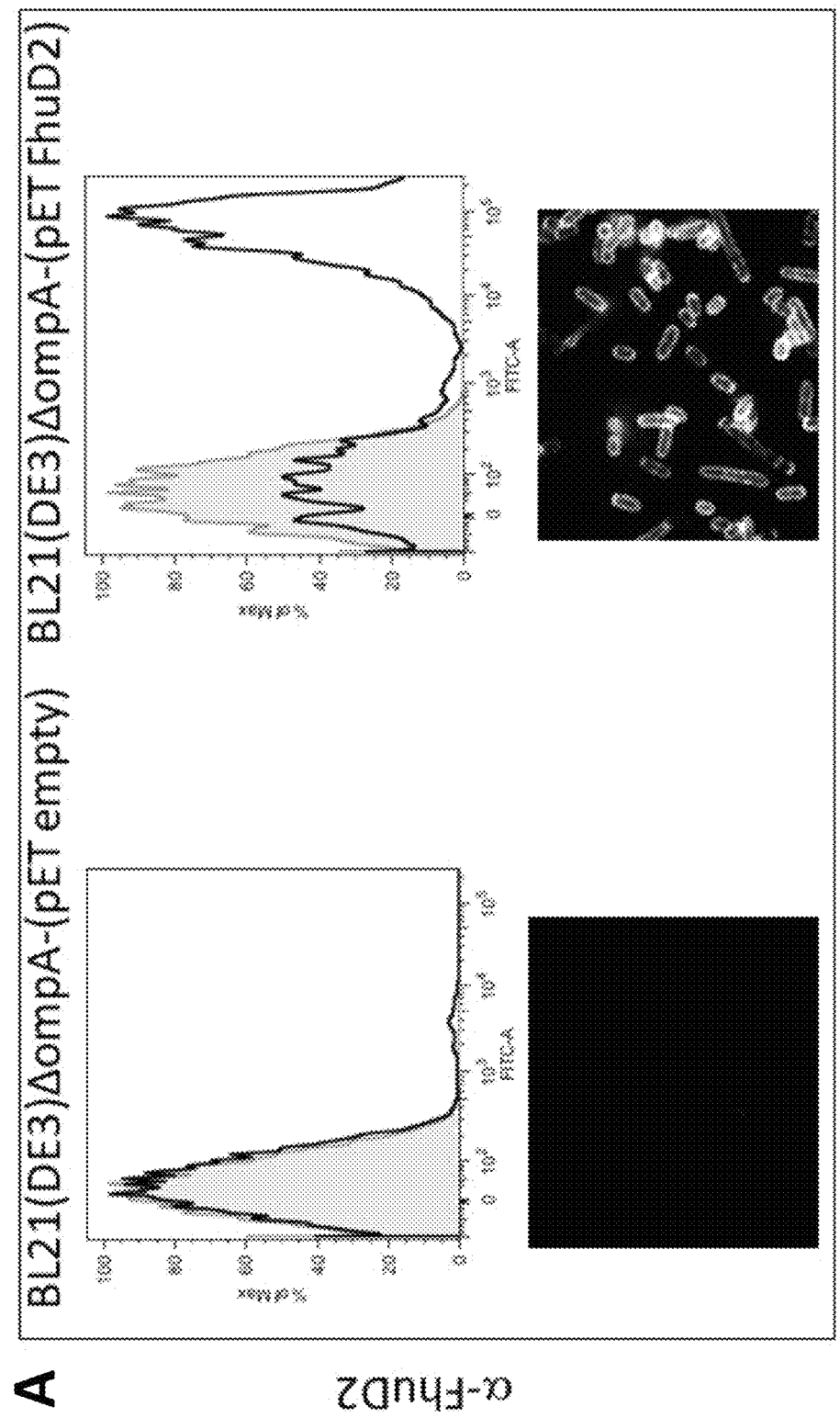
Figure 3:
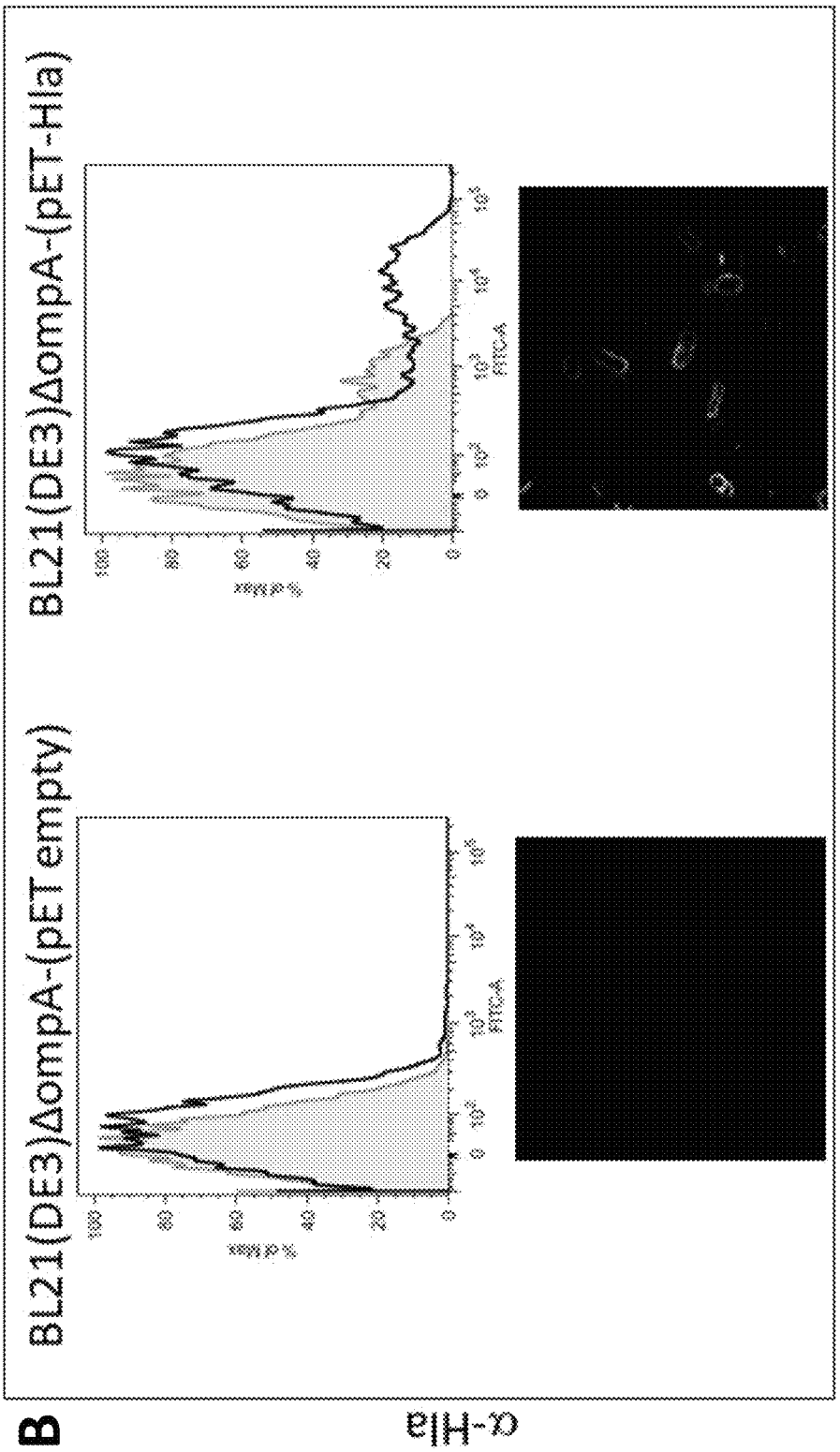
Figure 3:
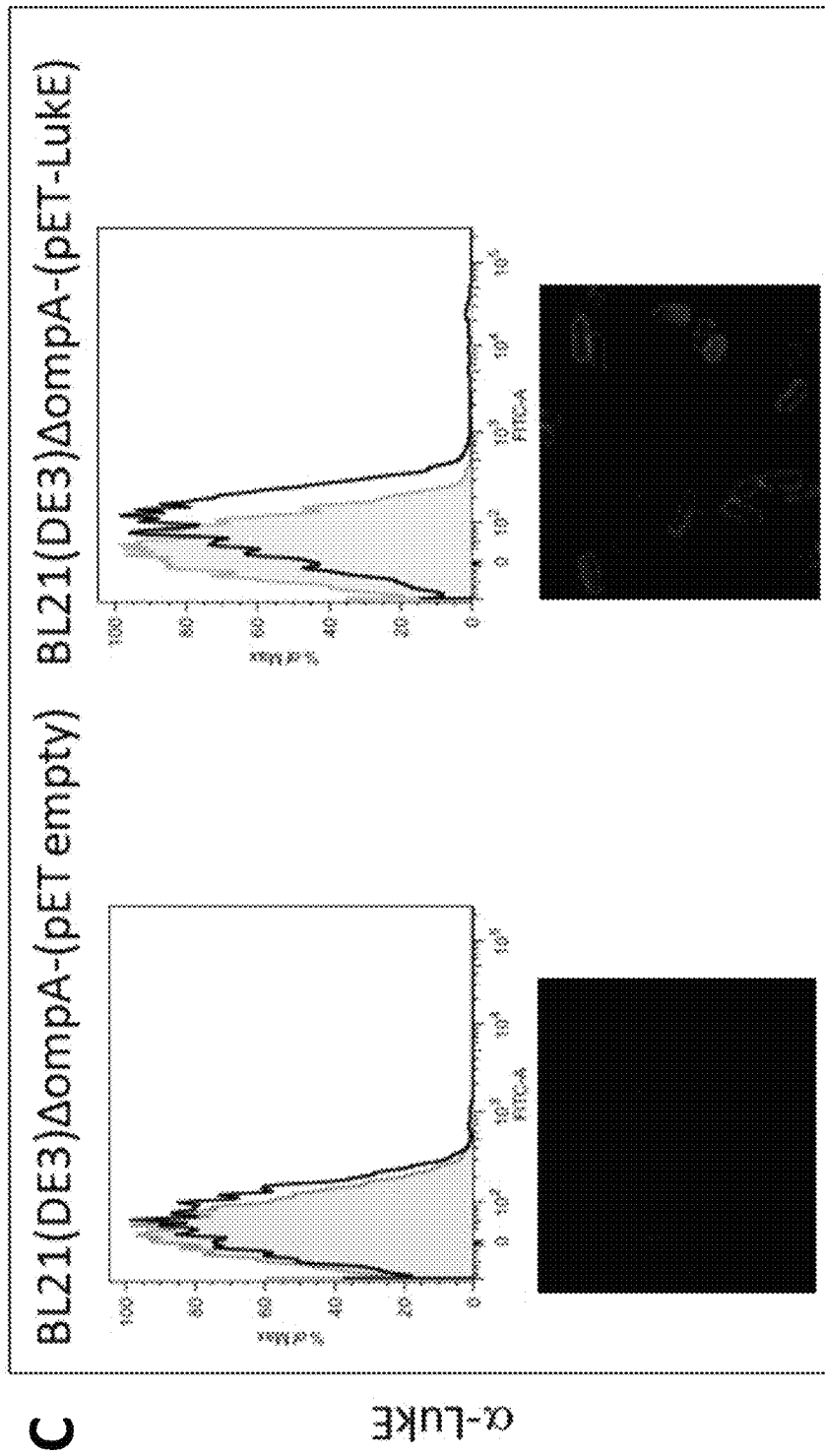
Figure 3:
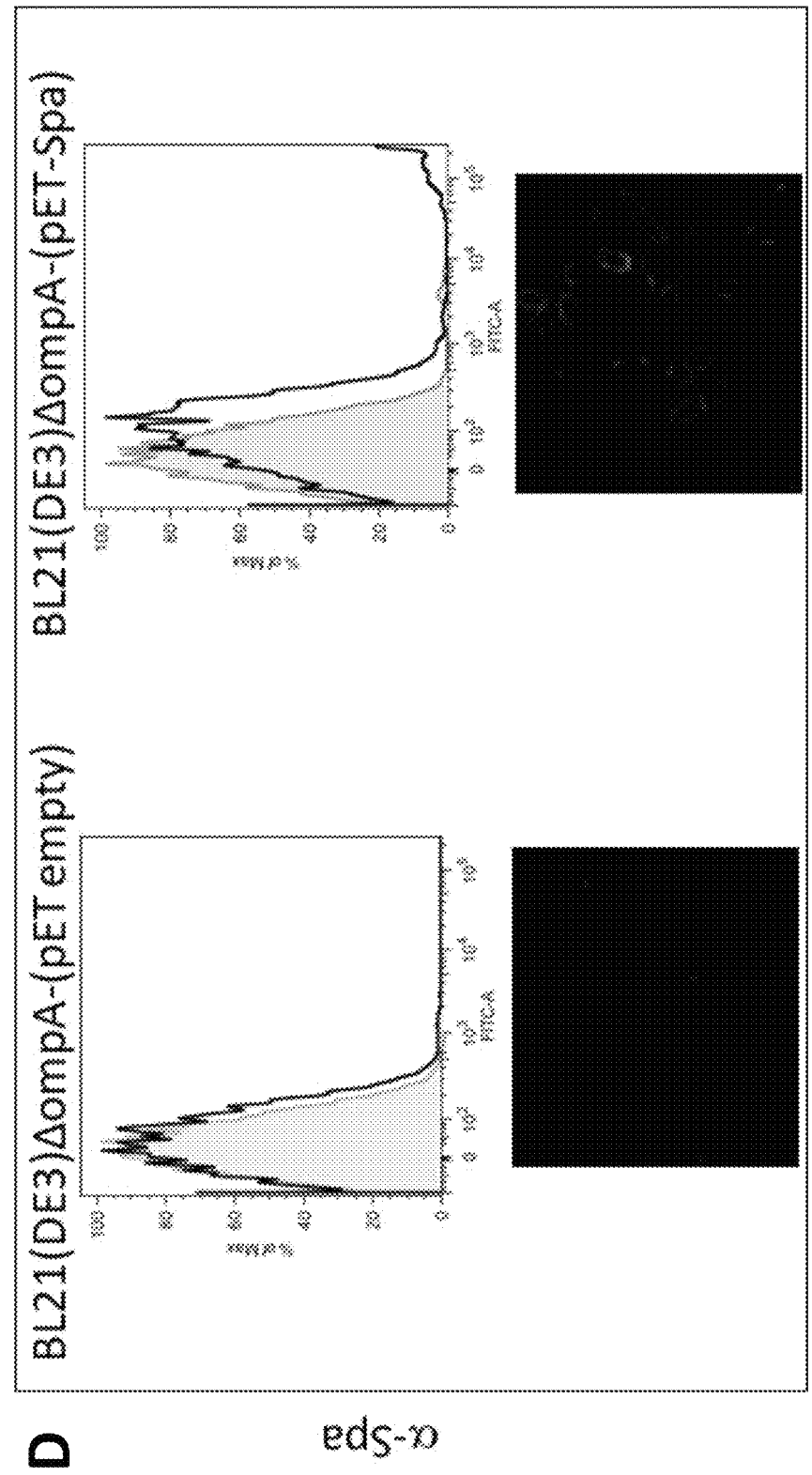

In parallel, bacteria cells corresponding to those contained in 1 ml culture at $OD_{600}$=1 were re-suspended in 1 ml of 1% BSA in PBS and diluted 1:50 in 1% BSA in PBS. 50 μl of cell suspensions were then incubated with 50 μl of 1% BSA in PBS (negative control) or with 50 μl of an appropriate dilution of anti-FhuD2, anti-Hla, anti-LukE or anti-Spa rabbit polyclonal antibodies obtained by immunizing rabbits with specific synthetic peptides (MDDGKTVDIPKDPKC (SEQ ID NO:69) for FhuD2, CGTNTKDKWIDRSSE (SEQ ID NO:70) for Hla, CNEFVTPDGKKSAHD (SEQ ID NO:71) for LukE, CAKKLNDAQAPKADN (SEQ ID NO:72) for Spa) conjugated with Keyhole Limpet Hemocyanin (KLH) protein. After 1 hour, 100 μl of 1% BSA in PBS were added, the suspensions were centrifuged at 3,000×g for 10 minutes and supernatants discarded. Pellets were washed with 200 μl of 1% BSA in PBS and bacteria were subsequently incubated for 30 minutes on ice with Alexa flour488-goat anti-rabbit antibodies (Life Technology) added at a final dilution of 1:2,00. Finally, after 2 washing steps, pellets were re-suspended in 200 μl of PBS and analyzed with FACS CANTOII (BD). Data were analyzed with FlowJo software. Confocal microscopy was also used to analyze the localization of FhuD2, $Hla_{H35L}$, LukE and Spa lipoproteins on the membrane of E. coli cells. After induction of the lipoproteins expression, as described above, bacteria were fixed with 2% formaldehyde solution and incubated 1 hour at room temperature with anti-FhuD2, anti-Hla, anti-LukE and anti-Spa antibodies. After two washes with PBS-0.1% BSA, bacteria were incubated for 20 min at room temperature with alexa fluor 594-labelled anti-rabbit antibodies (white). at 1:400 final dilution. Labeled bacteria were washed twice with PBS supplemented with 0.1% BSA, and allowed to adhere to polylysine slides (Thermo Scientific) for 20 min at room temperature. Slides were mounted with ProLong Gold antifade reagent (Thermo Scientific). Confocal microscopy analysis was performed with a Laica SP5 microscope and images were obtained using Laica LASAF software. As shown in FIG. 3, no substantial difference in fluorescence intensity was observed when BL21(DE3)ΔompA(pET-H1a), BL21(DE3)ΔompA (pET-LukE), BL21(DE3) ΔompA(pET-Spa) strains were incubated with the corresponding antibodies. This is in line with the fact that, as said above, most of lipoproteins are not surface exposed in E. coli. Surprisingly however, when E. coli BL21(DE3)ΔompA(pET-FhuD2) strain was incubated with anti-FhuD2 antibodies, a clear shift in fluorescence intensity was observed in a substantial fraction of bacterial cells expressing FhuD2. Furthermore, confocal microscopy analysis confirmed that BL21(DE3)ΔompA(pET-FhuD2) strain was effectively stained by anti-FhuD2 antibodies.

These data indicate that expressing heterologous proteins as fusions to lipoprotein leader sequences in Gram-negative bacteria, and in E. coli in particular, usually does not promote their efficient exposition to the surface of the outer membrane. However, we unexpectedly found that when such fusion strategy is applied to FhuD2, the protein has the peculiarity not only to abundantly compartmentalize in OMVs, but also to reach the bacterial and OMV surface with high efficiency.

The peculiar topology of lipidated FhuD2 in Gram-negative bacteria, together with the abundancy of its expression, makes the protein a potential unique carrier of foreign polypeptides intended to be expressed on the surface of Gram-negative bacteria and/or to be compartmentalized in OMVs.

FhuD2 can Chaperone Foreign Antigens/Polypeptides to the E. coli Surface-Description of the Foreign Polypeptides Used to Demonstrate the Universal Applicability of FhuD2 as Surface Chaperone To test the ability of FhuD2 to chaperone heterologous polypeptides to the surface of E. coli, eight polypeptides corresponding to B and T cells cancer epitopes were used. By no means the successful application of FhuD2 fusion strategy should be considered restricted to these polypeptides. Rather, these examples are reported to demonstrate the general applicability of lipidated FhuD2 as surface delivery system of foreign polypeptides.

Human D8-FAT1 Epitope

Human FAT gene family is a subclass of the cadherin superfamily, composed of four giant proteins (FAT1-4) of 500-600 kDa sharing structural similarities from invertebrates to mammals. Human FAT1 is a type 1 transmembrane protein carrying 34 cadherin repeats, five EGF-like repeats, a laminin A-G domain in the extracellular region and a cytoplasmic tail (Dunne, J. et al., (1995) Genomics 30, 207-23; Moeller, M. J. et al., (2004) The EMBO journal, 23, 3769-79; Morris, L. G. T. et al., (2013) Nature Genetics 45, 253-61).

Alteration of FAT1 expression and function has been clearly associated to several human cancers (De Bock, C. E. et al., (2012) Leukemia, 26, 918-26; Valletta, D. et al., (2014) Carcinogenesis, 35, 1407-15) and leukemia (de Bock et al. 2012). Recently, (Pileri et al, British Journal of Cancer (2016) 115, 40-51) it was discovered that FAT1 is expressed in a large fraction of early and late stage CRCs. Moreover, a murine monoclonal antibody (mAb198.3) was isolated that selectively binds the surface of different FAT1-positive colon cancer cell lines and, upon binding, it is efficiently internalized. mAb198.3 was shown to recognize an epitope present on cadherin domain 8 (D8) and cadherin domain 12 (D12), and antibody binding was efficiently abrogated in the presence of the synthetic peptide IQVEATDKDLGPNGHVTYSIVTDTD (D8-hFAT1—SEQ ID NO:73) designed on the basis of the amino acid sequence of D8 domain. Therefore, this polypeptide represents a promising antigen potentially capable of inducing antibodies specific for FAT1-positive human colon cancers.

Mouse D8-FAT1 Epitope

Similarly to hFAT1, the mouse homolog mFAT1 is found expressed on the surface of a number of murine cell lines, including the mouse colon cancer cell line CT26 and the mouse melanoma cancer cell line B16. mFAT1 has a 98% amino acid identity to hFAT1 and in particular in mFAT1 the D8 polypeptide differs from the human counterpart for four amino acids, the sequence being IQVEATDKDLGPSGHVTYAILTDTE (SEQ ID NO:74). Interestingly, such amino acid difference is sufficient to abrogate the binding of mAb198.3.

EGFR-vIII Epitope

Abnormal cell signaling by EGF receptor has been implicated in numerous cancers. In the majority of solid tumors, including breast, brain, head-and-neck, non-small-cell lung, renal, ovarian, prostate and colon cancer EGFR is overexpressed (Wong A J et al., (1992) Proc. Natl Acad. Sci. USA 89, 2965-2969; Gorgoulis V et al. (1992) Anticancer Res. 12, 1183-1187; Irish J C et al. (1993) Laryngoscope 103, 42-52; Korc M et al. (1986) Proc. Natl Acad. Sci. USA 83, 5141-5144; Moorghen M et al. (1990) Anticancer Res. 10, 605-611; Ishikawa J et al., (1990) Int. J. Cancer 45, 1018-1021; Zajchowski D et al., (1988) Cancer Res. 48, 7041-7047). EGFR overexpression leads to the enhancement of downstream signaling pathways stimulating growth and invasiveness of cancer cells.

In addition to overexpression, there is a naturally occurring variant of the EGF receptor called EGFR-vIII. This variant derives from an in-frame 801 base pair deletion of exons 2-7. This deletion gives rise to a truncated receptor that renders EGFR-vIII signaling ligand-independent and constitutively active. Different tumors have also been shown to express this variant, including glioblastoma, lung, breast, ovarian and prostate cancer (Moscatello D K et al., (1995) Cancer Res. 55, 5536-5539).

The in-frame deletion of the extracellular domain of EGFR creates a novel antigenic epitope which is exquisitely tumor-specific (Humphrey et al., (1990) PNAS, 87, 4207). Therefore, the newly generated epitope can be exploited in active and passive immunization. Indeed, a vaccine has been developed (Rindopepimut) which is based on a 14-amino acid peptide (LEEKKGNYVVTDHC, SEQ ID NO:75) spanning the new epitope conjugated to keyhole limpet hemocyanin (KLH) and formulated with GM-CSF.

Mutation-Derived Cancer Neoepitopes

Tumors contain a large number of mutations, ranging from tens to hundreds of somatic nonsynonymous mutations (collectively referred to as "mutanome"), that are unique to the tumor and not present in normal cells (Vogetstein B et al., (2013) Science, 339, 1546). These mutations create novel B and T cell epitopes ("neoepitopes") recognized as "non-self" by the immune system and therefore capable of inducing anti-cancer immune responses. Indeed, tumor-infiltrating T cells (TILs) recognizing the neo-epitopes have been identified in experimentally induced murine tumors and in human tumors, and TILs are being exploited in adoptive T cell transfer therapy (ACT) (Tram E. et al, (2014) Science, 344, 641).

The tumor mutanome also offers the possibility to develop innovative cancer vaccines based on combinations of a selected number of neoepitopes. Such neoepitopes, when formulated with proper adjuvants, can elicit potent anti-cancer immunity. Neoepitope-based vaccines are exquisitely patient-specific ("personalized vaccines") in that each patient carries tumors with mutations largely not shared with tumors from other patients.

The strategy to develop neoepitope-based cancer vaccines envisages: 1) tumor resection and whole genome/transcriptome sequencing, 2) bioinformatics identification of tumor-specific mutations, 3) bioinformatics prediction of T cell neoepitopes generated by the tumor-specific mutations, 4) in silico and/or experimental selection of the most immunogenic neoepitopes, 5) preparation of the patient-specific, neoepitope-based vaccine 6) vaccination of the patient from which the tumor has been removed and sequenced (Tureci O. et al. (2016) Clin. Cancer Res. 22, 1886).

The first-in-human testing of such an approach has been conducted by Sahin and coworkers (Sahim U. et al. (2017) Nature 547, 222-226) in 13 stage III/IV melanoma patients. Ten mutation-derived CD4+ T cells epitopes per patient were selected and all patients received a treatment with a maximum of 20 doses of RNA-based neo-epitope vaccine. Comparison of documented cancer recurrences in treated patients before and after neo-epitope vaccination showed a significant reduction of cumulative recurrent metastatic events ($P<0.0001$), translating into good progression-free survival.

A second milestone paper demonstrating the efficacy of neo-epitope based cancer vaccine has been published by Ott and coworkers (Ott P. A. et al. (2017) Nature 547, 217-221). In a phase I study patients with previously untreated high-risk melanoma (stage IIIB/C and IVM1a/b) were vaccinated with synthetic peptides covering several neo-epitopes in the presence of Hiltonol as adjuvant. Of the six vaccinated patients, four had no recurrence at 25 months post vaccination, and the two of them with recurring disease were treated with Pembrolizumab showing then complete tumor regression.

The proof-of-concept of the efficacy of neoepitope-based personalized vaccines was described in mouse models by Kreiter and coworkers (Kreiter S. et al. (2015) Nature 520, 692-696). These authors analyzed the mutations present in the murine B16F10 and CT26 cancer cell lines, predicted those mutations that generated new, cancer-specific CD4+ and CD8+ T cell epitopes and demonstrated that immunization with synthetic RNA encoding strings of mutation-derived T cell epitopes could inhibit tumor growth in syngeneic mice challenged with B16F10 and CT26 cell lines. In particular, as far as the CT26 cell line/Balb/c mouse model is concerned, these authors reported a list of epitopes that were shown to induce anti-tumor immunity. Among these, five epitopes were included, named M03, M20, M26, M27 and M68 (sequences 12-16). All these five epitopes were used to create FhuD2 fusions.

Fusion of Selected Polypeptides to the C-Terminus of FhuD2

D8-hFAT1 Fusion

Figure 4:
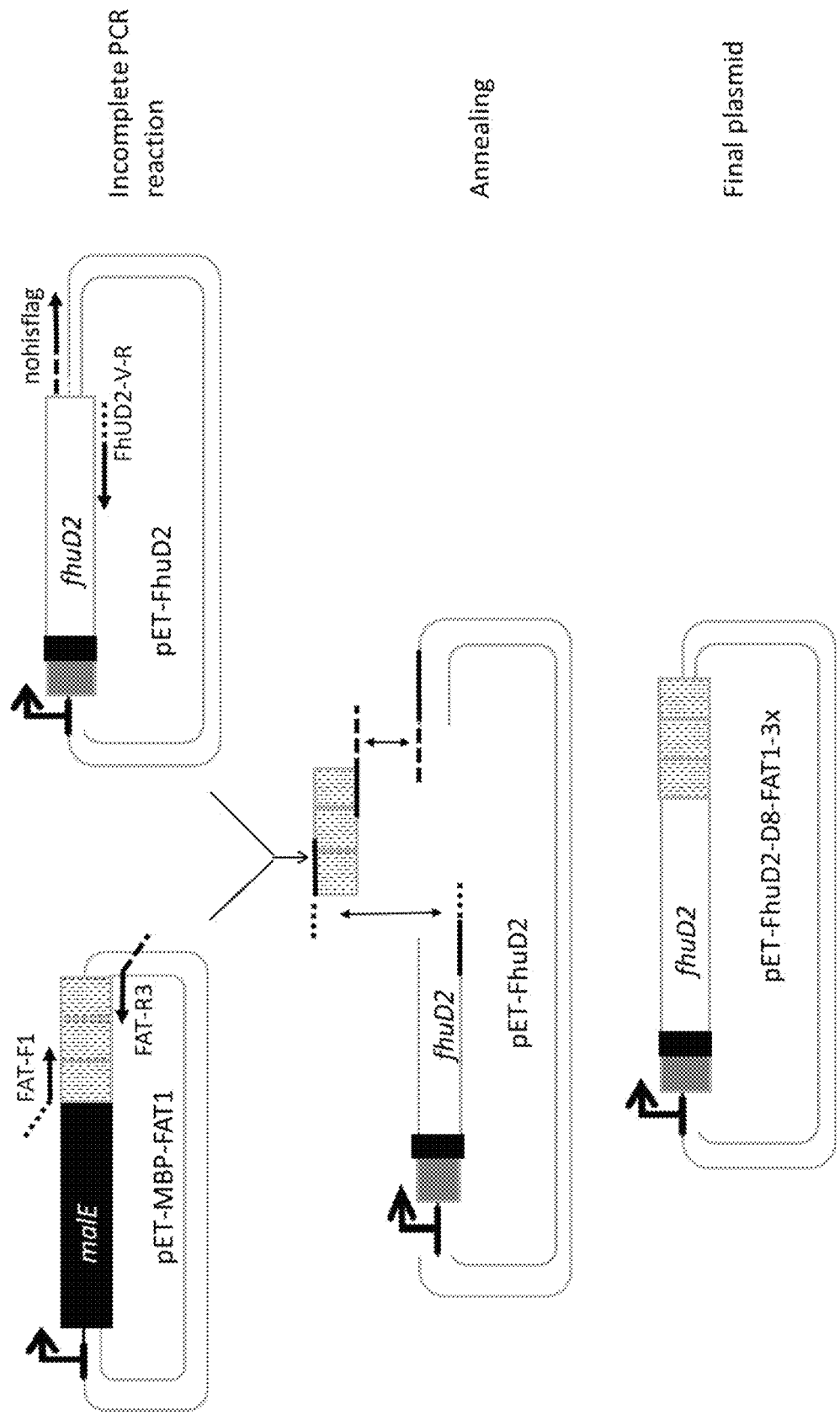
Figure 5:
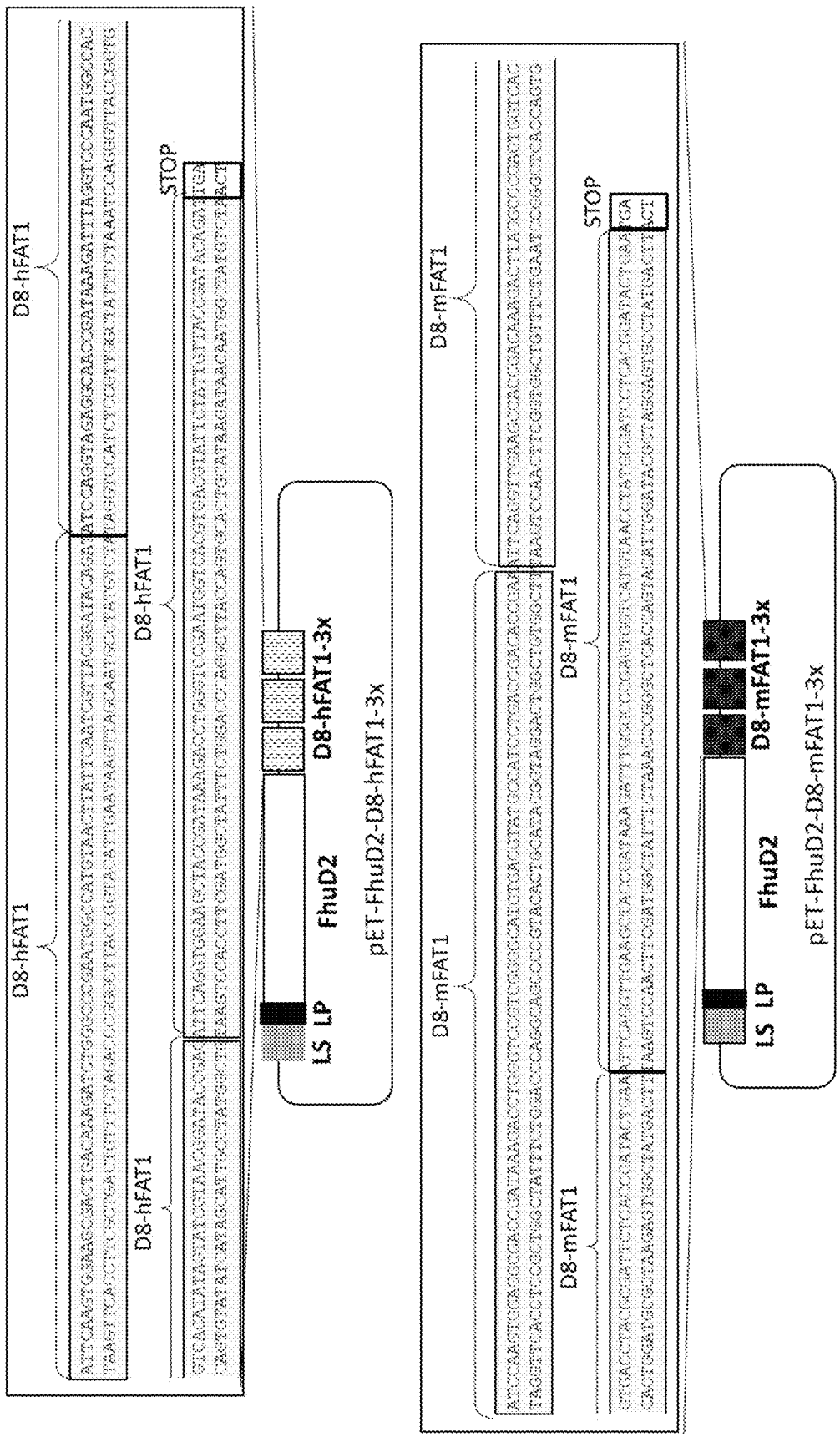

Three copies of D8-hFAT1 were fused to the C-terminus of the FhuD2 lipoprotein following the strategy schematized in FIG. 4. First of all, the sequence encoding three copies of D8-hFAT1 was amplified by PCR from the previously generated pET-MBP-hFAT1 plasmid (patent application EP15167024) with fat1 hu-FhUD2 F/fat1 hu-FhUD2 R primers. These primers were designed to generate extremities complementary to the pET-FhuD2 plasmid. This vector was linearized by PCR amplification using the divergent primers nohis flag F/FhuD2-V-R. Finally, the PCR products were mixed together and used to transform HK-100 competent cells, obtaining pET-FhuD2-D8-hFAT1-3x plasmid (encoding sequence SEQ ID NO:9; amino acid sequence SEQ ID NO:25). The accuracy of the final plasmid was verified by sequence analysis (SEQ ID NO:9 and FIG. 5).

D8-mFAT1 Fusion

Three copies of D8-mFAT1 were fused to the C-terminus of the *S. aureus* FhuD2 lipoprotein (FIG. 4). D8-mFAT1 minigene was constructed, taking into consideration BL21 *E. coli* codon usage, by assembling six complementary oligonucleotides the sequence of which is reported in Table 1 and the assembled DNA fragment was amplified with primers fat1 ms-FhUD2 F/fat1 ms-FhUD2 R primers. These primers were designed to generate extremities complementary to the pET-FhuD2 plasmid. This vector was linearized by PCR amplification using the divergent primers nohis flag F/FhuD2-V-R. Finally, the PCR products were mixed together and used to transform HK-100 competent cells, obtaining plasmids pET-FhuD2 mFAT1-x3 (encoding sequence SEQ ID NO:10; amino acid sequence SEQ ID NO:26). The accuracy of the final plasmid was verified by sequence analysis (SEQ ID NO:10 and FIG. 5).

EGFR-vIII Fusion

Figure 6:
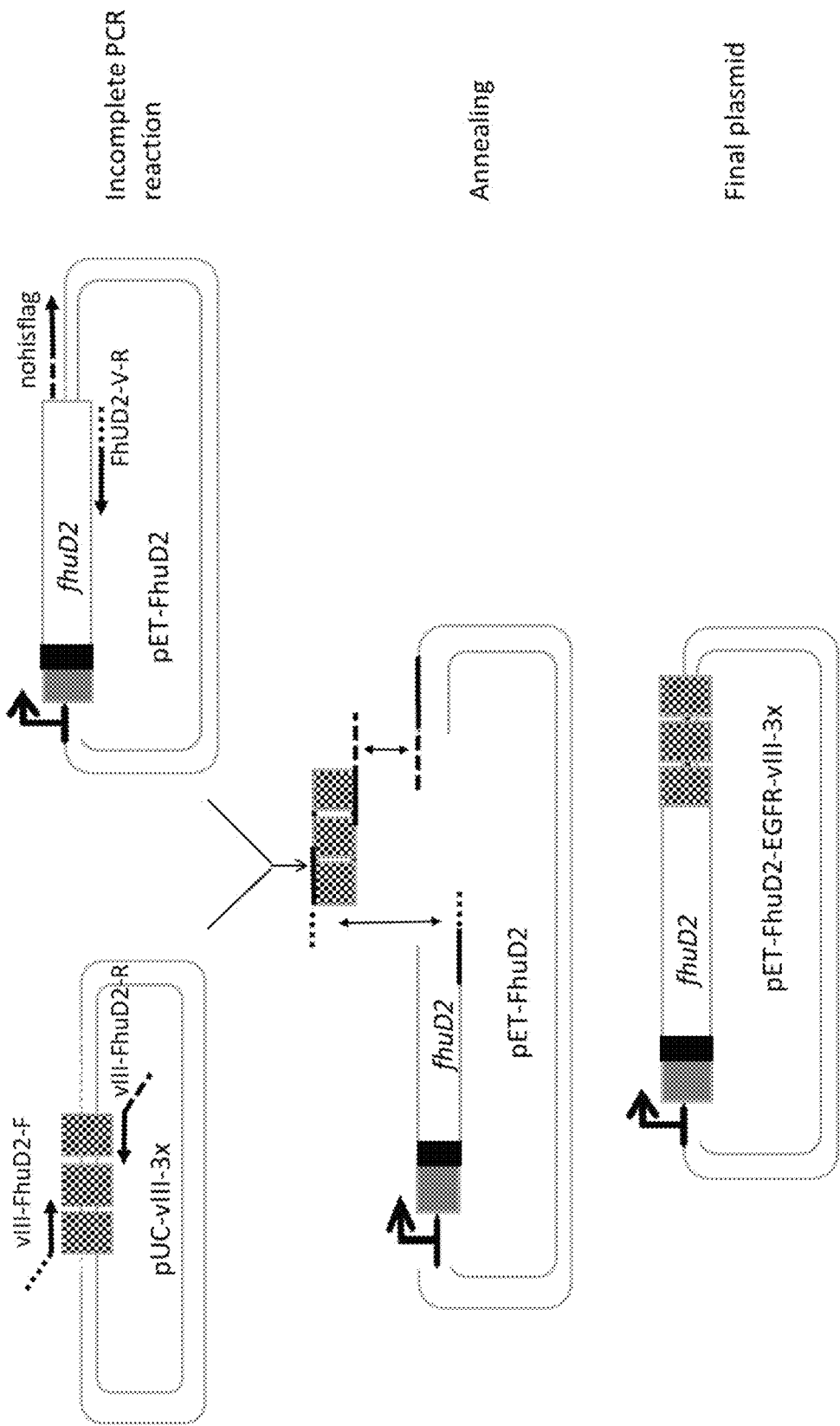
Figure 7:
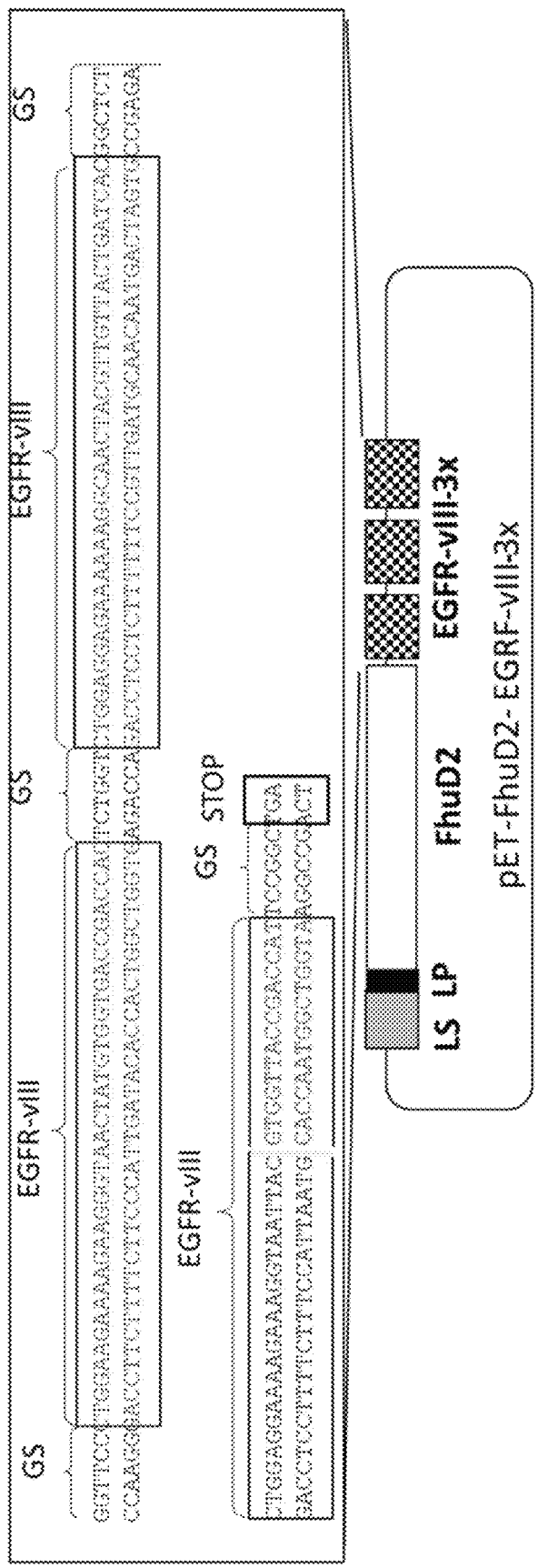

Three copies of the EGFR-vIII peptide were fused to the C-termini of the FhuD2 lipoprotein following the strategy schematized in FIG. 6. In brief, a DNA fragment, named vIII-x3, coding for three copies of vIII separated by the Gly-Ser dipeptide and carrying single stranded 3' EcoRI and BamHI protruding ends was chemically synthesized and cloned in pUC plasmid cut with EcoRI and BamHI. The synthetic DNA and the linear pUC were in vitro ligated and the ligation mixture was used to transform *E. coli* competent cells, thus generating plasmid pUC-vIII-x3. Subsequently, the pET-FhuD2 plasmid was PCR amplified using nohisflag/FhuD2-V-R primers (Table 1), while the vIII-x3 insert was PCR-amplified from pUC-vIII-x3 using primers VIII-FhuD2 F/VIII-FhuD2 R. Finally, the PCR products were mixed together and used to transform HK-100 competent cells, obtaining pET-FhuD2 EGFR-vIII-x3 plasmid (encoding sequence SEQ ID NO:11; amino acid sequence SEQ ID NO:27). The accuracy of the final plasmid was verified by sequence analysis (SEQ ID NO:11 and FIG. 7).

FhuD2 Fusions Carrying Mutation-Derived Cancer Neoepitopes

Figure 8:
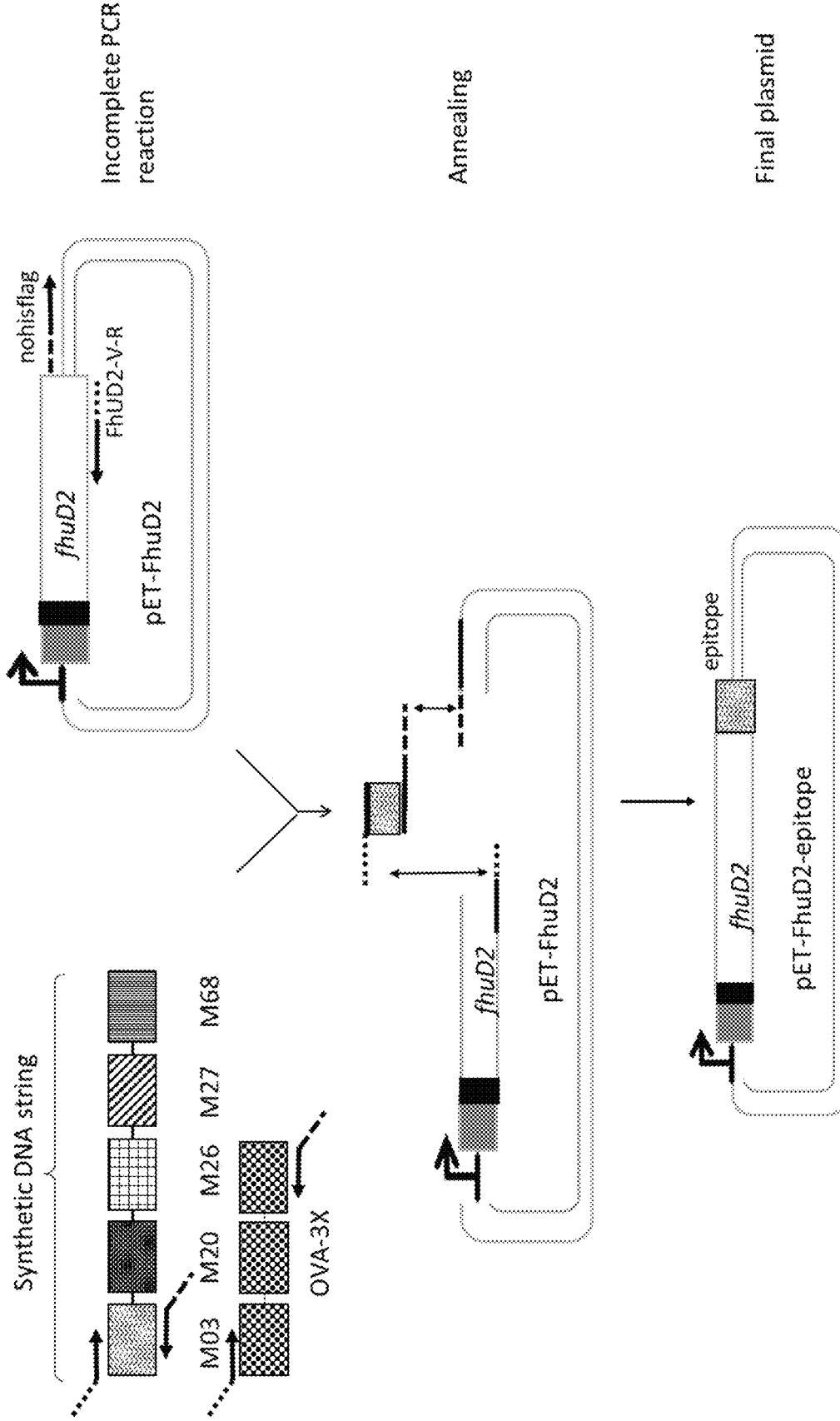

M03, M20, M26, M27 and M68 polypeptides were fused to the C-terminus of the FhuD2 protein as schematically depicted in FIG. 8.

Figure 9:
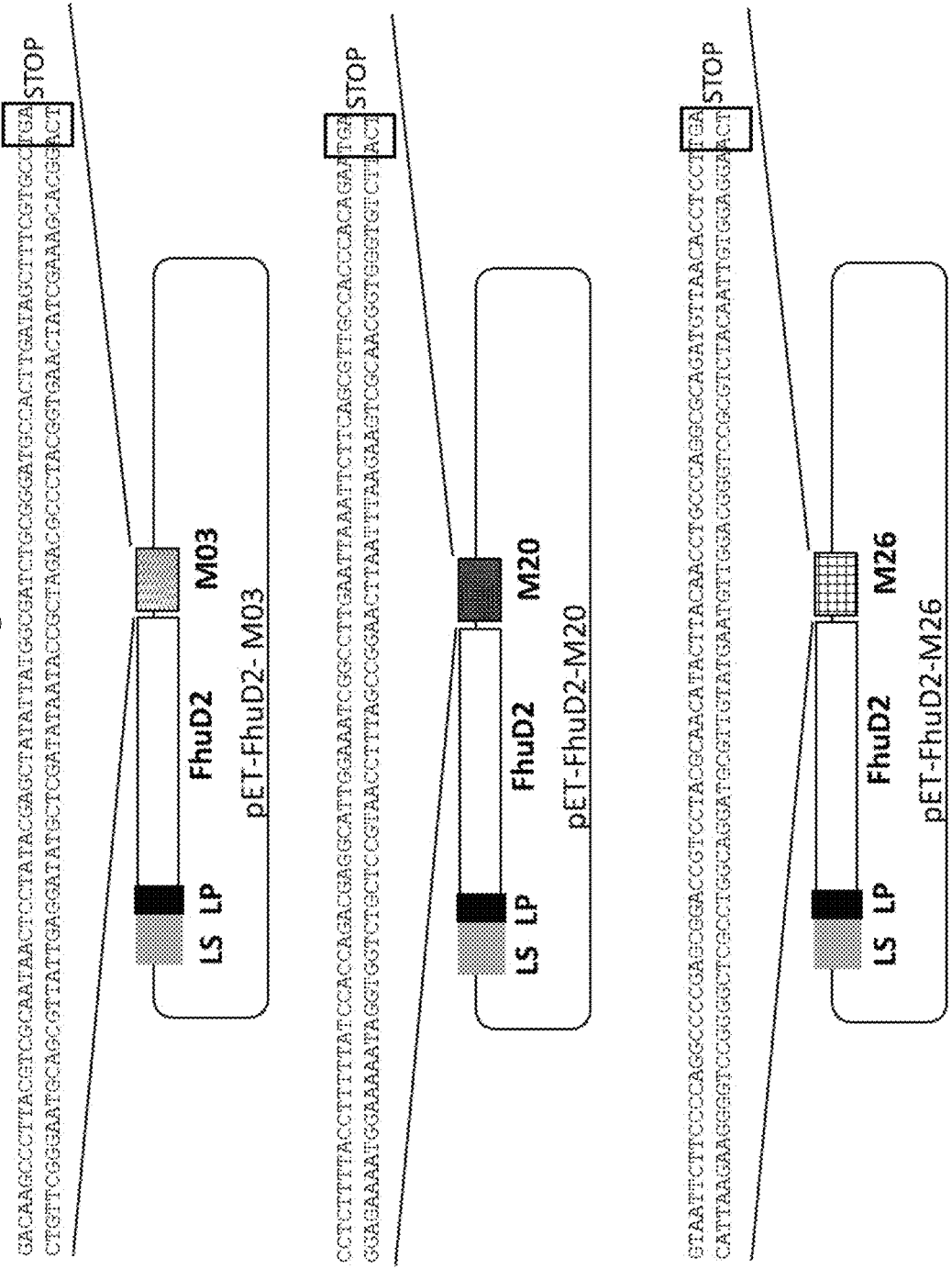
Figure 10:
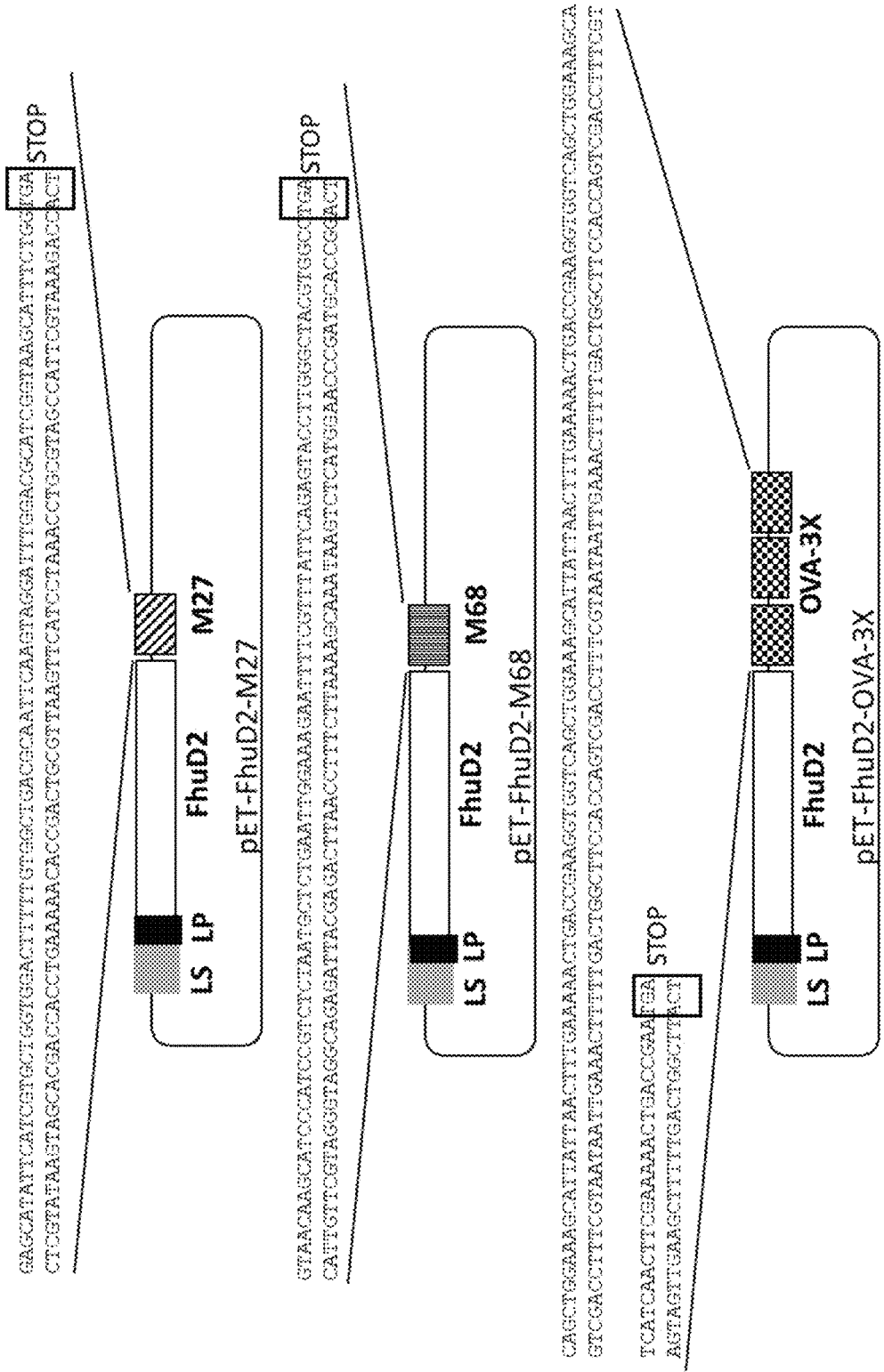

A DNA fragment coding for a single copy of each epitope (M03, M20, M26, M27, M68) was chemically synthetized as a synthetic DNA string (Thermo Fisher). The sequence coding for each synthetic epitope was ligated to the 3' end of the full length fhuD2 gene using the polymerase incomplete primer extension (PIPE) cloning method. Briefly, pET-FhuD2 plasmid was linearized by PCR using primers nohisflag/Lpp-R plasmid (Table), while the each of the M03, M20, M26, M27, M68 coding sequence was PCR amplified from the synthetic DNA string using primers M03F/M03R, M20F/M20R, M26F/M26R, M27F/M27R, M68F/M68R, respectively (Table 1) to make their extremities complementary to pET-FhuD2 linearized plasmid. Finally, each PCR product derived from amplification of M03, M20, M26, M27 and M68 epitopes was mixed together with the linearized pET-FhuD2 plasmid and used to transform HK-100 competent cells, obtaining pET-FhuD2-M03 (encoding sequence SEQ ID NO:12; amino acid sequence SEQ ID NO:28), pET-FhuD2-M20 (encoding sequence SEQ ID NO:13; amino acid sequence SEQ ID NO:29), pET-FhuD2-M26 (encoding sequence SEQ ID NO:14; amino acid sequence SEQ ID NO:30), pET-FhuD2-M27 (encoding sequence SEQ ID NO:15; amino acid sequence SEQ ID NO:31), pET-FhuD2-M68 (encoding sequence SEQ ID NO:16; amino acid sequence SEQ ID NO:32) plasmids. The correctness of the cloning was verified by sequence analysis (SEQ ID NOs: 12, 13, 14, 15, 16 and FIGS. 9-10).

$OVA_{257-264}$ Fusion

Three copies of $OVA_{257-264}$ were fused to the C-terminus of the FhuD2 protein as schematically depicted in FIG. 8.

A DNA fragment coding for encoding three copies of the $OVA_{257-264}$ with flanking sequences and separated by glycine-glycine spacer was chemically synthetized as a synthetic DNA string (Thermo Fisher). The sequence was ligated to the 3' end of the full length fhuD2 gene using the polymerase incomplete primer extension (PIPE) cloning method. Briefly, pET-FhuD2 plasmid was linearized by PCR using primers nohisflag/Lpp-R plasmid (Table), while the three copies of $OVA_{257-264}$ coding sequence was PCR amplified from the synthetic DNA string using primers OVA-FhuD2 F and OVA-FhuD2 R (Table 1) to make their extremities complementary to pET-FhuD2 linearized plasmid. Finally, PCR product derived from amplification of three copies of $OVA_{257-264}$ epitope was mixed together with the linearized pET-FhuD2 plasmid and used to transform HK-100 competent cells, obtaining pET-FhuD2-OVA-3X (encoding sequence SEQ ID NO:77, amino acid sequence SEQ ID NO:78). The correctness of the cloning was verified by sequence analysis (SEQ ID NO:77 and FIG. 10).

Expression of FhuD2 Fusion Proteins

Figure 11:
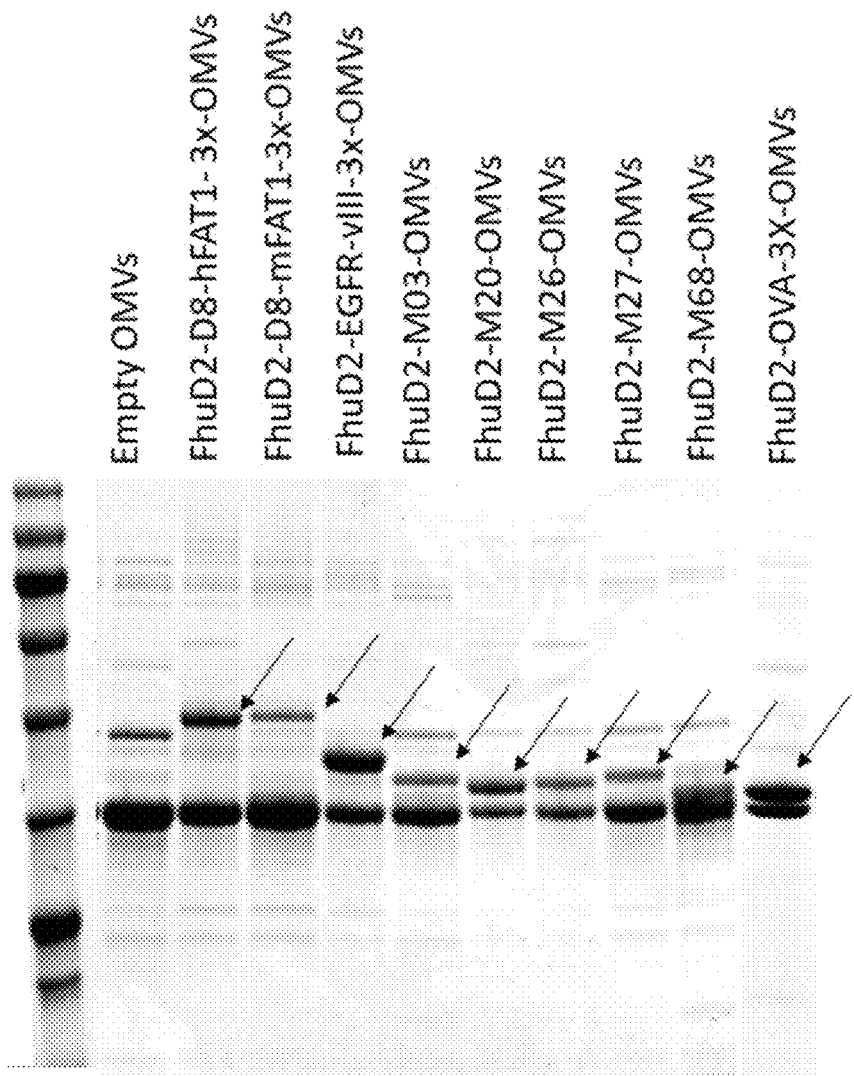
Figure 12:
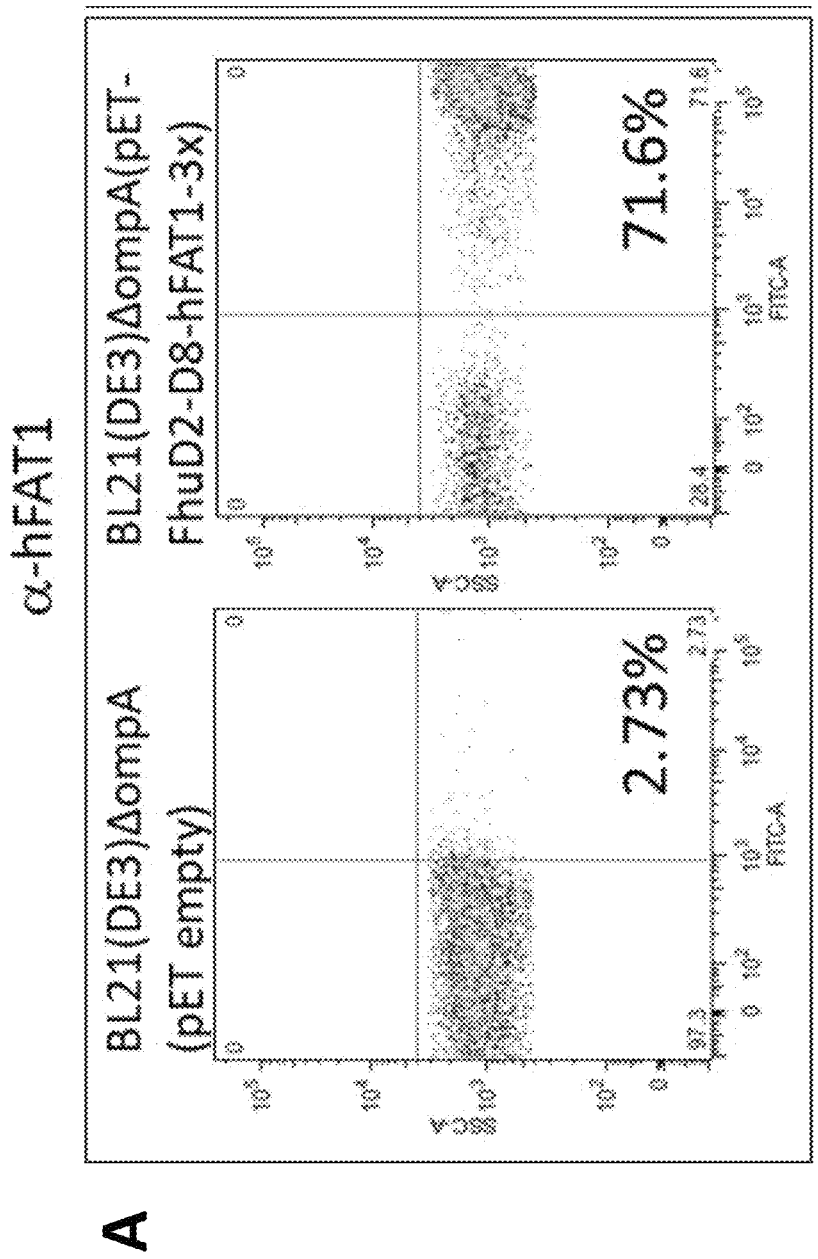
Figure 12:
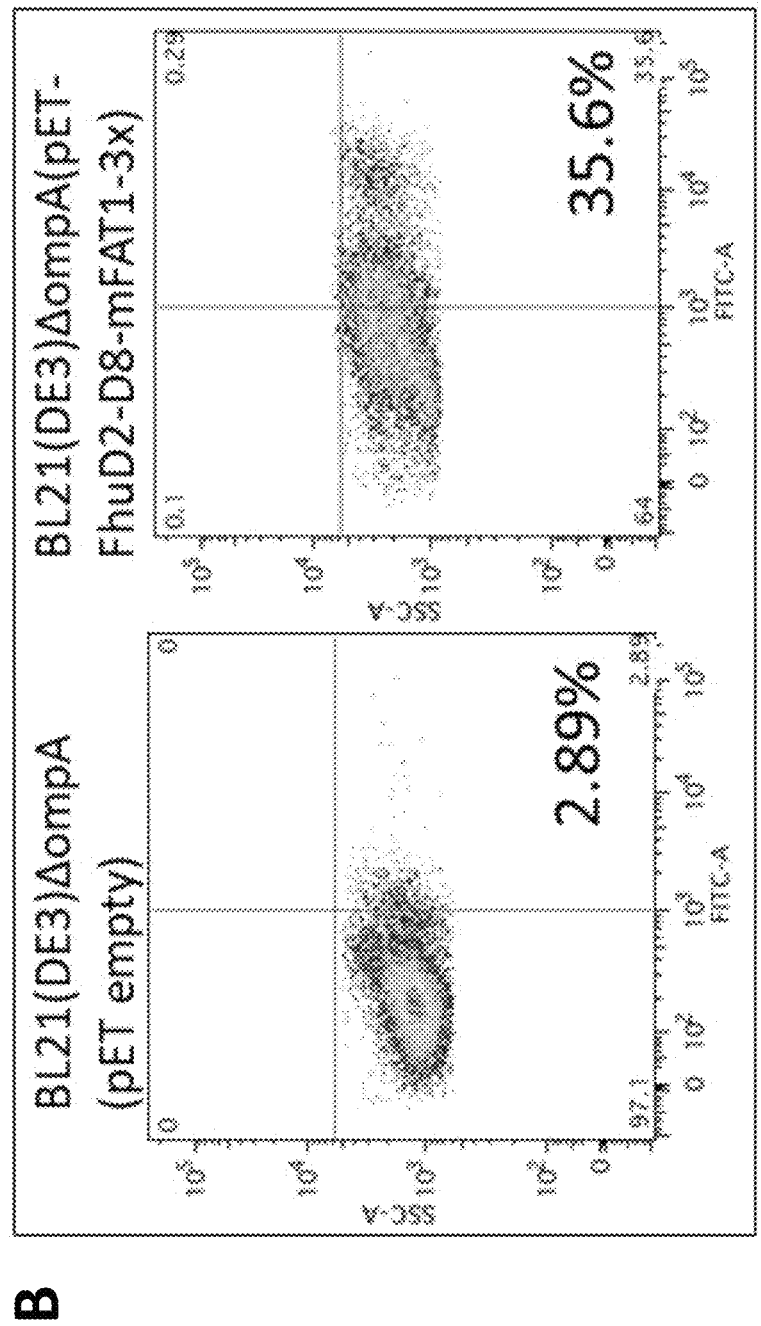
Figure 12:
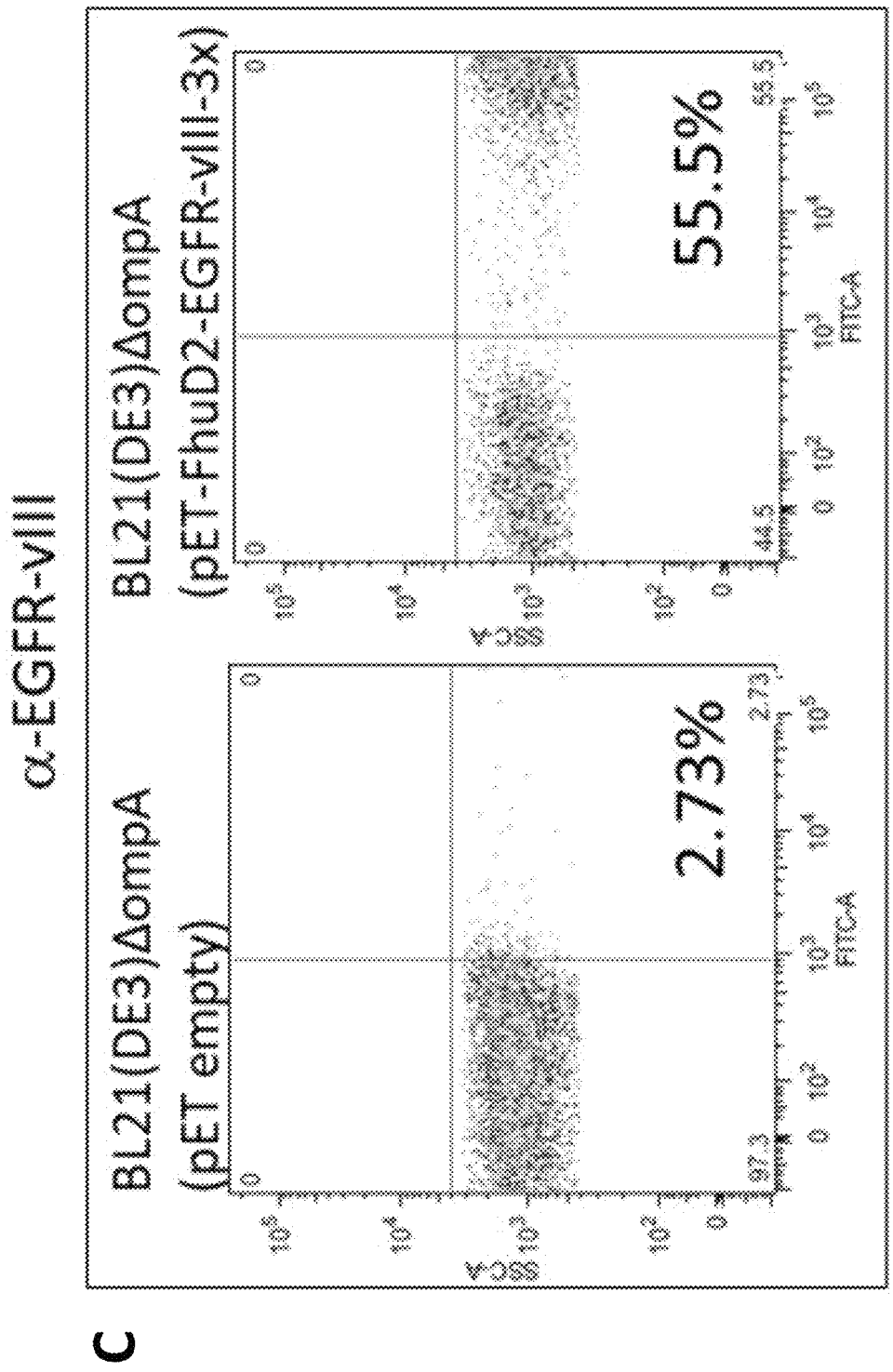
Figure 12:
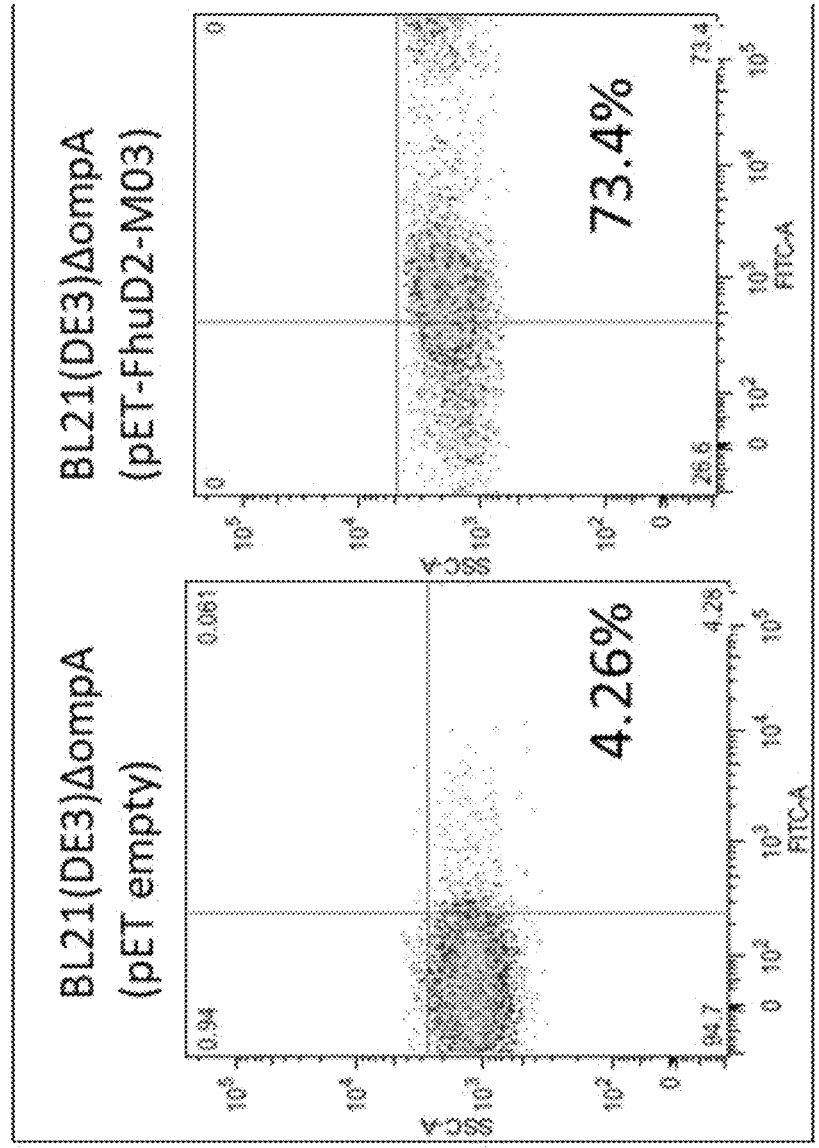
Figure 12:
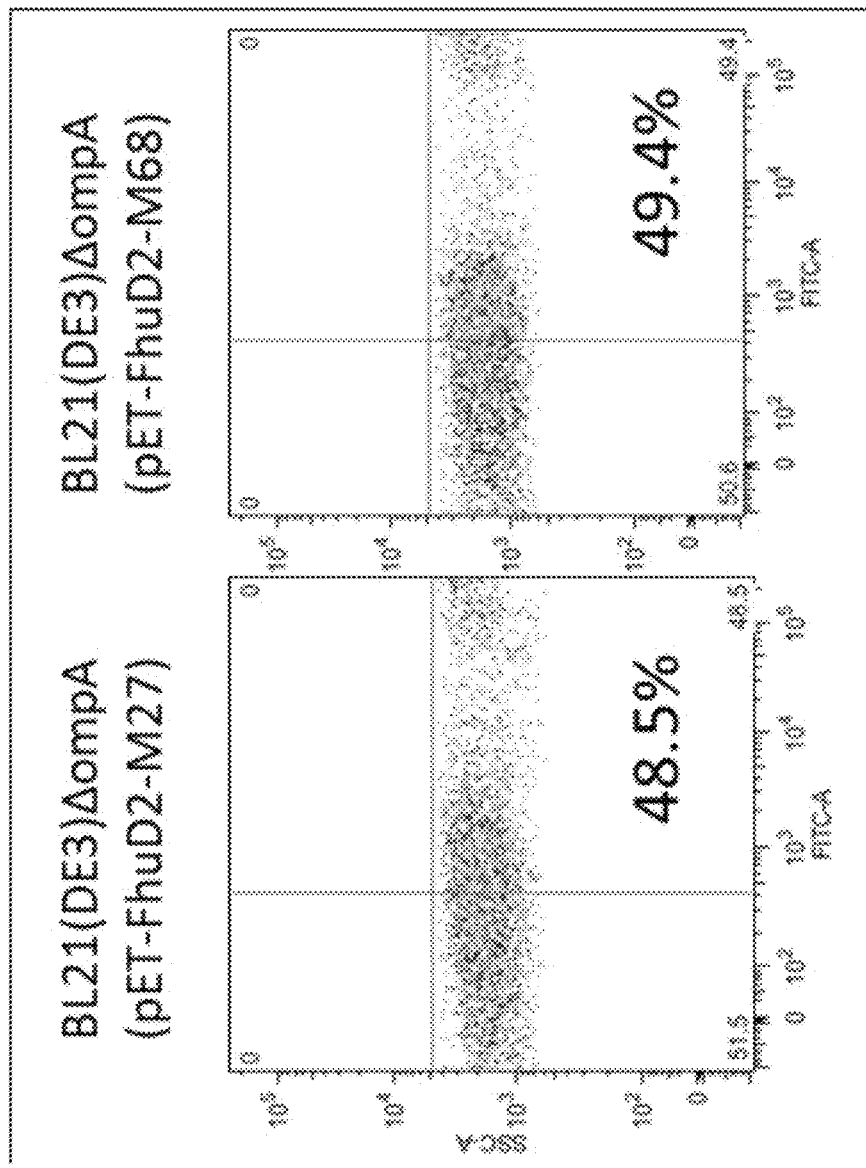

To investigate how the different epitopes fused to the FhuD2 protein were expressed in *E. coli* and whether they could reach the membrane and OMV compartments, the recombinant plasmids encoding the selected epitopes fused to the FhuD2 lipoprotein were used to transform *E. coli* BL21(DE3)ΔompA strain. Bacteria were grown in LB medium and when the cultures reached an $OD_{600}$ value of 0.5, IPTG was added at 0.1 mM final concentration. After two additional hours of growth at 37° C., vesicles were purified from culture supernatants by using ultrafiltration coupled to ultracentrifugation. More specifically, OMVs were collected from culture supernatants by filtration through a 0.22 μm pore size filter (Millipore) and by high-speed centrifugation (200,000×g for 2 hours). Pellets containing OMVs were finally suspended in PBS. The presence of the epitopes fused to the FhuD2 protein in total bacterial lysates and OMV preparations from BL21(DE3) ΔompA derivative strain was analyzed by SDS-PAGE. As shown in FIG. 11, all FhuD2 fusion proteins could be visualized by Coomassie Blue staining and compartmentalized in OMVs. Next, the localization of the FhuD2 fusion proteins was evaluated by flow cytometry. To this aim, recombinant *E. coli* strains BL21(DE3)ΔompA(pET-FhuD2-EGRF-vIII-3x), BL21(DE3)ΔompA(pET-FhuD2-D8-hFAT1-3x), BL21(DE3)ΔompA(pET-FhuD2-D8-mFAT1-3x) BL21(DE3)ΔompA (pET-FhuD2-M03), BL21(DE3)ΔompA(pET-FhuD2-M20), BL21(DE3)ΔompA(pET-FhuD2-M26), BL21(DE3)ΔompA(pET-FhuD2-M27) and BL21(DE3)ΔompA(pET-FhuD2-M68) were grown at 37° C. under agitation. When cultures reached an $OD_{600}$ value of 0.5, IPTG was added at a final concentration of 0.1 mM and bacteria were grown for 2 additional hours. Subsequently, bacteria cells corresponding to those contained in 1 ml culture at $OD_{600}$=1 were collected by centrifugation at 13,000×g for 5 minutes and pellets were re-suspended in 1 ml of PBS containing 1% BSA and subsequently diluted 1:50 in PBS 1% BSA. 50 μl of cell suspensions were then incubated with 50 μl of an appropriate dilution of anti-FhuD2 or anti-EGFR-vIII or anti-hFAT1 or anti-mFAT1 primary antibodies or with 50 μl of PBS containing 1% BSA as negative control. After 1 hour, 100 μl of PBS containing 1% BSA were added and the suspensions were centrifuged at 3,000×g for 10 minutes and supernatants discarded. Pellets were washed with 200 μl of PBS containing 1% BSA and bacteria subsequently incubated for 30 minutes on ice with secondary antibodies conjugated with FITC (Alexa flour488, Life Technology) added at a final dilution of 1:2,000. Finally, after 2 washing steps, pellets were re-suspended in 200 μl of PBS and analyzed with FACS CANTOII (BD) evaluating collected data with FlowJo software. As shown in FIG. 12, in the presence of anti-FhuD2 antibodies (M03, M20, M26, M27, M68 fusions) or in the presence of antibodies against mFAT1 (FhuD2-D8-mFAT1-3x fusion), hFAT1 (FhuD2-D8-hFAT1-3x fusion) and EGFRvIII (FhuD2-EGFR-vIII-3x fusion), a shift in fluorescence intensity was observed in a substantial fraction of bacterial cells, indicating that all fusions proteins were exposed to the extracellular compartment of *E. coli* BL21 (DE3)ΔompA strain.

Engineered OMVs Carrying Recombinant FhuD2-EGFR-vIII-3x, FhuD2-D8-hFAT1-3x and FhuD2-D8-mFAT1-3x Fusion Proteins Induce Epitope-Specific Antibodies Titers in Immunized Mice To test whether OMVs purified from recombinant strains expressing FhuD2-EGFR-vIII-3x, FhuD2-D8-hFAT1-3x and FhuD2-D8-mFAT1-3x were capable of inducing epitope-specific antibody responses, CD1 mice were i.p. immunized three times at two-week intervals with 20 μg of OMVs formulated in PBS. Blood samples were collected seven days after the third dose (post 3) administration and anti-EGFR-vIII, anti-D8-hFAT1 and anti-D8-mFAT1 IgGs were detected by using plates coated in each well with 0.5 μg of synthetic EGFR-vIII, D8-hFAT1 and D8-mFAT1 peptides, respectively. Serum deriving from mice immunized with empty OMVs was used as negative control. More specifically, coating was carried out by incubating plates overnight at 4° C. with 100 μl of synthetic peptides (5 μg/ml). Subsequently, wells were washed three times with PBST (0.05% Tween 20 in PBS, pH 7.4), incubated with 100 μl of 1% BSA in PBS for 1 h at room temperature and washed again three times with PBST. Serial dilutions of serum samples in PBST containing 1% BSA were added to the plates, incubated 2 h at 37° C., and washed three times with PBST. Then 100 μl/well of 1:2.000 diluted, alkaline phosphatase-conjugated goat anti-mouse IgGs were added and left for 1 h at 37° C. After three PBST washes, bound alkaline phosphatase-conjugated antibodies were detected by adding 100 μl/well of 3 mg/ml para-nitrophenyl-phosphate disodium hexahydrate (Sigma-Aldrich) in 1M diethanolamine buffer (pH 9.8). After 30-minute incubation at room temperature, the reaction was stopped with 100 μl 7% EDTA and substrate hydrolysis was analyzed at 405 nm in a microplate spectrophotometer.

Figure 13:
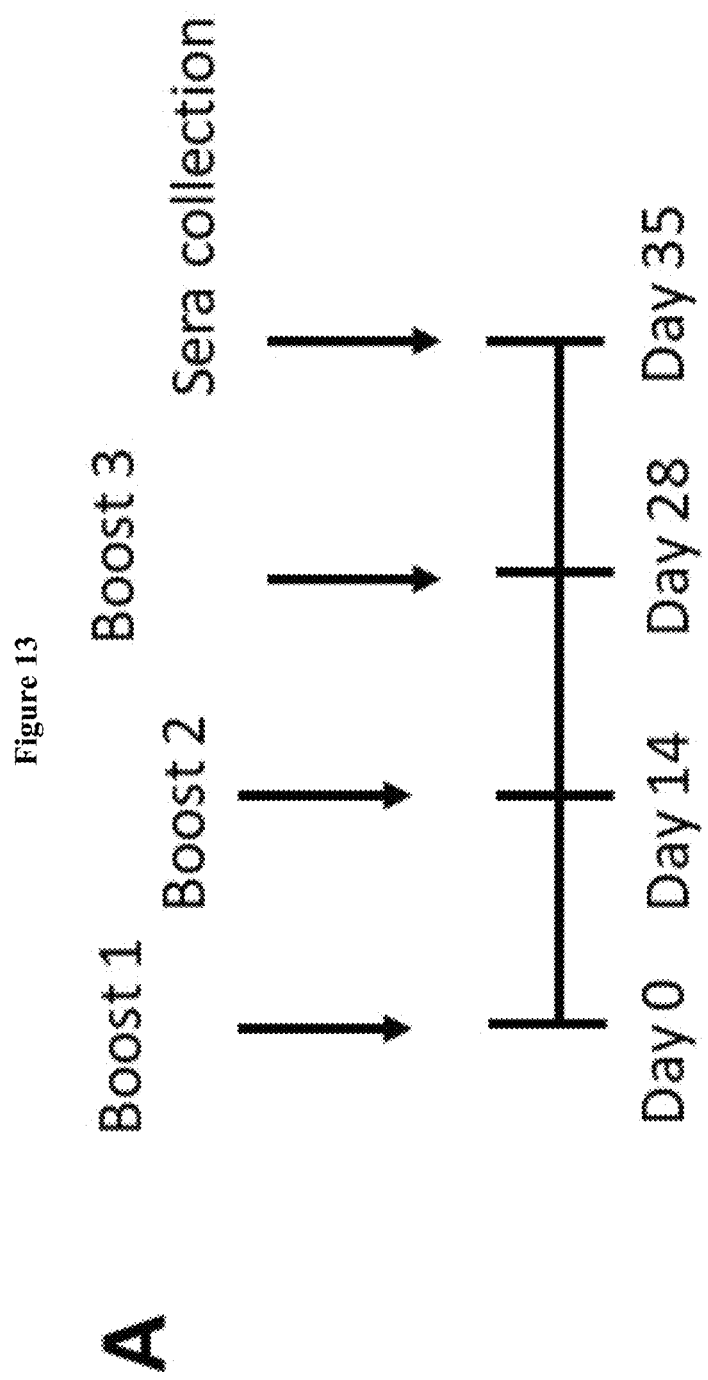
Figure 13:
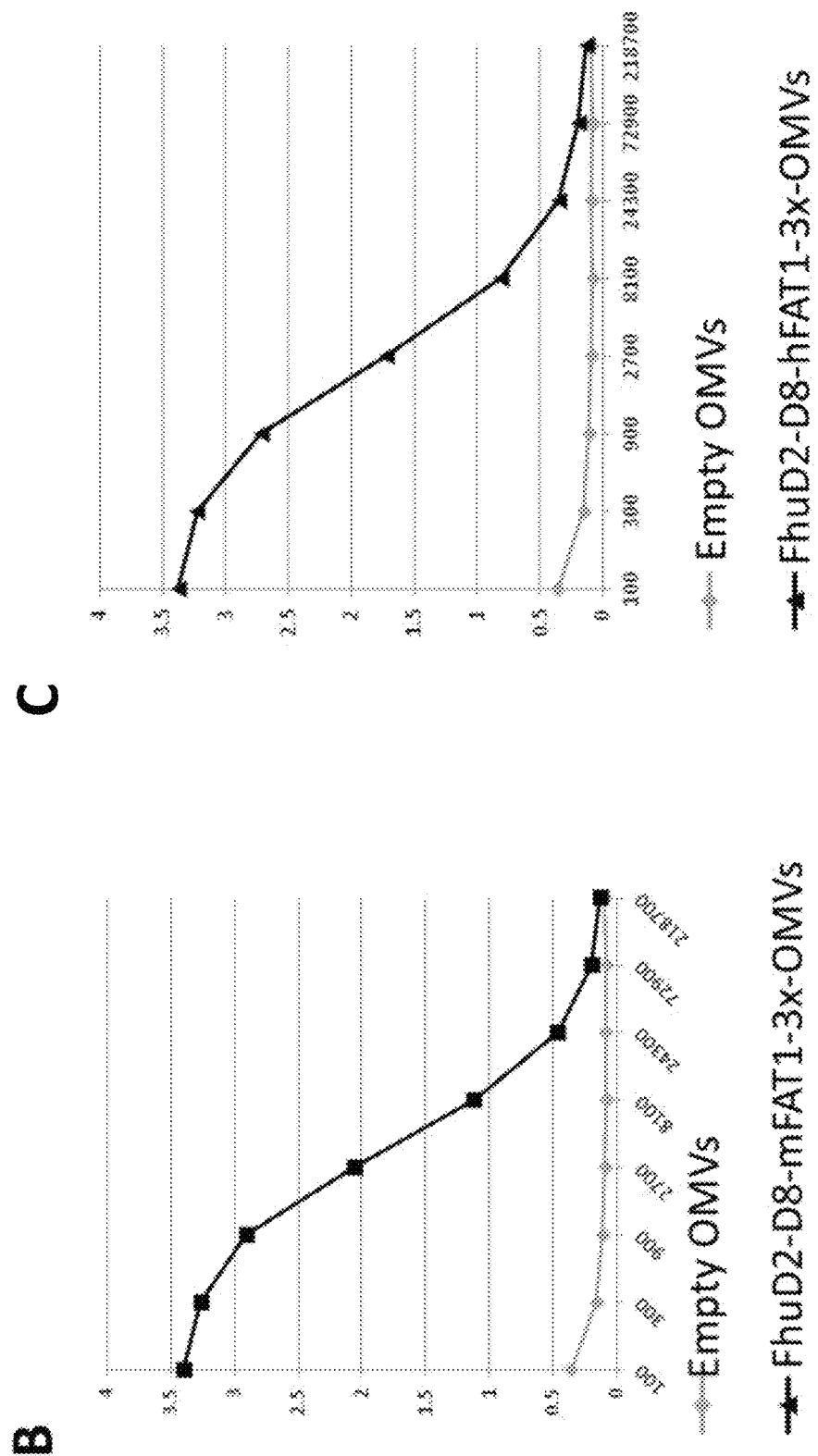
Figure 13:
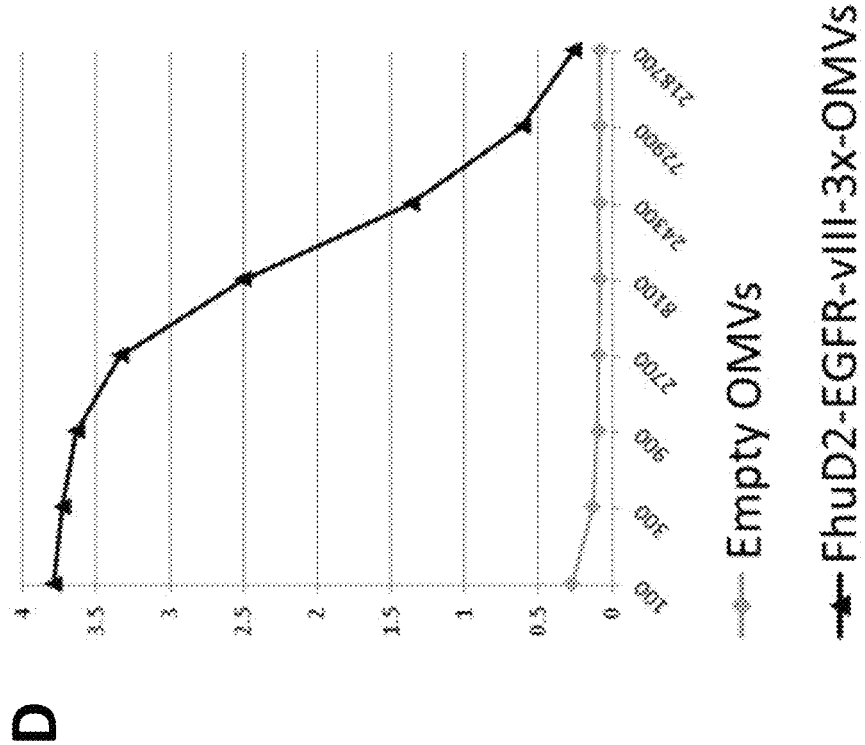

As shown in FIG. 13, OMVs carrying FhuD2-EGFR-vIII-3x, FhuD2-D8-hFAT1-3x and FhuD2-D8-mFAT1-3x fusion proteins were able to induce epitope-specific IgG titers in immunized mice.

Engineered OMVs with OVA Epitope and Cancer Neo-Epitopes Fused to FhuD2 Induce Specific CD4⁻/CD8⁺ T Cells.

To test whether OMVs carrying three copies of $OVA_{257-264}$ peptide and CD4+ or CD8+ cancer neo-epitopes fused to FhuD2 were capable to induce specific T cell responses, OMVs decorated with FhuD2-OVA-3X, FhuD2-M03, FhuD2-M20, FhuD2-M26, FhuD2-M27 and FhuD2-M68 were used to immunize Balb/c mice. In particular, immunization was carried out using the i.p. or s.c. route at day 0 and 7 (FIG. 14 A) with 20 μg OMV preparation purified from BL21(DE3)ΔompA (pET-FhuD2-OVA-3X) or 4 μg of each OMV preparation purified from BL21(DE3) ΔompA (pET-FhuD2-M03), BL21(DE3)ΔompA(pET-FhuD2-M20), BL21(DE3)ΔompA(pET-FhuD2-M26), BL21(DE3)ΔompA(pET-FhuD2-M27) and BL21(DE3) ΔompA(pET-FhuD2-M68) recombinant strains. At day 12 mice were sacrificed and spleens collected in 5 ml DMEM high glucose (GIBCO). Spleens were then homogenized and splenocytes filtered using a Cell Strainer 70 μm. After centrifugation at 100×g for 7 minutes, splenocytes were re-suspended in PBS and aliquoted in a 96 well plate at a concentration of 1×10⁶ cells per well. Then, cells were stimulated with 10 μg/ml of an unrelated peptide (negative control), or 10 μg/ml each of CT26-M03, CT26-M20, CT26-M26, CT26-M27 and CT26-M68 synthetic peptide mix. As positive control, cells were stimulated with phorbol 12-myristate 13-acetate (PMA, 5 ng/ml) and Ionomycin (1 μg/ml). After 2 hours of stimulation at room temperature, GolgiStop (Beckton Dickenson (BD)) was added to each well and cells incubated for 2 h at 37° C. After 2 washes with PBS, NearIRDead cell staining reaction mixture (Thermo Fisher) was incubated with the splenocytes for 20 minutes at room temperature in the dark. After two washes with PBS and permeabilization and fixing with Cytofix/Cytoperm (BD) using the manufacturer's protocol, splenocytes were stained with a mix of the following fluorescent-labelled antibodies: Anti-CD3-APC (BioLegend), Anti-CD4-BV510 (BioLegend), anti-CD8-PECF594 (BD) and anti-IFNγ BV785 (BioLegend). Samples were analyzed on a BD FACS LSR II using FlowJo software.

Figure 14:
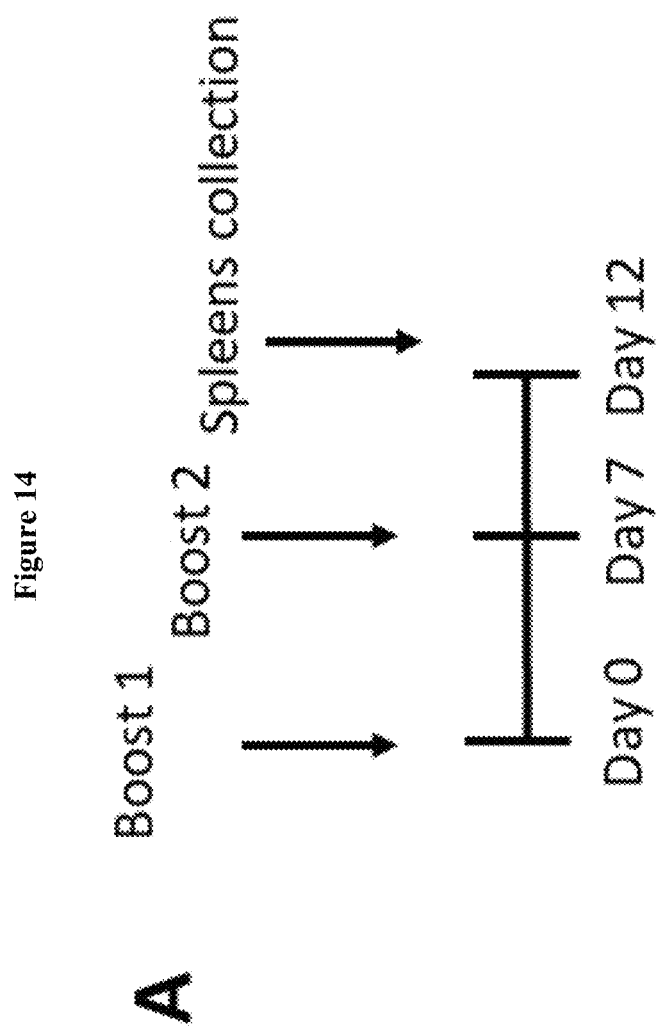
Figure 14:
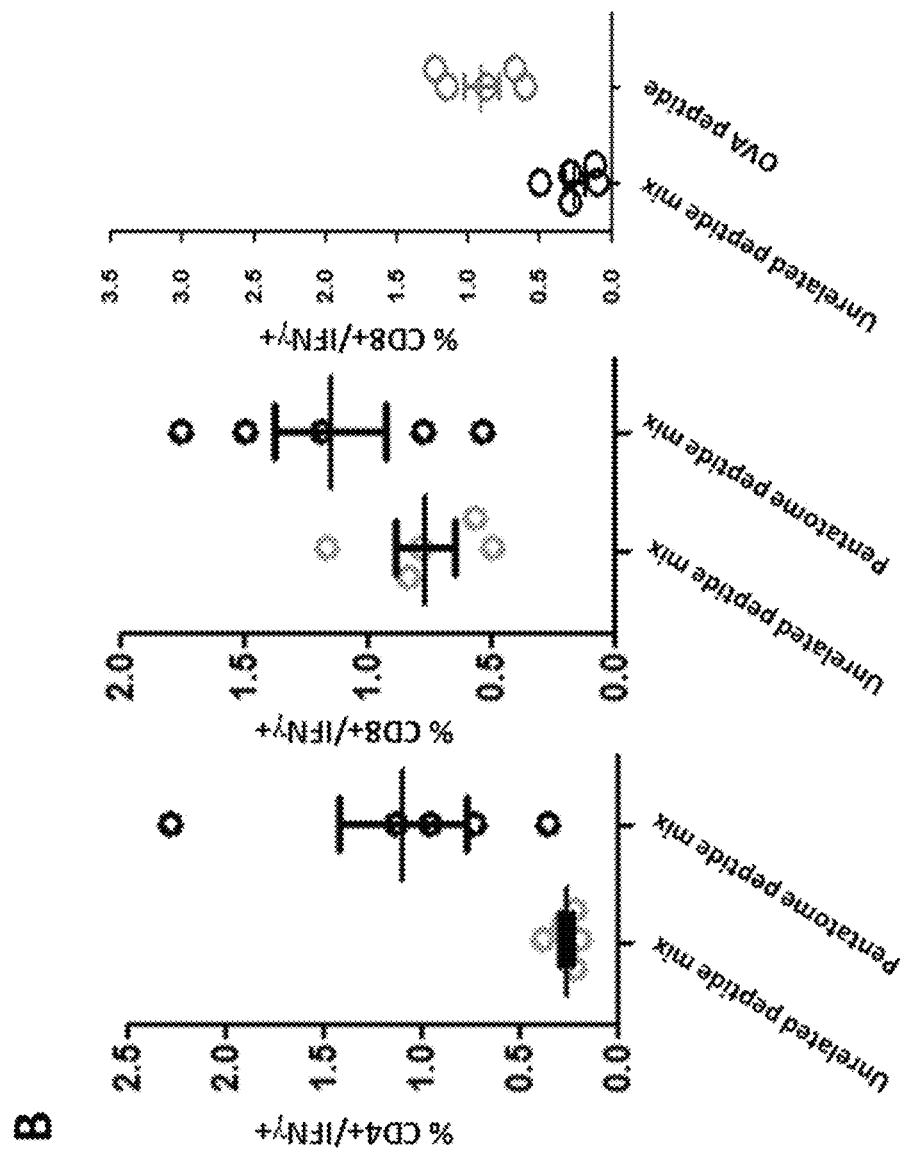
Figure 14:
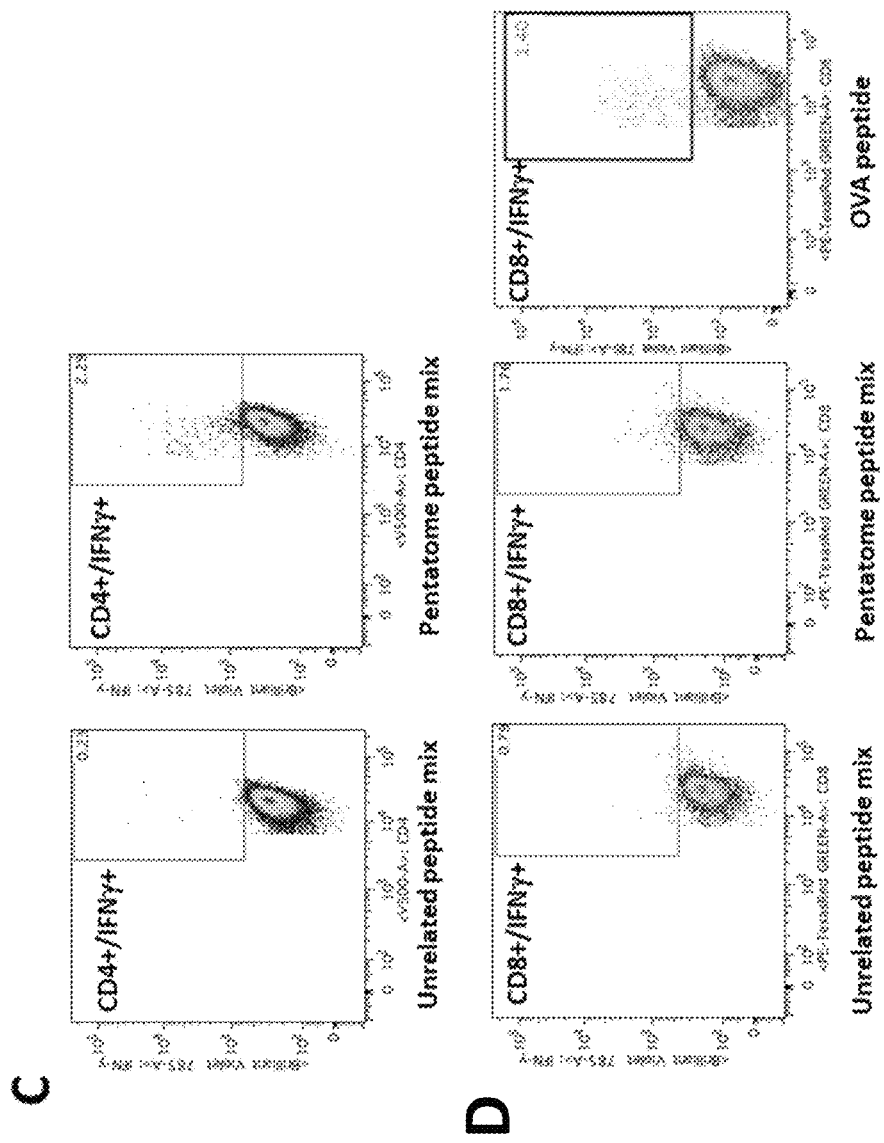

As shown in FIG. 14, the mixture of 4 μg each OMVs carrying FhuD2-M03, FhuD2-M20, FhuD2-M26, FhuD2-M27 and FhuD2-M68 fusion proteins was able to induce a specific T cell response in immunized mice. Similarly, OMVs carrying FhuD2-OVA-3X was able to induce a CD8+ T cell response specific against OVA peptide in immunized mice.

Immunization with FhuD2-mFAT1-3x-OMVs Protects Mice Against CT26 Tumor Challenge Having demonstrated that the immunization with FhuD2-mFAT1-3x-decorated OMVs elicited anti-mFAT1 antibodies in mice, we verified whether such immunization could also protect BALB/c mice from the challenge with the syngeneic CT26 cancer cell line expressing FAT1 on its surface.

Figure 15:
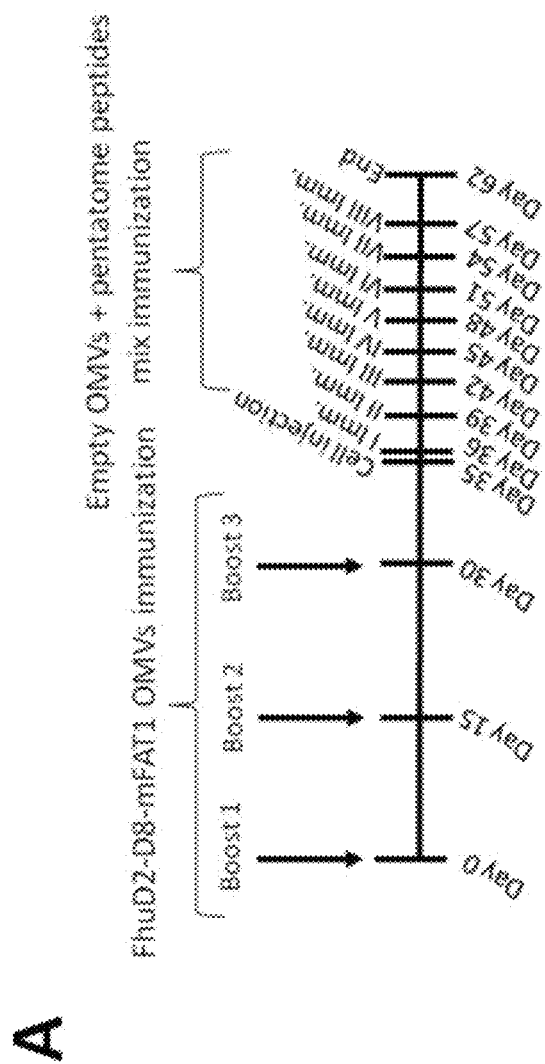
Figure 15:
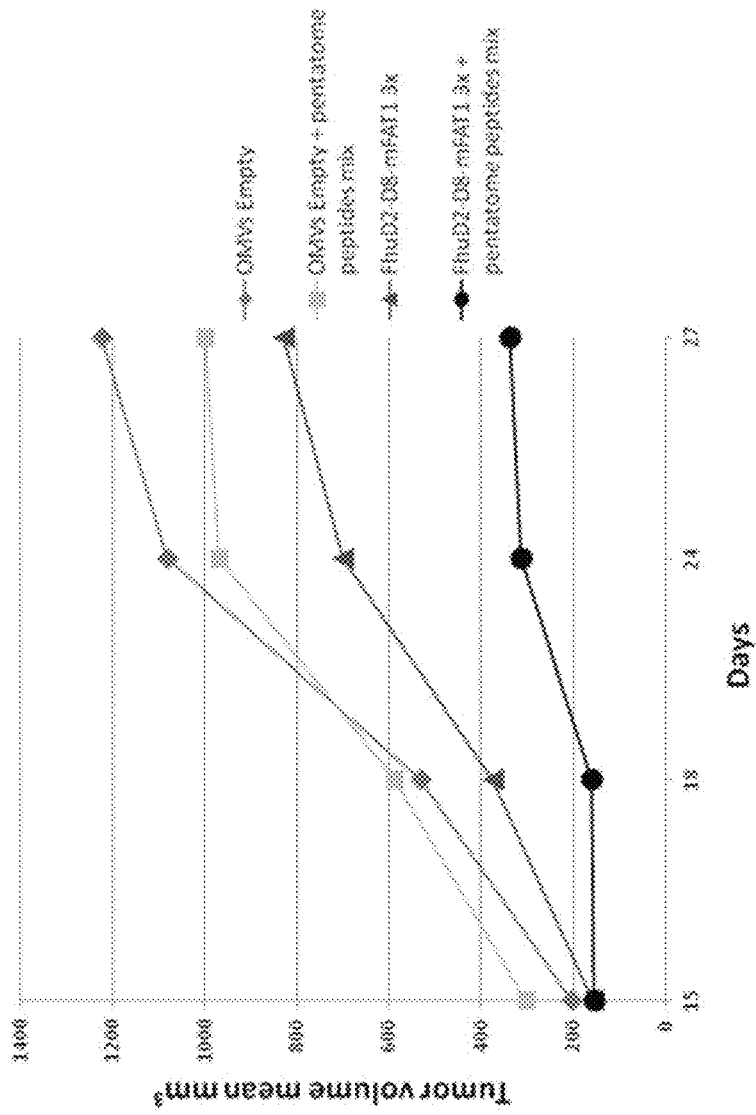
Figure 15:
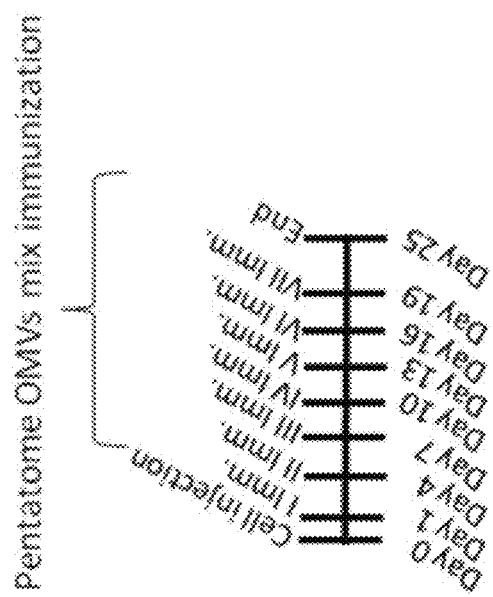

To this aim, two groups of six Balb/c mice were i.p. immunized three times every two weeks with either 20 μg/dose of "empty" OMVs (Gr1) or with 20 μg/dose of FhuD2-mFAT1 OMVs (Gr3). A week after the last immunization, 2.5×10⁵ CT26 cells were injected s.c. in each mouse and tumor growth was followed over a period of 27 days by measuring the tumor size with a caliper. As shown in FIG. 15 (B), immunization with FhuD2-mFAT1-3x-OMVs reduced tumor growth in a statistically significant manner (approximately 50% protection).

We also analyzed whether the protective activity of FhuD2-D8-mFAT1-3x-OMV immunization could be potentiated by a subsequent vaccination with vesicles carrying mutation-derived neoepitopes. To this aim, two groups of Balb/c mice were first i.p. immunized three times every two weeks with either 20 µg/dose of "empty" OMVs (Gr2) or with 20 µg/dose of FhuD2-mFAT1-3x-OMVs (Gr4). A week after the last immunization, $2.5 \times 10^5$ CT26 cells were injected s.c. in each mouse. The following day mice were immunized with 20 µg of "Empty" OMVs absorbed with 20 µg each of M03, M20, M26, M27 and M68 synthetic peptides mix (FIG. 15). Immunization with peptide-absorbed vesicles was repeated every three days for a total of six injections. Tumor volume was measured as described above. As shown in FIG. 15 the combination of FhuD2-mFAT1-3x-OMV the immunization with neoepitope-absorbed OMVs synergized to give a protection which was superior, in a statistically significant manner, to the protection observed with FhuD2-D8-mFAT1-3x-OMV alone, or with neoepitope-absorbed OMVs alone.

Immunization with FhuD2-M03, FhuD2-M20, FhuD2-M26, FhuD2-M27 and FhuD2-M68 OMVs Protects Mice Against CT26 Tumor Challenge Having demonstrated that the immunization with the mixture of OMVs decorated with FhuD2-M03, FhuD2-M20, FhuD2-M26, FhuD2-M27 and FhuD2-M68 fusions elicited specific T cells against the five epitopes, we verified whether such immunization could also protect BALB/c mice from the challenge with the syngeneic CT26 cancer cell line expressing the five neo-epitopes.

To this aim, two groups of six Balb/c mice were challenged with $2.5 \times 10^5$ CT26 cells injected s.c. in each mouse and tumor growth was followed over a period of 21 days by measuring the tumor size with a caliper. The day after the cell injection, mice were immunized with either 20 µg/dose of "empty" OMVs (Gr1) or with 20 µg/dose of a mixture of OMVs each decorated with one of the five fusion proteins FhuD2-M03, FhuD2-M20, FhuD2-M26, FhuD2-M27 and FhuD2-M68 OMVs (4 µg of each engineered OMV) (Gr2). The same immunization was repeated every three days. As shown in FIG. 15 (D), immunization with the mixture of engineered OMVs reduced tumor growth in a statistically significant manner.

TABLE 1

Oligonucleotide primers used for plasmids and genes preparation

| NAME | SEQUENCE |
|---|---|
| pET-FhuD2, pET-Hla, pET-LukE and pET-Spa plasmids | |
| nohis flag | CATCACCATCACCATCACGATTACA (SEQ ID NO: 33) |
| Lpp-R-plasmid | GCTGGAGCAACCTGCCAGCAGAG (SEQ ID NO: 34) |
| lpp-sta006-fl | CTGCTGGCAGGTTGCGGGAACCAAGGTGAAAAAATAAC AAAG (SEQ ID NO: 35) |
| sta00641 | GTGATGGTGATGTTATTTGCAGCTTTAATTAATTTTC TTTTAAATCTTTAC (SEQ ID NO: 36) |
| lpp-hla-fl | CTGCTGGCAGGTTGCGCAGATTCTGATATTAATATTAAA GACCGT (SEQ ID NO: 37) |
| hla-rl | GTGATGGTGATGTTAATTTGTCATTTCTTCTTTTTCCCA ATCGAT (SEQ ID NO: 38) |
| lpp-spa-fl | CTGCTGGCAGGTTGCGCACAGCATGATGAAGCCAAAAAA (SEQ ID NO: 39) |

TABLE 1-continued

Oligonucleotide primers used for plasmids and genes preparation

| NAME | SEQUENCE |
|---|---|
| spa-rl | GTGATGGTGATGTTATTTAGGTGCCTGTGCGTCGTT (SEQ ID NO: 40) |
| lpp-luke-fl | CTGCTGGCAGGTTGCAATACTAATATTGAAAATATTGGT GATGGTGC (SEQ ID NO: 41) |
| luke-rl | GTGATGGTGATGTTAATTATGTCCTTTCACTTTAATTTC GTGTGTTTTCCA (SEQ ID NO: 42) |
| D8-mFAT1 Minigene | |
| mFa-F1 | ATCCAAGTGGAGGCGACCGATAAAGACCTGGGTCCGTCG GGGCATGTG (SEQ ID NO: 43) |
| mFa-R1 | AACCTGAATTTCGGTGTCGGTCAGGATGGCATACGTCAC ATGCCCCGACGG (SEQ ID NO: 44) |
| mFa-F2 | ACCGAAATTCAGGTTGAAGCCACCGACAAAGACTTAGGC CCGAGTGGTCAC (SEQ ID NO: 45) |
| mFa-R2 | CTGAATTTCAGTATCGGTGAGAATCGCGTAGGTCACGTG ACCACTCGGGCC (SEQ ID NO: 46) |
| mFa-F3 | GATACTGAAATTCAGGTTGAAGCTACCGATAAAGATTTG GGCCCGAGTGGT (SEQ ID NO: 47) |
| mFa-R3 | TTCAGTATCCGTGAGGATCGCATAGGTTACATGACCACT CGGGCCCAA (SEQ ID NO: 48) |
| pET-FhuD2-D8-hFAT1-3x, pET-FhuD2-D8-mFAT1-3x and pET-FhuD2-EGRF-vIII-3x | |
| nohis flag | CATCACCATCACCATCACGATTACA (SEQ ID NO: 49) |
| fat1 FhUD2F | hu-TAATTAAAGCTGCAAAAATTCAAGTGGAAGCGACTG A (SEQ ID NO: 50) |
| fat1hu-FhUD2R | GATGGTGATGGTGATGTCAATCTGTATCGGTAACAATAG (SEQ ID NO: 51) |
| fat1ms-FhUD2F | TAATTAAAGCTGCAAAAATCCAAGTGGAGGCGACCGA (SEQ ID NO: 52) |
| fat1ms-FhUD2R | GATGGTGATGGTGATGTCATTCAGTATCCGTGAGGATCG (SEQ ID NO: 53) |
| VIII-FhUD2F | TAATTAAAGCTGCAAAAGGTTCCCTGGAAAAG (SEQ ID NO: 54) |
| VIII-FhUD2R | GATGGTGATGGTGATGTCAGCCGGAATGGTCGGTAACCA C (SEQ ID NO: 55) |
| FhUD2-V-R | TTTTGCAGCTTTAATTAATTTTTC (SEQ ID NO: 56) |
| pET-FhuD2-M03, pET-FhuD2-M20, pET-FhuD2-M26, pET-FhuD2-M27, pET-FhuD2-M68 plasmids | |
| nohis flag | CATCACCATCACCATCACGATTACA (SEQ ID NO: 57) |
| FhUD2-V-R | TTTTGCAGCTTTAATTAATTTTTC (SEQ ID NO: 58) |
| M03-F | TAATTAAAGCTGCAAAAGACAAGCCCTTACGTCGC (SEQ ID NO: 59) |
| M03-R | GATGGTGATGGTGATGtcaGGCACGAAAGCTATCAAGTG G (SEQ ID NO: 60) |
| M20-F | TAATTAAAGCTGCAAAACCTCTTTTACCTTTTTATCCAC C (SEQ ID NO: 61) |

TABLE 1-continued

Oligonucleotide primers used for plasmids and genes preparation

| NAME | SEQUENCE |
|------|----------|
| M20-R | GATGGTGATGGTGATGtcaTTCTGTGGGTGGCAACGC (SEQ ID NO: 62) |
| M26-F | TAATTAAAGCTGCAAAAGTAATTCTTCCCCAGGCCC (SEQ ID NO: 63) |
| M26-R | GATGGTGATGGTGATGtcaAGGAGGTGTTAACATCTGCGC (SEQ ID NO: 64) |
| M27-F | TAATTAAAGCTGCAAAAGAGCATATTCATCGTGCTGGTG (SEQ ID NO: 65) |
| M27-R | GATGGTGATGGTGATGtcaCCAGAAATGCTTACCGATGCG (SEQ ID NO: 66) |

TABLE 1-continued

Oligonucleotide primers used for plasmids and genes preparation

| NAME | SEQUENCE |
|------|----------|
| M68-F | TAATTAAAGCTGCAAAAGTAACAAGCATCCCATCCGTCTC (SEQ ID NO: 67) |
| M68-R | GATGGTGATGGTGATGtcaGGCCACGTAGCCCAAGGTAC (SEQ ID NO: 68) |
| pET-FhuD2-OVA-3X | |
| OVA-FhuD2F | TAATTAAAGCTGCAAAACAGCTGGAAAGCATTATTAACTTTGAAAAAC (SEQ ID NO: 79) |
| OVA-FhuD2R | TGGTGATGGTGATGTTATTCGGTCAGTTTTTCGAAGTTGATGATGCTTTC (SEQ ID NO: 80) |

The invention claimed is:

1. An isolated bacterial outer membrane vesicle (OMV) comprising a fusion protein wherein
    (i) the bacterial protein FhuD2 is fused to one or more copies of a heterologous polypeptide, and wherein the heterologous polypeptide is linked to the carboxyl terminus of FhuD2,
    (ii) said FhuD2 carries an acylated N-terminal residue, and
    (iii) said fusion protein is expressed on the OMV surface.

2. The isolated bacterial outer membrane vesicle of claim 1, wherein said acylated N-terminal residue is a cysteine residue deriving from the cleavage of a lipoprotein leader sequence present in an immature precursor form of said fusion protein.

3. The isolated bacterial outer membrane vesicle of claim 1, wherein said fusion protein comprises from 1 to 20 copies of the heterologous polypeptide, optionally spaced by a linker sequence.

4. The isolated bacterial outer membrane vesicle of claim 1, wherein the heterologous polypeptide is a tumor-associated antigen.

5. The isolated bacterial outer membrane vesicle of claim 4, wherein said tumor-associated antigen carries a B cell epitope, and/or a CD4+ T cell epitope, and/or a CD8+ T cell epitope.

6. A method of preparing a bacterial outer membrane vesicle (OMV) comprising a fusion protein wherein (a) the bacterial protein FhuD2 is fused to one or more copies of a heterologous polypeptide, and wherein the heterologous polypeptide is linked to the carboxyl terminus of FhuD2, (b) said FhuD2 carries an acylated N-terminal residue, and (c) said fusion protein is expressed on the OMV surface said method comprising:
    (i) expressing on the surface of a Gram-negative bacterium said fusion protein; and
    (ii) isolating the outer membrane vesicle from the bacterial culture.

7. The method of claim 6, wherein said fusion protein is expressed on the surface of a Gram-negative bacterium by means of an expression vector comprising a nucleic acid sequence encoding the fusion protein linked to a nucleic acid sequence encoding a signal sequence of a lipoprotein.

8. The method of claim 6, wherein said Gram-negative bacterium is *Escherichia coli*.

9. An immunogenic composition comprising the bacterial outer membrane vesicle of claim 1, optionally in combination with pharmaceutically acceptable adjuvants and pharmaceutically acceptable excipients.

10. The immunogenic composition of claim 9, which is in the form of a vaccine.

11. A method to stimulate an immune response in a subject in need thereof, which comprises administering the immunogenic composition of claim 9 to said subject.

12. The method of claim 11, wherein said subject is a tumor patient.

* * * * *

SEQUENCE LISTING

<160> NUMBER OF SEQ ID NOS: 80

<210> SEQ ID NO 1
<211> LENGTH: 858
<212> TYPE: DNA
<213> ORGANISM: Staphylococcus aureus

<400> SEQUENCE: 1

```
tgtgggaacc aaggtgaaaa aaataacaaa gctgaaacta atcttataa aatggacgat      60
ggcaaaacgg tagatattcc gaaagaccct aaacgcattg cagtagttgc gccaacatat     120
gctggtggac ttaaaaaatt aggtgcaaac attgtagctg taaatcaaca agtcgatcaa     180
agcaaagtat taaaagataa atttaaaggt gttacaaaaa ttggtgatgg cgatgtgaaa     240
aaagttgcta agaaaagcc agatttaatt attgtatact ctactgacaa agatattaaa     300
aaatatcaaa agtagcacc aacagtagtt gttgactata ataagcataa atatttagaa     360
caacaagaaa tgttagggaa aattgttggt aagaagata aagtaaaagc ttggaagaaa     420
gattgggaag aaacaactgc taaagacggt aaagaaatta aaaagcaat tggacaagat    480
gcaacagtgt cattgtttga tgaatttgat aaaaaattat acacttacgg cgataactgg    540
ggtcgtggtg gagaagtatt atatcaagca tttggtttga aatgcaacc agaacaacaa    600
aagttaactg caaagcagg ttgggctgaa gtgaaacaag aagaattga aaaatatgct    660
ggtgattaca ttgtgagtac aagtgaaggt aaacctacac aggatacga atcaacaaac    720
atgtggaaga atttgaaagc tactaaagaa ggacatattg ttaaagttga tgctggtaca    780
tactggtaca acgatcctta tacattagat ttcatgcgta agatttaaa agaaaaatta    840
attaaagctg caaaataa                                                    858
```

<210> SEQ ID NO 2
<211> LENGTH: 921
<212> TYPE: DNA
<213> ORGANISM: Staphylococcus aureus

<400> SEQUENCE: 2

```
atgatgaaag ctactaaact ggtactgggc gcggtaatcc tgggttctac tctgctggca      60
ggttgtggga accaaggtga aaaaaataac aaagctgaaa ctaatctta taaaatggac     120
gatggcaaaa cggtagatat tccgaaagac cctaaacgca ttgcagtagt tgcgccaaca    180
```

| | |
|---|---|
| tatgctggtg gacttaaaaa attaggtgca aacattgtag ctgtaaatca acaagtcgat | 240 |
| caaagcaaag tattaaaaga taaatttaaa ggtgttacaa aaattggtga tggcgatgta | 300 |
| gaaaaagttg ctaaagaaaa gccagattta attattgtat actctactga caaagatatt | 360 |
| aaaaaatatc aaaaagtagc accaacagta gttgttgact ataataagca taaatattta | 420 |
| gaacaacaag aaatgttagg gaaaattgtt ggtaaagaag ataaagtaaa agcttggaag | 480 |
| aaagattggg aagaaacaac tgctaaagac ggtaaagaaa ttaaaaaagc aattggacaa | 540 |
| gatgcaacag tgtcattgtt tgatgaattt gataaaaaat tatacactta cggcgataac | 600 |
| tggggtcgtg gtggagaagt attatatcaa gcatttggtt tgaaaatgca accagaacaa | 660 |
| caaaagttaa ctgcaaaagc aggttgggct gaagtgaaac aagaagaaat tgaaaaatat | 720 |
| gctggtgatt acattgtgag tacaagtgaa ggtaaaccta caccaggata cgaatcaaca | 780 |
| aacatgtgga agaatttgaa agctactaaa gaaggacata ttgttaaagt tgatgctggt | 840 |
| acatactggt acaacgatcc ttatacatta gatttcatgc gtaaagattt aaaagaaaaa | 900 |
| ttaattaaag ctgcaaaata a | 921 |

<210> SEQ ID NO 3
<211> LENGTH: 882
<212> TYPE: DNA
<213> ORGANISM: Staphylococcus aureus

<400> SEQUENCE: 3

| | |
|---|---|
| gcagattctg atattaatat taaaaccggt actacagata ttggaagcaa tactacagta | 60 |
| aaaacaggtg atttagtcac tttgataaaa gaaaatggca tgttaaaaaa agtatttat | 120 |
| agttttatcg atgataaaaa tcataataaa aaactgctag ttattagaac gaaaggtacc | 180 |
| attgctggtc aatatagagt ttatagcgaa gaaggtgcta caaaagtgg tttagcctgg | 240 |
| ccttcagcct ttaaggtaca gttgcaacta cctgataatg aagtagctca atatctgat | 300 |
| tactatccaa gaaattcgat tgatacaaaa gagtatatga gtactttaac ttatggattc | 360 |
| aacggtaatg ttactggtga tgatacagga aaaattggcg gccttattgg tgcaaatgtt | 420 |
| tcgattggtc atacactgaa atatgttcaa cctgatttca aaacaatttt agagagccca | 480 |
| actgataaaa aagtaggctg gaaagtgata tttaacaata tggtgaatca aaattgggga | 540 |
| ccatatgata gagattcttg gaacccggta tatggcaatc aacttttcat gaaaactaga | 600 |
| aatggctcta tgaaagcagc agataacttc cttgatccta caaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgactacca attgcactgg | 780 |
| acttcaacaa attggaaagg taccaatact aaagataaat ggatagatcg ttcttcagaa | 840 |
| agatataaaa tcgattggga aaaagaagaa atgacaaatt aa | 882 |

<210> SEQ ID NO 4
<211> LENGTH: 945
<212> TYPE: DNA
<213> ORGANISM: Staphylococcus aureus

<400> SEQUENCE: 4

| | |
|---|---|
| atgaaagcta ctaaactggt actgggcgcg gtaatcctgg ttctactct gctggcaggt | 60 |
| tgtgcagatt ctgatattaa tattaaaacc ggtactacag atattggaag caatactaca | 120 |
| gtaaaaacag gtgatttagt cacttatgat aaagaaaatg gcatgctcaa aaagtatttt | 180 |
| tatagttttta tcgatgataa aaatcataat aaaaaaactgc tagttattag aacgaaaggt | 240 |

```
accattgctg gtcaatatag agtttatagc gaagaaggtg ctaacaaaag tggtttagcc      300
tggccttcag cctttaaggt acagttgcaa ctacctgata atgaagtagc tcaaatatct      360
gattactatc caagaaattc gattgataca aagagtata tgagtacttt aacttatgga       420
ttcaacggta atgttactgg tgatgataca ggaaaaattg gcggccttat tggtgcaaat      480
gtttcgattg gtcatacact gaaatatgtt caacctgatt tcaaaacaat tttagagagc      540
ccaactgata aaaagtagg ctggaaagtg atatttaaca atatggtgaa tcaaaattgg       600
ggaccatatg atagagattc ttggaacccg gtatatggca atcaactttt catgaaaact      660
agaaatggct ctatgaaagc agcagataac ttccttgatc ctaacaaagc aagttctcta      720
ttatcttcag ggttttcacc agacttcgct acagttatta ctatggatag aaaagcatcc      780
aaacaacaaa caaatataga gtaatatac gaacgagttc gtgatgacta ccaattgcac       840
tggacttcaa caaattggaa aggtaccaat actaaagata aatggataga tcgttcttca      900
gaaagatata aatcgattg ggaaaaagaa gaaatgacaa attaa                       945

<210> SEQ ID NO 5
<211> LENGTH: 873
<212> TYPE: DNA
<213> ORGANISM: Staphylococcus aureus

<400> SEQUENCE: 5
gcacagcatg atgaagccaa aaaaacgcc ttttatcagg ttctgaatat gccgaatctg        60
aatgccgatc agcgtaatgg ttttattcag agcctgaaag cagcaccgag ccagagcgca     120
aatgttctgg gtgaagcaca gaaactgaat gatagccagg caccgaaagc agatgccaaa     180
cgcaacaatt ttaacaaaga taaaaaaagc gcgttttatg aaatcctgaa catgcctaac     240
ctgaatgaag cacagcgcaa tggctttatc cagtctctga agccgcacc gtcacagtct      300 accaatgtgc tgggcgaagc gaaaaaactg aacgaatccc aggctccgaa agccgataat     360
aacttcaaca aagagaaaaa aaacgccttt tatgaaattc tgaatatgcc aaatctgaac     420
gaagaacagc gtaacggttt tattcagtca ctgaaagcgg ctcctagcca gtctgcaaat     480
ctgctgtctg aagccaaaaa actgaatgaa agtcaggcac taaagcgga taacaaattt      540 aacaaagaga aaaaaacgc attttatgaa atcctgcatc tgccgaatct gaatgaagaa      600
cagcgcaacg gctttattca gagtctgaaa gccgctccgt cccagagcgc caacctgctg     660
gccgaagcaa aaaactgaa tgatgcgcag gctccgaaag cagataacaa atttaacaaa      720
gagaaaaaaa acgccttcta tgaaattctg cacctgccta acctgaccga gaacagcgt      780 aatggtttta tccagtccct gaaagcggct cctagcgtta gcaaagaaat cctggcagag     840
gccaaaaaac tgaacgacgc acaggcacct aaa                                   873

<210> SEQ ID NO 6
<211> LENGTH: 942
<212> TYPE: DNA
<213> ORGANISM: Staphylococcus aureus

<400> SEQUENCE: 6
atgatgaaag ctactaaact ggtactgggc gcggtaatcc tgggttctac tctgctggca      60
ggttgcgcac agcatgatga agccaaaaaa aacgcctttt atcaggttct gaatatgccg     120
aatctgaatg ccgatcagcg taatggtttt attcagagcc tgaaagcagc accgagccag     180
agcgcaaatg ttctgggtga agcacagaaa ctgaatgata gccaggcacc gaaagcagat     240
```

| | |
|---|---|
| gccaaacgca acaattttaa caaagataaa aaaagcgcgt tttatgaaat cctgaacatg | 300 |
| cctaacctga atgaagcaca gcgcaatggc tttatccagt ctctgaaagc cgcaccgtca | 360 |
| cagtctacca atgtgctggg cgaagcgaaa aaactgaacg aatcccaggc tccgaaagcc | 420 |
| gataataact tcaacaaaga gaaaaaaaac gccttttatg aaattctgaa tatgccaaat | 480 |
| ctgaacgaag aacagcgtaa cggttttatt cagtcactga agcggctcc tagccagtct | 540 |
| gcaaatctgc tgtctgaagc caaaaaactg aatgaaagtc aggcacctaa agcggataac | 600 |
| aaatttaaca aagagaaaaa aaacgcattt tatgaaatcc tgcatctgcc gaatctgaat | 660 |
| gaagaacagc gcaacggctt tattcagagt ctgaaagccg ctccgtccca gagcgccaac | 720 |
| ctgctggccg aagcaaaaaa actgaatgat gcgcaggctc cgaaagcaga taacaaattt | 780 |
| aacaaagaga aaaaaaacgc cttctatgaa attctgcacc tgcctaacct gaccgaagaa | 840 |
| cagcgtaatg gttttatcca gtccctgaaa gcggctccta gcgttagcaa agaaatcctg | 900 |
| gcagaggcca aaaaactgaa cgacgcacag gcacctaaat aa | 942 |

<210> SEQ ID NO 7
<211> LENGTH: 906
<212> TYPE: DNA
<213> ORGANISM: Staphylococcus aureus

<400> SEQUENCE: 7

| | |
|---|---|
| ttgtcagtag gactgattgc acctttagca tctccgattc aagaatctag agcaaatact | 60 |
| aatattgaaa atattggtga tggtgctgaa gtaatcaaac gtacggagga tgtaagtagt | 120 |
| aagaaatggg gcgttactca aatgtccaa ttcgactttg taaagataaa aaatataaac | 180 |
| aaagacgctt taattgttaa aatgcaaggt tttattaatt ccagaacttc attttcagat | 240 |
| gtgaagggta gtggatatga attaactaaa cgaatgattt ggccattcca atataatata | 300 |
| ggactgacga ctaaagatcc aaatgttagc ttaatcaatt accttcctaa aaacaaaata | 360 |
| gaaactactg atgttggtca aacattagga tataacattg gaggtaattt ccagtcagca | 420 |
| ccatctatag gtggcaatgg ctcatttaat tattctaaaa caattagtta tacccaaaag | 480 |
| agttatgtca gtgaagtaga caagcaaaac tcaaaatctg ttaaatgggg tgttaaagca | 540 |
| aacgaatttg ttacgcctga tggaaaaaaa tctgcgcatg atagatattt attcgtacaa | 600 |
| agtccaaatg gtccaacagg ttcagcaaga gaatattttg ctcctgataa tcaattgcca | 660 |
| cctttagttc aaagtggctt taatccatcg tttatcacta cactatcaca tgaaaaaggt | 720 |
| tcaagtgata cgagtgaatt tgaaatttca tatggtagaa acttagatat tacatatgcg | 780 |
| acttattcc ctagaactgg tatttacgca gaaagaaagc ataatgcatt tgtaaataga | 840 |
| aactttgtag ttagatatga agttaattgg aaaacacacg aaattaaagt gaaaggacat | 900 |
| aattaa | 906 |

<210> SEQ ID NO 8
<211> LENGTH: 918
<212> TYPE: DNA
<213> ORGANISM: Staphylococcus aureus

<400> SEQUENCE: 8

| | |
|---|---|
| atgaaagcta ctaaactggt actgggcgcg gtaatcctgg ttctactct gctggcaggt | 60 |
| tgcaatacta atattgaaaa tattggtgat ggtgctgaag taatcaaacg tacggaggat | 120 |
| gtaagtagta agaaatgggg cgttactcaa atgtccaat tcgactttgt aaagataaa | 180 |
| aaatataaca agacgctttt aattgttaaa atgcaaggtt ttattaattc agaacttca | 240 |

-continued

```
ttttcagatg tgaagggtag tggatatgaa ttaactaaac gaatgatttg gccattccaa      300
tataatatag gactgacgac taaagatcca aatgttagct taatcaatta ccttcctaaa      360
aacaaaatag aaactactga tgttggtcaa acattaggat ataacattgg aggtaatttc      420
cagtcagcac catctatagg tggcaatggc tcatttaatt attctaaaac aattagttat      480
acccaaaaga gttatgtcag tgaagtagac aagcaaaact caaatctgt taaatggggt       540 gttaaagcaa acgaatttgt tacgcctgat ggaaaaaaat ctgcgcatga tagatattta      600
ttcgtacaaa gtccaaatgg tccaacaggt tcagcaagag aatattttgc tcctgataat      660
caattgccac ctttagttca aagtggcttt aatccatcgt ttatcactac actatcacat      720
gaaaaaggtt caagtgatac gagtgaattt gaaatttcat atggtagaaa cttagatatt      780
acatatgcga ctttattccc tagaactggt atttacgcag aaagaaagca taatgcattt      840
gtaaatagaa actttgtagt tagatatgaa gttaattgga aaacacacga aattaaagtg      900
aaaggacata attaataa                                                    918
```

<210> SEQ ID NO 9
<211> LENGTH: 1146
<212> TYPE: DNA
<213> ORGANISM: Artificial Sequence
<220> FEATURE:
<223> OTHER INFORMATION: FhuD2-hFAT1 fusion protein encoding sequence

<400> SEQUENCE: 9

```
atgatgaaag ctactaaact ggtactgggc gcggtaatcc tgggttctac tctgctggca       60
ggttgcggga accaaggtga aaaaaataac aaagctgaaa ctaaatctta taaaatggac      120
gatggcaaaa cggtagatat tccgaaagac cctaaacgca ttgcagtagt tgcgccaaca      180
tatgctggtg gacttaaaaa attaggtgca aacattgtag ctgtaaatca acaagtcgat      240
caaagcaaag tattaaaaga taaatttaaa ggtgttacaa aaattggtga tggcgatgta      300
gaaaaagttg ctaagaaaaa gccagattta attattgtat actctactga caaagatatt      360
aaaaaatatc aaaaagtagc accaacagta gttgttgact ataataagca taaatattta      420
gaacaacaag aaatgttagg gaaaattgtt ggtaaagaag ataaagtaaa agcttggaag      480
aaagattggg aagaaacaac tgctaaagac ggtaaagaaa ttaaaaaagc aattggacaa      540
gatgcaacag tgtcattgtt tgatgaattt gataaaaaat tatacactta cggcgataac      600
tggggtcgtg gtggagaagt attatatcaa gcatttggtt tgaaaatgca accagaacaa      660
caaaagttaa ctgcaaaagc aggttgggct gaagtgaaac aagaagaaat tgaaaaatat      720
gctggtgatt acattgtgag tacaagtgaa ggtaaaccta caccaggata cgaatcaaca      780
aacatgtgga gaatttgaa agctactaaa gaaggacata ttgttaaagt tgatgctggt      840
acatactggt acaacgatcc ttatacatta gatttcatgc gtaaagattt aaaagaaaaa      900
ttaattaaag ctgcaaaaat tcaagtgaaa gcgactgaca agatctgggc ccgaatggc       960 catgtaactt attcaatcgt tacggataca gatatccagg tagaggcaac cgataaagat     1020
ttaggtccca atggccacgt cacatatagt atcgtaacgg ataccgacat tcaggtggaa     1080
gctaccgata aagacctggg tccgaatggc acgtgacgt attctattgt taccgataca     1140
gattga                                                                1146
```

<210> SEQ ID NO 10
<211> LENGTH: 1143
<212> TYPE: DNA

<213> ORGANISM: Artificial Sequence
<220> FEATURE:
<223> OTHER INFORMATION: FhuD2-mFAT1 fusion protein encoding sequence

<400> SEQUENCE: 10

```
atgatgaaag ctactaaact ggtactgggc gcggtaatcc tgggttctac tctgctggca      60
ggttgcggga accaaggtga aaaaaataac aaagctgaaa ctaaatctta taaaatggac     120
gatggcaaaa cggtagatat tccgaaagac cctaaacgca ttgcagtagt tgcgccaaca     180
tatgctggtg gacttaaaaa attaggtgca aacattgtag ctgtaaatca acaagtcgat     240
caaagcaaag tattaaaaga taaatttaaa ggtgttacaa aaattggtga tggcgatgta     300
gaaaaagttg ctaaagaaaa gccagattta attattgtat actctactga caaagatatt     360
aaaaaatatc aaaaagtagc accaacagta gttgttgact ataataagca taaatattta     420
gaacaacaag aaatgttagg gaaaattgtt ggtaagaag ataaagtaaa agcttggaag      480
aaagattggg aagaaacaac tgctaaagac ggtaaagaaa ttaaaaaagc aattggacaa     540
gatgcaacag tgtcattgtt tgatgaattt gataaaaaat tatacactta cggcgataac     600
tggggtcgtg gtggagaagt attatatcaa gcatttggtt tgaaaatgca accagaacaa     660
caaaagttaa ctgcaaaagc aggttgggct gaagtgaaac aagaagaaat tgaaaaatat     720
gctggtgatt acattgtgag tacaagtgaa ggtaaaccta caccaggata cgaatcaaca     780
aacatgtgga gaatttgaa agctactaaa gaaggacata ttgttaaagt tgatgctggt      840
acatactggt acaacgatcc ttatacatta gatttcatgc gtaaagattt aaaagaaaaa     900
ttaattaaag ctgcaaaaat ccaagtggag gcgaccgata agacctgggt ccgtcgggg      960
catgtgacgt atgccatcct gaccgacacc gaaattcagg ttgaagccac cgacaaagac    1020
ttaggcccga gtggtcacgt gacctacgcg attctcaccg atactgaaat tcaggttgaa    1080
gctaccgata agatttgggc ccgagtggt catgtaacct atgcgatcct cacggatact    1140
gaa                                                                  1143
```

<210> SEQ ID NO 11
<211> LENGTH: 1062
<212> TYPE: DNA
<213> ORGANISM: Artificial Sequence
<220> FEATURE:
<223> OTHER INFORMATION: FhuD2-EGFRviii fusion protein encoding sequence

<400> SEQUENCE: 11

```
atgatgaaag ctactaaact ggtactgggc gcggtaatcc tgggttctac tctgctggca      60
ggttgcggga accaaggtga aaaaaataac aaagctgaaa ctaaatctta taaaatggac     120
gatggcaaaa cggtagatat tccgaaagac cctaaacgca ttgcagtagt tgcgccaaca     180
tatgctggtg gacttaaaaa attaggtgca aacattgtag ctgtaaatca acaagtcgat     240
caaagcaaag tattaaaaga taaatttaaa ggtgttacaa aaattggtga tggcgatgta     300
gaaaaagttg ctaaagaaaa gccagattta attattgtat actctactga caaagatatt     360
aaaaaatatc aaaaagtagc accaacagta gttgttgact ataataagca taaatattta     420
gaacaacaag aaatgttagg gaaaattgtt ggtaagaag ataaagtaaa agcttggaag      480
aaagattggg aagaaacaac tgctaaagac ggtaaagaaa ttaaaaaagc aattggacaa     540
gatgcaacag tgtcattgtt tgatgaattt gataaaaaat tatacactta cggcgataac     600
tggggtcgtg gtggagaagt attatatcaa gcatttggtt tgaaaatgca accagaacaa     660
caaaagttaa ctgcaaaagc aggttgggct gaagtgaaac aagaagaaat tgaaaaatat     720
```

```
gctggtgatt acattgtgag tacaagtgaa ggtaaaccta caccaggata cgaatcaaca     780
aacatgtgga agaatttgaa agctactaaa gaaggacata ttgttaaagt tgatgctggt     840
acatactggt acaacgatcc ttatacatta gatttcatgc gtaaagattt aaaagaaaaa     900
ttaattaaag ctgcaaaagg ttccctggaa gaaaagaagg taactatgt ggtgaccgac      960 cactctggtc tggaggagaa aaaaggcaac tacgttgtta ctgatcacgg ctctctggag    1020
gaaaagaaag gtaattacgt ggttaccgac cattccggct ga                       1062

<210> SEQ ID NO 12
<211> LENGTH: 1002
<212> TYPE: DNA
<213> ORGANISM: Artificial Sequence
<220> FEATURE:
<223> OTHER INFORMATION: FhuD2-M03 fusion protein encoding sequence

<400> SEQUENCE: 12
atgatgaaag ctactaaact ggtactgggc gcggtaatcc tgggttctac tctgctggca      60
ggttgcggga accaaggtga aaaaaataac aaagctgaaa ctaaatctta taaaatggac     120
gatggcaaaa cggtagatat tccgaaagac cctaaacgca ttgcagtagt tgcgccaaca     180
tatgctggtg gacttaaaaa attaggtgca aacattgtag ctgtaaatca acaagtcgat     240
caaagcaaag tattaaaaga taaatttaaa ggtgttacaa aaattggtga tgcgatgta      300 gaaaaagttg ctaaagaaaa gccagattta attattgtat actctactga caaagatatt     360
aaaaaatatc aaaagtagc accaacagta gttgttgact ataataagca taaatattta     420
gaacaacaag aaatgttagg gaaaattgtt ggtaaagaag ataaagtaaa agcttggaag     480
aaagattggg aagaaacaac tgctaaagac ggtaaagaaa ttaaaaaagc aattggacaa     540
gatgcaacag tgtcattgtt tgatgaattt gataaaaaat tatacactta cggcgataac     600
tggggtcgtg gtggagaagt attatatcaa gcatttggtt tgaaaatgca accgaacaa      660 caaaagttaa ctgcaaaagc aggttgggct gaagtgaaac aagaagaaat tgaaaaatat     720
gctggtgatt acattgtgag tacaagtgaa ggtaaaccta caccaggata cgaatcaaca     780
aacatgtgga agaatttgaa agctactaaa gaaggacata ttgttaaagt tgatgctggt     840
acatactggt acaacgatcc ttatacatta gatttcatgc gtaaagattt aaaagaaaaa     900
ttaattaaag ctgcaaaaga caagccctta cgtcgcaata actcctatac gagctatatt     960
atggcgatct gcgggatgcc acttgatagc tttcgtgcct ga                       1002

<210> SEQ ID NO 13
<211> LENGTH: 999
<212> TYPE: DNA
<213> ORGANISM: Artificial Sequence
<220> FEATURE:
<223> OTHER INFORMATION: FhuD2-M20 fusion protein encoding sequence

<400> SEQUENCE: 13
atgatgaaag ctactaaact ggtactgggc gcggtaatcc tgggttctac tctgctggca      60
ggttgcggga accaaggtga aaaaaataac aaagctgaaa ctaaatctta taaaatggac     120
gatggcaaaa cggtagatat tccgaaagac cctaaacgca ttgcagtagt tgcgccaaca     180
tatgctggtg gacttaaaaa attaggtgca aacattgtag ctgtaaatca acaagtcgat     240
caaagcaaag tattaaaaga taaatttaaa ggtgttacaa aaattggtga tgcgatgta      300 gaaaaagttg ctaaagaaaa gccagattta attattgtat actctactga caaagatatt     360
```

```
aaaaaatatc aaaaagtagc accaacagta gttgttgact ataataagca taaatattta    420
gaacaacaag aaatgttagg gaaaattgtt ggtaaagaag ataaagtaaa agcttggaag    480
aaagattggg aagaaacaac tgctaaagac ggtaaagaaa ttaaaaaagc aattggacaa    540
gatgcaacag tgtcattgtt tgatgaattt gataaaaaat tatacactta cggcgataac    600
tggggtcgtg gtggagaagt attatatcaa gcatttggtt tgaaaatgca accagaacaa    660
caaaagttaa ctgcaaaagc aggttgggct gaagtgaaac aagaagaaat tgaaaaatat    720
gctggtgatt acattgtgag tacaagtgaa ggtaaaccta caccaggata cgaatcaaca    780
aacatgtgga agaatttgaa agctactaaa gaaggacata ttgttaaagt tgatgctggt    840
acatactggt acaacgatcc ttatacatta gatttcatgc gtaaagattt aaaagaaaaa    900
ttaattaaag ctgcaaaacc tcttttacct ttttatccac cagacgaggc attggaaatc    960
ggccttgaat taaattcttc agcgttgcca cccacagaa                          999

<210> SEQ ID NO 14
<211> LENGTH: 1002
<212> TYPE: DNA
<213> ORGANISM: Artificial Sequence
<220> FEATURE:
<223> OTHER INFORMATION: FhuD2-M26 fusion protein encoding sequence

<400> SEQUENCE: 14
atgatgaaag ctactaaact ggtactgggc gcggtaatcc tgggttctac tctgctggca     60
ggttgcggga accaaggtga aaaaataac aaagctgaaa ctaaatctta taaatggac     120 gatgcaaaa cggtagatat tccgaaagac cctaaacgca ttgcagtagt tgcgccaaca    180
tatgctggtg gacttaaaaa attaggtgca aacattgtag ctgtaaatca acaagtcgat    240
caaagcaaag tattaaaaga taaatttaaa ggtgttacaa aaattggtga tggcgatgta    300
gaaaaagttg ctaagaaaa gccagattta attattgtat actctactga caaagatatt    360
aaaaaatatc aaaaagtagc accaacagta gttgttgact ataataagca taaatattta    420
gaacaacaag aaatgttagg gaaaattgtt ggtaaagaag ataaagtaaa agcttggaag    480
aaagattggg aagaaacaac tgctaaagac ggtaaagaaa ttaaaaaagc aattggacaa    540
gatgcaacag tgtcattgtt tgatgaattt gataaaaaat tatacactta cggcgataac    600
tggggtcgtg gtggagaagt attatatcaa gcatttggtt tgaaaatgca accagaacaa    660
caaaagttaa ctgcaaaagc aggttgggct gaagtgaaac aagaagaaat tgaaaaatat    720
gctggtgatt acattgtgag tacaagtgaa ggtaaaccta caccaggata cgaatcaaca    780
aacatgtgga agaatttgaa agctactaaa gaaggacata ttgttaaagt tgatgctggt    840
acatactggt acaacgatcc ttatacatta gatttcatgc gtaaagattt aaaagaaaaa    900
ttaattaaag ctgcaaaagt aattcttccc caggccccga gcggaccgtc ctacgcaaca    960
tacttacaac ctgcccaggc gcagatgtta acacctcctt ga                     1002

<210> SEQ ID NO 15
<211> LENGTH: 1002
<212> TYPE: DNA
<213> ORGANISM: Artificial Sequence
<220> FEATURE:
<223> OTHER INFORMATION: FhuD2-M27 fusionprotein encoding sequence

<400> SEQUENCE: 15
atgatgaaag ctactaaact ggtactgggc gcggtaatcc tgggttctac tctgctggca     60
ggttgcggga accaaggtga aaaaataac aaagctgaaa ctaaatctta taaatggac     120
```

```
gatggcaaaa cggtagatat tccgaaagac cctaaacgca ttgcagtagt tgcgccaaca      180
tatgctggtg gacttaaaaa attaggtgca aacattgtag ctgtaaatca acaagtcgat      240
caaagcaaag tattaaaaga taaatttaaa ggtgttacaa aaattggtga tggcgatgta      300
gaaaaagttg ctaaagaaaa gccagattta attattgtat actctactga caagatatt       360 aaaaaatatc aaaaagtagc accaacagta gttgttgact ataataagca taaatattta      420
gaacaacaag aaatgttagg gaaaattgtt ggtaaagaag ataaagtaaa agcttggaag      480
aaagattggg aagaaacaac tgctaaagac ggtaaagaaa ttaaaaaagc aattggacaa      540
gatgcaacag tgtcattgtt tgatgaattt gataaaaaat tatacactta cggcgataac      600
tggggtcgtg gtggagaagt attatatcaa gcatttggtt tgaaaatgca accagaacaa      660
caaaagttaa ctgcaaaagc aggttgggct gaagtgaaac aagaagaaat tgaaaaatat      720
gctggtgatt acattgtgag tacaagtgaa ggtaaaccta caccaggata cgaatcaaca      780
aacatgtgga agaatttgaa agctactaaa gaaggacata ttgttaaagt tgatgctggt      840
acatactggt acaacgatcc ttatacatta gatttcatgc gtaaagattt aaaagaaaaa      900
ttaattaaag ctgcaaaaga gcatattcat cgtgctggtg acttttttgt ggctgacgca      960
attcaagtag gatttggacg catcggtaag catttctggt ga                       1002

<210> SEQ ID NO 16
<211> LENGTH: 1002
<212> TYPE: DNA
<213> ORGANISM: Artificial Sequence
<220> FEATURE:
<223> OTHER INFORMATION: FhuD2-M68 fusion protein encoding sequence

<400> SEQUENCE: 16
atgatgaaag ctactaaact ggtactgggc gcggtaatcc tgggttctac tctgctggca       60
ggttgcggga accaaggtga aaaaaataac aaagctgaaa ctaaatctta taaaatggac      120
gatggcaaaa cggtagatat tccgaaagac cctaaacgca ttgcagtagt tgcgccaaca      180
tatgctggtg gacttaaaaa attaggtgca aacattgtag ctgtaaatca acaagtcgat      240
caaagcaaag tattaaaaga taaatttaaa ggtgttacaa aaattggtga tggcgatgta      300
gaaaaagttg ctaaagaaaa gccagattta attattgtat actctactga caagatatt       360 aaaaaatatc aaaaagtagc accaacagta gttgttgact ataataagca taaatattta      420
gaacaacaag aaatgttagg gaaaattgtt ggtaaagaag ataaagtaaa agcttggaag      480
aaagattggg aagaaacaac tgctaaagac ggtaaagaaa ttaaaaaagc aattggacaa      540
gatgcaacag tgtcattgtt tgatgaattt gataaaaaat tatacactta cggcgataac      600
tggggtcgtg gtggagaagt attatatcaa gcatttggtt tgaaaatgca accagaacaa      660
caaaagttaa ctgcaaaagc aggttgggct gaagtgaaac aagaagaaat tgaaaaatat      720
gctggtgatt acattgtgag tacaagtgaa ggtaaaccta caccaggata cgaatcaaca      780
aacatgtgga agaatttgaa agctactaaa gaaggacata ttgttaaagt tgatgctggt      840
acatactggt acaacgatcc ttatacatta gatttcatgc gtaaagattt aaaagaaaaa      900
ttaattaaag ctgcaaaagt aacaagcatc ccatccgtct ctaatgctct gaattggaaa      960
gaattttcgt ttattcagag taccttgggc tacgtggcct ga                       1002

<210> SEQ ID NO 17
<211> LENGTH: 285
<212> TYPE: PRT
```

<213> ORGANISM: Staphylococcus aureus

<400> SEQUENCE: 17

```
Cys Gly Asn Gln Gly Glu Lys Asn Asn Lys Ala Glu Thr Lys Ser Tyr
1               5                   10                  15
Lys Met Asp Asp Gly Lys Thr Val Asp Ile Pro Lys Asp Pro Lys Arg
            20                  25                  30
Ile Ala Val Val Ala Pro Thr Tyr Ala Gly Gly Leu Lys Lys Leu Gly
        35                  40                  45
Ala Asn Ile Val Ala Val Asn Gln Gln Val Asp Gln Ser Lys Val Leu
    50                  55                  60
Lys Asp Lys Phe Lys Gly Val Thr Lys Ile Gly Asp Gly Asp Val Glu
65                  70                  75                  80
Lys Val Ala Lys Glu Lys Pro Asp Leu Ile Ile Val Tyr Ser Thr Asp
                85                  90                  95
Lys Asp Ile Lys Lys Tyr Gln Lys Val Ala Pro Thr Val Val Val Asp
            100                 105                 110
Tyr Asn Lys His Lys Tyr Leu Glu Gln Gln Glu Met Leu Gly Lys Ile
        115                 120                 125
Val Gly Lys Glu Asp Lys Val Lys Ala Trp Lys Lys Asp Trp Glu Glu
    130                 135                 140
Thr Thr Ala Lys Asp Gly Lys Glu Ile Lys Lys Ala Ile Gly Gln Asp
145                 150                 155                 160
Ala Thr Val Ser Leu Phe Asp Glu Phe Asp Lys Lys Leu Tyr Thr Tyr
                165                 170                 175
Gly Asp Asn Trp Gly Arg Gly Gly Glu Val Leu Tyr Gln Ala Phe Gly
            180                 185                 190
Leu Lys Met Gln Pro Glu Gln Gln Lys Leu Thr Ala Lys Ala Gly Trp
        195                 200                 205
Ala Glu Val Lys Gln Glu Glu Ile Glu Lys Tyr Ala Gly Asp Tyr Ile
    210                 215                 220
Val Ser Thr Ser Glu Gly Lys Pro Thr Pro Gly Tyr Glu Ser Thr Asn
225                 230                 235                 240
Met Trp Lys Asn Leu Lys Ala Thr Lys Glu Gly His Ile Val Lys Val
                245                 250                 255
Asp Ala Gly Thr Tyr Trp Tyr Asn Asp Pro Tyr Thr Leu Asp Phe Met
            260                 265                 270
Arg Lys Asp Leu Lys Glu Lys Leu Ile Lys Ala Ala Lys
        275                 280                 285
```

<210> SEQ ID NO 18
<211> LENGTH: 306
<212> TYPE: PRT
<213> ORGANISM: Staphylococcus aureus

<400> SEQUENCE: 18

```
Met Met Lys Ala Thr Lys Leu Val Leu Gly Ala Val Ile Leu Gly Ser
1               5                   10                  15
Thr Leu Leu Ala Gly Cys Gly Asn Gln Gly Glu Lys Asn Asn Lys Ala
            20                  25                  30
Glu Thr Lys Ser Tyr Lys Met Asp Asp Gly Lys Thr Val Asp Ile Pro
        35                  40                  45
Lys Asp Pro Lys Arg Ile Ala Val Val Ala Pro Thr Tyr Ala Gly Gly
    50                  55                  60
Leu Lys Lys Leu Gly Ala Asn Ile Val Ala Val Asn Gln Gln Val Asp
```

```
                65                  70                  75                  80
        Gln Ser Lys Val Leu Lys Asp Lys Phe Lys Gly Val Thr Lys Ile Gly
                        85                  90                  95

Asp Gly Asp Val Glu Lys Val Ala Lys Glu Lys Pro Asp Leu Ile Ile
                        100                 105                 110

Val Tyr Ser Thr Asp Lys Asp Ile Lys Lys Tyr Gln Lys Val Ala Pro
                        115                 120                 125

Thr Val Val Asp Tyr Asn Lys His Lys Tyr Leu Glu Gln Gln Glu
                130                 135                 140

Met Leu Gly Lys Ile Val Gly Lys Glu Asp Lys Val Lys Ala Trp Lys
        145                 150                 155                 160

Lys Asp Trp Glu Glu Thr Thr Ala Lys Asp Gly Lys Glu Ile Lys Lys
                        165                 170                 175

Ala Ile Gly Gln Asp Ala Thr Val Ser Leu Phe Asp Glu Phe Asp Lys
                        180                 185                 190

Lys Leu Tyr Thr Tyr Gly Asp Asn Trp Gly Arg Gly Gly Glu Val Leu
                        195                 200                 205

Tyr Gln Ala Phe Gly Leu Lys Met Gln Pro Glu Gln Gln Lys Leu Thr
                210                 215                 220

Ala Lys Ala Gly Trp Ala Glu Val Lys Gln Glu Ile Glu Lys Tyr
        225                 230                 235                 240

Ala Gly Asp Tyr Ile Val Ser Thr Ser Glu Gly Lys Pro Thr Pro Gly
                        245                 250                 255

Tyr Glu Ser Thr Asn Met Trp Lys Asn Leu Lys Ala Thr Lys Glu Gly
                        260                 265                 270

His Ile Val Lys Val Asp Ala Gly Thr Tyr Trp Tyr Asn Asp Pro Tyr
                        275                 280                 285

Thr Leu Asp Phe Met Arg Lys Asp Leu Lys Glu Lys Leu Ile Lys Ala
                290                 295                 300

Ala Lys
        305

<210> SEQ ID NO 19
<211> LENGTH: 293
<212> TYPE: PRT
<213> ORGANISM: Staphylococcus aureus

<400> SEQUENCE: 19

Ala Asp Ser Asp Ile Asn Ile Lys Thr Gly Thr Thr Asp Ile Gly Ser
        1               5                   10                  15

Asn Thr Thr Val Lys Thr Gly Asp Leu Val Thr Tyr Asp Lys Glu Asn
                        20                  25                  30

Gly Met Leu Lys Lys Val Phe Tyr Ser Phe Ile Asp Asp Lys Asn His
                        35                  40                  45

Asn Lys Lys Leu Leu Val Ile Arg Thr Lys Gly Thr Ile Ala Gly Gln
                50                  55                  60

Tyr Arg Val Tyr Ser Glu Gly Ala Asn Lys Ser Gly Leu Ala Trp
        65                  70                  75                  80

Pro Ser Ala Phe Lys Val Gln Leu Gln Leu Pro Asp Asn Glu Val Ala
                        85                  90                  95

Gln Ile Ser Asp Tyr Tyr Pro Arg Asn Ser Ile Asp Thr Lys Glu Tyr
                        100                 105                 110

Met Ser Thr Leu Thr Tyr Gly Phe Asn Gly Asn Val Thr Gly Asp Asp
                        115                 120                 125
```

```
Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
        290

<210> SEQ ID NO 20
<211> LENGTH: 314
<212> TYPE: PRT
<213> ORGANISM: Staphylococcus aureus

<400> SEQUENCE: 20

Met Lys Ala Thr Lys Leu Val Leu Gly Ala Val Ile Leu Gly Ser Thr
1               5                   10                  15

Leu Leu Ala Gly Cys Ala Asp Ser Asp Ile Asn Ile Lys Thr Gly Thr
            20                  25                  30

Thr Asp Ile Gly Ser Asn Thr Thr Val Lys Thr Gly Asp Leu Val Thr
        35                  40                  45

Tyr Asp Lys Glu Asn Gly Met Leu Lys Lys Val Phe Tyr Ser Phe Ile
50                  55                  60

Asp Asp Lys Asn His Asn Lys Lys Leu Leu Val Ile Arg Thr Lys Gly
65                  70                  75                  80

Thr Ile Ala Gly Gln Tyr Arg Val Tyr Ser Glu Glu Gly Ala Asn Lys
                85                  90                  95

Ser Gly Leu Ala Trp Pro Ser Ala Phe Lys Val Gln Leu Gln Leu Pro
            100                 105                 110

Asp Asn Glu Val Ala Gln Ile Ser Asp Tyr Tyr Pro Arg Asn Ser Ile
        115                 120                 125

Asp Thr Lys Glu Tyr Met Ser Thr Leu Thr Tyr Gly Phe Asn Gly Asn
    130                 135                 140

Val Thr Gly Asp Asp Thr Gly Lys Ile Gly Gly Leu Ile Gly Ala Asn
145                 150                 155                 160

Val Ser Ile Gly His Thr Leu Lys Tyr Val Gln Pro Asp Phe Lys Thr
                165                 170                 175

Ile Leu Glu Ser Pro Thr Asp Lys Lys Val Gly Trp Lys Val Ile Phe
            180                 185                 190

Asn Asn Met Val Asn Gln Asn Trp Gly Pro Tyr Asp Arg Asp Ser Trp
        195                 200                 205
```

```
Asn Pro Val Tyr Gly Asn Gln Leu Phe Met Lys Thr Arg Asn Gly Ser
            210                 215                 220

Met Lys Ala Ala Asp Asn Phe Leu Asp Pro Asn Lys Ala Ser Ser Leu
225                 230                 235                 240

Leu Ser Ser Gly Phe Ser Pro Asp Phe Ala Thr Val Ile Thr Met Asp
                    245                 250                 255

Arg Lys Ala Ser Lys Gln Gln Thr Asn Ile Asp Val Ile Tyr Glu Arg
                260                 265                 270

Val Arg Asp Asp Tyr Gln Leu His Trp Thr Ser Thr Asn Trp Lys Gly
                275                 280                 285

Thr Asn Thr Lys Asp Lys Trp Ile Asp Arg Ser Ser Glu Arg Tyr Lys
            290                 295                 300

Ile Asp Trp Glu Lys Glu Glu Met Thr Asn
305                 310

<210> SEQ ID NO 21
<211> LENGTH: 291
<212> TYPE: PRT
<213> ORGANISM: Staphylococcus aureus

<400> SEQUENCE: 21

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
```

260                 265                 270
Val Ser Lys Glu Ile Leu Ala Glu Ala Lys Lys Leu Asn Asp Ala Gln
            275                 280                 285

Ala Pro Lys
        290

<210> SEQ ID NO 22
<211> LENGTH: 312
<212> TYPE: PRT
<213> ORGANISM: Staphylococcus aureus

<400> SEQUENCE: 22

Met Lys Ala Thr Lys Leu Val Leu Gly Ala Val Ile Leu Gly Ser Thr
1               5                   10                  15

Leu Leu Ala Gly Cys Ala Gln His Asp Glu Ala Lys Lys Asn Ala Phe
            20                  25                  30

Tyr Gln Val Leu Asn Met Pro Asn Leu Asn Ala Asp Gln Arg Asn Gly
            35                  40                  45

Phe Ile Gln Ser Leu Lys Ala Ala Pro Ser Gln Ser Ala Asn Val Leu
        50                  55                  60

Gly Glu Ala Gln Lys Leu Asn Asp Ser Gln Ala Pro Lys Ala Asp Ala
65                  70                  75                  80

Lys Arg Asn Asn Phe Asn Lys Asp Lys Lys Ser Ala Phe Tyr Glu Ile
                85                  90                  95

Leu Asn Met Pro Asn Leu Asn Glu Ala Gln Arg Asn Gly Phe Ile Gln
            100                 105                 110

Ser Leu Lys Ala Ala Pro Ser Gln Ser Thr Asn Val Leu Gly Glu Ala
        115                 120                 125

Lys Lys Leu Asn Glu Ser Gln Ala Pro Lys Ala Asp Asn Asn Phe Asn
130                 135                 140

Lys Glu Lys Lys Asn Ala Phe Tyr Glu Ile Leu Asn Met Pro Asn Leu
145                 150                 155                 160

Asn Glu Glu Gln Arg Asn Gly Phe Ile Gln Ser Leu Lys Ala Ala Pro
                165                 170                 175

Ser Gln Ser Ala Asn Leu Leu Ser Glu Ala Lys Lys Leu Asn Glu Ser
            180                 185                 190

Gln Ala Pro Lys Ala Asp Asn Lys Phe Asn Lys Glu Lys Lys Asn Ala
        195                 200                 205

Phe Tyr Glu Ile Leu His Leu Pro Asn Leu Asn Glu Glu Gln Arg Asn
    210                 215                 220

Gly Phe Ile Gln Ser Leu Lys Ala Ala Pro Ser Gln Ser Ala Asn Leu
225                 230                 235                 240

Leu Ala Glu Ala Lys Lys Leu Asn Asp Ala Gln Ala Pro Lys Ala Asp
                245                 250                 255

Asn Lys Phe Asn Lys Glu Lys Lys Asn Ala Phe Tyr Glu Ile Leu His
            260                 265                 270

Leu Pro Asn Leu Thr Glu Glu Gln Arg Asn Gly Phe Ile Gln Ser Leu
        275                 280                 285

Lys Ala Ala Pro Ser Val Ser Lys Glu Ile Leu Ala Glu Ala Lys Lys
    290                 295                 300

Leu Asn Asp Ala Gln Ala Pro Lys
305                 310

<210> SEQ ID NO 23
<211> LENGTH: 283

```
<212> TYPE: PRT
<213> ORGANISM: Staphylococcus aureus

<400> SEQUENCE: 23

Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
            20                  25                  30

Phe Asp Phe Val Lys Asp Lys Lys Tyr Asn Lys Asp Ala Leu Ile Val
        35                  40                  45

Lys Met Gln Gly Phe Ile Asn Ser Arg Thr Ser Phe Ser Asp Val Lys
    50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
                85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
    130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gln Ser Pro Asn Gly Pro Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
                245                 250                 255

Asn Ala Phe Val Asn Arg Asn Phe Val Val Arg Tyr Glu Val Asn Trp
            260                 265                 270

Lys Thr His Glu Ile Lys Val Lys Gly His Asn
        275                 280

<210> SEQ ID NO 24
<211> LENGTH: 304
<212> TYPE: PRT
<213> ORGANISM: Staphylococcus aureus

<400> SEQUENCE: 24

Met Lys Ala Thr Lys Leu Val Leu Gly Ala Val Ile Leu Gly Ser Thr
1               5                   10                  15

Leu Leu Ala Gly Cys Asn Thr Asn Ile Glu Asn Ile Gly Asp Gly Ala
            20                  25                  30

Glu Val Ile Lys Arg Thr Glu Asp Val Ser Ser Lys Lys Trp Gly Val
        35                  40                  45

Thr Gln Asn Val Gln Phe Asp Phe Val Lys Asp Lys Lys Tyr Asn Lys
    50                  55                  60
```

-continued

```
Asp Ala Leu Ile Val Lys Met Gln Gly Phe Ile Asn Ser Arg Thr Ser
 65                  70                  75                  80

Phe Ser Asp Val Lys Gly Ser Gly Tyr Glu Leu Thr Lys Arg Met Ile
                 85                  90                  95

Trp Pro Phe Gln Tyr Asn Ile Gly Leu Thr Thr Lys Asp Pro Asn Val
            100                 105                 110

Ser Leu Ile Asn Tyr Leu Pro Lys Asn Lys Ile Glu Thr Thr Asp Val
        115                 120                 125

Gly Gln Thr Leu Gly Tyr Asn Ile Gly Gly Asn Phe Gln Ser Ala Pro
    130                 135                 140

Ser Ile Gly Gly Asn Gly Ser Phe Asn Tyr Ser Lys Thr Ile Ser Tyr
145                 150                 155                 160

Thr Gln Lys Ser Tyr Val Ser Glu Val Asp Lys Gln Asn Ser Lys Ser
                165                 170                 175

Val Lys Trp Gly Val Lys Ala Asn Glu Phe Val Thr Pro Asp Gly Lys
            180                 185                 190

Lys Ser Ala His Asp Arg Tyr Leu Phe Val Gln Ser Pro Asn Gly Pro
        195                 200                 205

Thr Gly Ser Ala Arg Glu Tyr Phe Ala Pro Asp Asn Gln Leu Pro Pro
    210                 215                 220

Leu Val Gln Ser Gly Phe Asn Pro Ser Phe Ile Thr Thr Leu Ser His
225                 230                 235                 240

Glu Lys Gly Ser Ser Asp Thr Ser Glu Phe Glu Ile Ser Tyr Gly Arg
                245                 250                 255

Asn Leu Asp Ile Thr Tyr Ala Thr Leu Phe Pro Arg Thr Gly Ile Tyr
            260                 265                 270

Ala Glu Arg Lys His Asn Ala Phe Val Asn Arg Asn Phe Val Val Arg
        275                 280                 285

Tyr Glu Val Asn Trp Lys Thr His Glu Ile Lys Val Lys Gly His Asn
    290                 295                 300

<210> SEQ ID NO 25
<211> LENGTH: 381
<212> TYPE: PRT
<213> ORGANISM: Artificial Sequence
<220> FEATURE:
<223> OTHER INFORMATION: FhuD2-hFAT1 fusion protein

<400> SEQUENCE: 25

Met Met Lys Ala Thr Lys Leu Val Leu Gly Ala Val Ile Leu Gly Ser
 1               5                  10                  15

Thr Leu Leu Ala Gly Cys Gly Asn Gln Gly Glu Lys Asn Asn Lys Ala
                20                  25                  30

Glu Thr Lys Ser Tyr Lys Met Asp Asp Gly Lys Thr Val Asp Ile Pro
            35                  40                  45

Lys Asp Pro Lys Arg Ile Ala Val Val Ala Pro Thr Tyr Ala Gly Gly
        50                  55                  60

Leu Lys Lys Leu Gly Ala Asn Ile Val Ala Val Asn Gln Gln Val Asp
 65                  70                  75                  80

Gln Ser Lys Val Leu Lys Asp Lys Phe Lys Gly Val Thr Lys Ile Gly
                 85                  90                  95

Asp Gly Asp Val Glu Lys Val Ala Lys Glu Lys Pro Asp Leu Ile Ile
            100                 105                 110

Val Tyr Ser Thr Asp Lys Asp Ile Lys Lys Tyr Gln Lys Val Ala Pro
        115                 120                 125
```

Thr Val Val Asp Tyr Asn Lys His Lys Tyr Leu Glu Gln Gln Glu
    130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
        195                 200                 205

Tyr Gln Ala Phe Gly Leu Lys Met Gln Pro Glu Gln Gln Lys Leu Thr
    210                 215                 220

Ala Lys Ala Gly Trp Ala Glu Val Lys Gln Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
    290                 295                 300

Ala Lys Ile Gln Val Glu Ala Thr Asp Lys Asp Leu Gly Pro Asn Gly
305                 310                 315                 320

His Val Thr Tyr Ser Ile Val Thr Asp Thr Asp Ile Gln Val Glu Ala
                325                 330                 335

Thr Asp Lys Asp Leu Gly Pro Asn Gly His Val Thr Tyr Ser Ile Val
            340                 345                 350

Thr Asp Thr Asp Ile Gln Val Glu Ala Thr Asp Lys Asp Leu Gly Pro
        355                 360                 365

Asn Gly His Val Thr Tyr Ser Ile Val Thr Asp Thr Asp
    370                 375                 380

<210> SEQ ID NO 26
<211> LENGTH: 381
<212> TYPE: PRT
<213> ORGANISM: Artificial Sequence
<220> FEATURE:
<223> OTHER INFORMATION: FhuD2-mFAT1 fusion protein

<400> SEQUENCE: 26

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
            20                  25                  30

Glu Thr Lys Ser Tyr Lys Met Asp Asp Gly Lys Thr Val Asp Ile Pro
        35                  40                  45

Lys Asp Pro Lys Arg Ile Ala Val Val Ala Pro Thr Tyr Ala Gly Gly
    50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
            100                 105                 110

```
Val Tyr Ser Thr Asp Lys Asp Ile Lys Lys Tyr Gln Lys Val Ala Pro
            115                 120                 125

Thr Val Val Asp Tyr Asn Lys His Lys Tyr Leu Glu Gln Gln Glu
130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
        195                 200                 205

Tyr Gln Ala Phe Gly Leu Lys Met Gln Pro Glu Gln Gln Lys Leu Thr
    210                 215                 220

Ala Lys Ala Gly Trp Ala Glu Val Lys Gln Glu Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
    290                 295                 300

Ala Lys Ile Gln Val Glu Ala Thr Asp Lys Asp Leu Gly Pro Ser Gly
305                 310                 315                 320

His Val Thr Tyr Ala Ile Leu Thr Asp Thr Glu Ile Gln Val Glu Ala
                325                 330                 335

Thr Asp Lys Asp Leu Gly Pro Ser Gly His Val Thr Tyr Ala Ile Leu
            340                 345                 350

Thr Asp Thr Glu Ile Gln Val Glu Ala Thr Asp Lys Asp Leu Gly Pro
        355                 360                 365

Ser Gly His Val Thr Tyr Ala Ile Leu Thr Asp Thr Glu
    370                 375                 380

<210> SEQ ID NO 27
<211> LENGTH: 353
<212> TYPE: PRT
<213> ORGANISM: Artificial Sequence
<220> FEATURE:
<223> OTHER INFORMATION: FhuD2-EGFRviii fusion protein

<400> SEQUENCE: 27

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
            20                  25                  30

Glu Thr Lys Ser Tyr Lys Met Asp Asp Gly Lys Thr Val Asp Ile Pro
        35                  40                  45

Lys Asp Pro Lys Arg Ile Ala Val Val Ala Pro Thr Tyr Ala Gly Gly
    50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95
```

```
Asp Gly Asp Val Glu Lys Val Ala Lys Glu Lys Pro Asp Leu Ile Ile
            100                 105                 110

Val Tyr Ser Thr Asp Lys Asp Ile Lys Lys Tyr Gln Lys Val Ala Pro
        115                 120                 125

Thr Val Val Asp Tyr Asn Lys His Lys Tyr Leu Glu Gln Gln Glu
    130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Glu Val Leu
        195                 200                 205

Tyr Gln Ala Phe Gly Leu Lys Met Gln Pro Glu Gln Gln Lys Leu Thr
    210                 215                 220

Ala Lys Ala Gly Trp Ala Glu Val Lys Gln Glu Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
    290                 295                 300

Ala Lys Gly Ser Leu Glu Glu Lys Lys Gly Asn Tyr Val Val Thr Asp
305                 310                 315                 320

His Ser Gly Leu Glu Glu Lys Lys Gly Asn Tyr Val Val Thr Asp His
                325                 330                 335

Gly Ser Leu Glu Glu Lys Lys Gly Asn Tyr Val Val Thr Asp His Ser
            340                 345                 350

Gly

<210> SEQ ID NO 28
<211> LENGTH: 333
<212> TYPE: PRT
<213> ORGANISM: Artificial Sequence
<220> FEATURE:
<223> OTHER INFORMATION: FhuD2-M03 fusion protein

<400> SEQUENCE: 28

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
            20                  25                  30

Glu Thr Lys Ser Tyr Lys Met Asp Asp Gly Lys Thr Val Asp Ile Pro
        35                  40                  45

Lys Asp Pro Lys Arg Ile Ala Val Val Ala Pro Thr Tyr Ala Gly Gly
    50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
```

```
            100                 105                 110
Val Tyr Ser Thr Asp Lys Asp Ile Lys Lys Tyr Gln Lys Val Ala Pro
            115                 120                 125

Thr Val Val Val Asp Tyr Asn Lys His Lys Tyr Leu Glu Gln Gln Glu
        130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
        195                 200                 205

Tyr Gln Ala Phe Gly Leu Lys Met Gln Pro Glu Gln Gln Lys Leu Thr
    210                 215                 220

Ala Lys Ala Gly Trp Ala Glu Val Lys Gln Glu Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
    290                 295                 300

Ala Lys Asp Lys Pro Leu Arg Arg Asn Asn Ser Tyr Thr Ser Tyr Ile
305                 310                 315                 320

Met Ala Ile Cys Gly Met Pro Leu Asp Ser Phe Arg Ala
                325                 330

<210> SEQ ID NO 29
<211> LENGTH: 333
<212> TYPE: PRT
<213> ORGANISM: Artificial Sequence
<220> FEATURE:
<223> OTHER INFORMATION: FhuD2-M20 fusion protein

<400> SEQUENCE: 29

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
            20                  25                  30

Glu Thr Lys Ser Tyr Lys Met Asp Asp Gly Lys Thr Val Asp Ile Pro
        35                  40                  45

Lys Asp Pro Lys Arg Ile Ala Val Ala Pro Thr Tyr Ala Gly Gly
    50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
            100                 105                 110

Val Tyr Ser Thr Asp Lys Asp Ile Lys Lys Tyr Gln Lys Val Ala Pro
            115                 120                 125

Thr Val Val Val Asp Tyr Asn Lys His Lys Tyr Leu Glu Gln Gln Glu
```

```
                130             135                 140
Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
                180                 185                 190

Lys Leu Tyr Thr Tyr Gly Asp Asn Trp Gly Arg Gly Gly Glu Val Leu
                195                 200                 205

Tyr Gln Ala Phe Gly Leu Lys Met Gln Pro Glu Gln Gln Lys Leu Thr
                210                 215                 220

Ala Lys Ala Gly Trp Ala Glu Val Lys Gln Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
                260                 265                 270

His Ile Val Lys Val Asp Ala Gly Thr Tyr Trp Tyr Asn Asp Pro Tyr
                275                 280                 285

Thr Leu Asp Phe Met Arg Lys Asp Leu Lys Glu Lys Leu Ile Lys Ala
290                 295                 300

Ala Lys Pro Leu Leu Pro Phe Tyr Pro Pro Asp Glu Ala Leu Glu Ile
305                 310                 315                 320

Gly Leu Glu Leu Asn Ser Ser Ala Leu Pro Pro Thr Glu
                325                 330

<210> SEQ ID NO 30
<211> LENGTH: 333
<212> TYPE: PRT
<213> ORGANISM: Artificial Sequence
<220> FEATURE:
<223> OTHER INFORMATION: FhuD2-M26 fusion protein

<400> SEQUENCE: 30

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
                20                  25                  30

Glu Thr Lys Ser Tyr Lys Met Asp Asp Gly Lys Thr Val Asp Ile Pro
                35                  40                  45

Lys Asp Pro Lys Arg Ile Ala Val Val Ala Pro Thr Tyr Ala Gly Gly
50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
                100                 105                 110

Val Tyr Ser Thr Asp Lys Asp Ile Lys Lys Tyr Gln Lys Val Ala Pro
                115                 120                 125

Thr Val Val Val Asp Tyr Asn Lys His Lys Tyr Leu Glu Gln Gln Glu
                130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
```

```
                165                 170                 175
Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
        195                 200                 205

Tyr Gln Ala Phe Gly Leu Lys Met Gln Pro Glu Gln Lys Leu Thr
    210                 215                 220

Ala Lys Ala Gly Trp Ala Glu Val Lys Gln Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
    290                 295                 300

Ala Lys Val Ile Leu Pro Gln Ala Pro Ser Gly Pro Ser Tyr Ala Thr
305                 310                 315                 320

Tyr Leu Gln Pro Ala Gln Ala Gln Met Leu Thr Pro Pro
                325                 330
```

<210> SEQ ID NO 31
<211> LENGTH: 333
<212> TYPE: PRT
<213> ORGANISM: Artificial Sequence
<220> FEATURE:
<223> OTHER INFORMATION: FhuD2-M27 fusion protein

<400> SEQUENCE: 31

```
Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
                20                  25                  30

Glu Thr Lys Ser Tyr Lys Met Asp Asp Gly Lys Thr Val Asp Ile Pro
            35                  40                  45

Lys Asp Pro Lys Arg Ile Ala Val Val Ala Pro Thr Tyr Ala Gly Gly
    50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
            100                 105                 110

Val Tyr Ser Thr Asp Lys Asp Ile Lys Lys Tyr Gln Lys Val Ala Pro
    115                 120                 125

Thr Val Val Asp Tyr Asn Lys His Lys Tyr Leu Glu Gln Gln Glu
    130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
```

```
                195                 200                 205
Tyr Gln Ala Phe Gly Leu Lys Met Gln Pro Glu Gln Gln Lys Leu Thr
            210                 215                 220

Ala Lys Ala Gly Trp Ala Glu Val Lys Gln Glu Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
                260                 265                 270

His Ile Val Lys Val Asp Ala Gly Thr Tyr Trp Tyr Asn Asp Pro Tyr
                275                 280                 285

Thr Leu Asp Phe Met Arg Lys Asp Leu Lys Glu Lys Leu Ile Lys Ala
                290                 295                 300

Ala Lys Glu His Ile His Arg Ala Gly Gly Leu Phe Val Ala Asp Ala
305                 310                 315                 320

Ile Gln Val Gly Phe Gly Arg Ile Gly Lys His Phe Trp
                325                 330
```

<210> SEQ ID NO 32
<211> LENGTH: 333
<212> TYPE: PRT
<213> ORGANISM: Artificial Sequence
<220> FEATURE:
<223> OTHER INFORMATION: FhuD2-M68 fusion protein

<400> SEQUENCE: 32

```
Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
                20                  25                  30

Glu Thr Lys Ser Tyr Lys Met Asp Asp Gly Lys Thr Val Asp Ile Pro
            35                  40                  45

Lys Asp Pro Lys Arg Ile Ala Val Val Ala Pro Thr Tyr Ala Gly Gly
50                  55                  60

Leu Lys Lys Leu Gly Ala Asn Ile Val Ala Val Asn Gln Gln Val Asp
65                  70                  75                  80

Gln Ser Lys Val Leu Lys Asp Lys Phe Lys Gly Val Thr Lys Ile Gly
                85                  90                  95

Asp Gly Asp Val Glu Lys Val Ala Lys Glu Lys Pro Asp Leu Ile Ile
                100                 105                 110

Val Tyr Ser Thr Asp Lys Asp Ile Lys Lys Tyr Gln Lys Val Ala Pro
            115                 120                 125

Thr Val Val Val Asp Tyr Asn Lys His Lys Tyr Leu Glu Gln Gln Glu
            130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
                180                 185                 190

Lys Leu Tyr Thr Tyr Gly Asp Asn Trp Gly Arg Gly Gly Glu Val Leu
            195                 200                 205

Tyr Gln Ala Phe Gly Leu Lys Met Gln Pro Glu Gln Gln Lys Leu Thr
            210                 215                 220

Ala Lys Ala Gly Trp Ala Glu Val Lys Gln Glu Glu Ile Glu Lys Tyr
225                 230                 235                 240
```

```
                    225                 230                 235                 240
Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
                260                 265                 270

His Ile Val Lys Val Asp Ala Gly Thr Tyr Trp Tyr Asn Asp Pro Tyr
                275                 280                 285

Thr Leu Asp Phe Met Arg Lys Asp Leu Lys Glu Lys Leu Ile Lys Ala
                290                 295                 300

Ala Lys Val Thr Ser Ile Pro Ser Val Ser Asn Ala Leu Asn Trp Lys
305                 310                 315                 320

Glu Phe Ser Phe Ile Gln Ser Thr Leu Gly Tyr Val Ala
                325                 330

<210> SEQ ID NO 33
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 33
catcaccatc accatcacga ttaca                                             25

<210> SEQ ID NO 34
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 34
gctggagcaa cctgccagca gag                                               23

<210> SEQ ID NO 35
<211> LENGTH: 43
<212> TYPE: DNA
<213> ORGANISM: Artificial Sequence
<220> FEATURE:
<223> OTHER INFORMATION: oligonucleotide primer

<400> SEQUENCE: 35
ctgctggcag gttgcgggaa ccaaggtgaa aaaataaca aag                          43

<210> SEQ ID NO 36
<211> LENGTH: 53
<212> TYPE: DNA
<213> ORGANISM: Artificial Sequence
<220> FEATURE:
<223> OTHER INFORMATION: oligonucleotide primer

<400> SEQUENCE: 36
gtgatggtga tgttatttttg cagctttaat taattttttct tttaaatctt tac            53

<210> SEQ ID NO 37
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 37
ctgctggcag gttgcgcaga ttctgatatt aatattaaaa ccggt                       45
```

<210> SEQ ID NO 38
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 38
gtgatggtga tgttaatttg tcatttcttc tttttcccaa tcgat          45

<210> SEQ ID NO 39
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 39
ctgctggcag gttgcgcaca gcatgatgaa gccaaaaaa                 39

<210> SEQ ID NO 40
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 40
gtgatggtga tgttatttag gtgcctgtgc gtcgtt                    36

<210> SEQ ID NO 41
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 41
ctgctggcag gttgcaatac taatattgaa aatattggtg atggtgc        47

<210> SEQ ID NO 42
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 42
gtgatggtga tgttaattat gtcctttcac tttaatttcg tgtgttttcc a   51

<210> SEQ ID NO 43
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 43
atccaagtgg aggcgaccga taaagacctg ggtccgtcgg ggcatgtg       48

<210> SEQ ID NO 44
<211> LENGTH: 51
<212> TYPE: DNA
<213> ORGANISM: Artificial Sequence
<220> FEATURE:

<223> OTHER INFORMATION: oligonucleotide primer

<400> SEQUENCE: 44
aacctgaatt tcggtgtcgg tcaggatggc atacgtcaca tgccccgacg g          51

<210> SEQ ID NO 45
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 45
accgaaattc aggttgaagc caccgacaaa gacttaggcc cgagtggtca c          51

<210> SEQ ID NO 46
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 46
ctgaatttca gtatcggtga gaatcgcgta ggtcacgtga ccactcgggc c          51

<210> SEQ ID NO 47
<211> LENGTH: 51
<212> TYPE: DNA
<213> ORGANISM: Artificial Sequence
<220> FEATURE:
<223> OTHER INFORMATION: oligonucleotide primer

<400> SEQUENCE: 47
gatactgaaa ttcaggttga agctaccgat aaagatttgg gcccgagtgg t          51

<210> SEQ ID NO 48
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 48
ttcagtatcc gtgaggatcg cataggttac atgaccactc gggcccaa             48

<210> SEQ ID NO 49
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 49
catcaccatc accatcacga ttaca                                      25

<210> SEQ ID NO 50
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 50
taattaaagc tgcaaaaatt caagtggaag cgactga                         37

<210> SEQ ID NO 51
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 51
gatggtgatg gtgatgtcaa tctgtatcgg taacaatag                     39

<210> SEQ ID NO 52
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 52
taattaaagc tgcaaaaatc caagtggagg cgaccga                       37

<210> SEQ ID NO 53
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 53
gatggtgatg gtgatgtcat tcagtatccg tgaggatcg                     39

<210> SEQ ID NO 54
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 54
taattaaagc tgcaaaaggt tccctggaag aaaagaag                      38

<210> SEQ ID NO 55
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 55
gatggtgatg gtgatgtcag ccggaatggt cggtaaccac                    40

<210> SEQ ID NO 56
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 56
ttttgcagct ttaattaatt tttc                                     24

<210> SEQ ID NO 57
<211> LENGTH: 25
<212> TYPE: DNA
<213> ORGANISM: Artificial Sequence
<220> FEATURE:
<223> OTHER INFORMATION: oligonucleotide primer

```
<400> SEQUENCE: 57
catcaccatc accatcacga ttaca                                        25

<210> SEQ ID NO 58
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 58
ttttgcagct ttaattaatt tttc                                         24

<210> SEQ ID NO 59
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 59
taattaaagc tgcaaaagac aagcccttac gtcgc                             35

<210> SEQ ID NO 60
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 60
gatggtgatg gtgatgtcag gcacgaaagc tatcaagtgg                        40

<210> SEQ ID NO 61
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 61
taattaaagc tgcaaaacct cttttaccttt tttatccacc                        40

<210> SEQ ID NO 62
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 62
gatggtgatg gtgatgtcat tctgtgggtg gcaacgc                           37

<210> SEQ ID NO 63
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 63
taattaaagc tgcaaaagta attcttcccc aggccc                            36

<210> SEQ ID NO 64
<211> LENGTH: 40
```

```
<212> TYPE: DNA
<213> ORGANISM: Artificial Sequence
<220> FEATURE:
<223> OTHER INFORMATION: oligonucleotide primer

<400> SEQUENCE: 64
gatggtgatg gtgatgtcaa ggaggtgtta acatctgcgc                           40

<210> SEQ ID NO 65
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 65
taattaaagc tgcaaaagag catattcatc gtgctggtg                            39

<210> SEQ ID NO 66
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 66
gatggtgatg gtgatgtcac cagaaatgct taccgatgcg                           40

<210> SEQ ID NO 67
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 67
taattaaagc tgcaaaagta acaagcatcc catccgtctc                           40

<210> SEQ ID NO 68
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 68
gatggtgatg gtgatgtcag gccacgtagc ccaaggtac                            39

<210> SEQ ID NO 69
<211> LENGTH: 15
<212> TYPE: PRT
<213> ORGANISM: Artificial Sequence
<220> FEATURE:
<223> OTHER INFORMATION: synthetic peptide

<400> SEQUENCE: 69

Met Asp Asp Gly Lys Thr Val Asp Ile Pro Lys Asp Pro Lys Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: synthetic peptide

<400> SEQUENCE: 70
```

Cys Gly Thr Asn Thr Lys Asp Lys Trp Ile Asp Arg Ser Ser Glu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: synthetic peptide

<400> SEQUENCE: 71

Cys Asn Glu Phe Val Thr Pro Asp Gly Lys Lys Ser Ala His Asp
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: synthetic peptide

<400> SEQUENCE: 72

Cys Ala Lys Lys Leu Asn Asp Ala Gln Ala Pro Lys Ala Asp Asn
1               5                   10                  15

<210> SEQ ID NO 73
<211> LENGTH: 25
<212> TYPE: PRT
<213> ORGANISM: Artificial Sequence
<220> FEATURE:
<223> OTHER INFORMATION: synthetic peptide

<400> SEQUENCE: 73

Ile Gln Val Glu Ala Thr Asp Lys Asp Leu Gly Pro Asn Gly His Val
1               5                   10                  15

Thr Tyr Ser Ile Val Thr Asp Thr Asp
            20                  25

<210> SEQ ID NO 74
<211> LENGTH: 25
<212> TYPE: PRT
<213> ORGANISM: Artificial Sequence
<220> FEATURE:
<223> OTHER INFORMATION: synthetic peptide

<400> SEQUENCE: 74

Ile Gln Val Glu Ala Thr Asp Lys Asp Leu Gly Pro Ser Gly His Val
1               5                   10                  15

Thr Tyr Ala Ile Leu Thr Asp Thr Glu
            20                  25

<210> SEQ ID NO 75
<211> LENGTH: 14
<212> TYPE: PRT
<213> ORGANISM: Artificial Sequence
<220> FEATURE:
<223> OTHER INFORMATION: synthetic peptide

<400> SEQUENCE: 75

Leu Glu Glu Lys Lys Gly Asn Tyr Val Val Thr Asp His Cys
1               5                   10

<210> SEQ ID NO 76
<211> LENGTH: 21
<212> TYPE: PRT

<213> ORGANISM: Unknown
<220> FEATURE:
<223> OTHER INFORMATION: murein lipoprotein lpp

<400> SEQUENCE: 76

Met Lys Ala Thr Lys Leu Val Leu Gly Ala Val Ile Leu Gly Ser Thr
1               5                   10                  15

Leu Leu Ala Gly Cys
            20

<210> SEQ ID NO 77
<211> LENGTH: 1050
<212> TYPE: DNA
<213> ORGANISM: Artificial Sequence
<220> FEATURE:
<223> OTHER INFORMATION: FhuD2-OVA-3X fusion protein encoding sequence

<400> SEQUENCE: 77

```
atgatgaaag ctactaaact ggtactgggc gcggtaatcc tgggttctac tctgctggca    60
ggttgcggga accaaggtga aaaaataac aaagctgaaa ctaaatctta taaaatggac   120
gatggcaaaa cggtagatat tccgaaagac cctaaacgca ttgcagtagt tgcgccaaca   180
tatgctggtg gacttaaaaa attaggtgca aacattgtag ctgtaaatca acaagtcgat   240
caaagcaaag tattaaaaga taaatttaaa ggtgttacaa aaattggtga tggcgatgta   300
gaaaaagttg ctaagaaaaa gccagattta attattgtat actctactga caaagatatt   360
aaaaaatatc aaaaagtagc accaacagta gttgttgact ataataagca taaatattta   420
gaacaacaag aaatgttagg gaaaattgtt ggtaaagaag ataaagtaaa agcttggaag   480
aaagattggg aagaaacaac tgctaaagac ggtaaagaaa ttaaaaaagc aattggacaa   540
gatgcaacag tgtcattgtt tgatgaattt gataaaaaat tatacactta cggcgataac   600
tggggtcgtg gtggagaagt attatatcaa gcatttggtt tgaaaatgca accagaacaa   660
caaaagttaa ctgcaaaagc aggttgggct gaagtgaaac aagaagaaat tgaaaaatat   720
gctggtgatt acattgtgag tacaagtgaa ggtaaaccta caccaggata cgaatcaaca   780
aacatgtgga gaatttgaa agctactaaa gaaggacata ttgttaaagt tgatgctggt   840
acatactggt acaacgatcc ttatacatta gatttcatgc gtaaagattt aaaagaaaaa   900
ttaattaaag ctgcaaaaca gctggaaagc attattaact ttgaaaaact gaccgaaggt   960
ggtcagctgg aaagcattat taactttgaa aaactgaccg aaggtggtca gctggaaagc  1020
atcatcaact cgaaaaact gaccgaataa                                    1050
```

<210> SEQ ID NO 78
<211> LENGTH: 349
<212> TYPE: PRT
<213> ORGANISM: Artificial Sequence
<220> FEATURE:
<223> OTHER INFORMATION: FhuD2-OVA-3X fusion protein amino acid sequence

<400> SEQUENCE: 78

Met Met Lys Ala Thr Lys Leu Val Leu Gly Ala Val Ile Leu Gly Ser
1               5                   10                  15

Thr Leu Leu Ala Gly Cys Gly Asn Gln Gly Glu Lys Asn Asn Lys Ala
                20                  25                  30

Glu Thr Lys Ser Tyr Lys Met Asp Asp Gly Lys Thr Val Asp Ile Pro
            35                  40                  45

Lys Asp Pro Lys Arg Ile Ala Val Val Ala Pro Thr Tyr Ala Gly Gly
        50                  55                  60

Leu Lys Lys Leu Gly Ala Asn Ile Val Ala Val Asn Gln Gln Val Asp
 65                  70                  75                  80

Gln Ser Lys Val Leu Lys Asp Lys Phe Lys Gly Val Thr Lys Ile Gly
                 85                  90                  95

Asp Gly Asp Val Glu Lys Val Ala Lys Glu Lys Pro Asp Leu Ile Ile
            100                 105                 110

Val Tyr Ser Thr Asp Lys Asp Ile Lys Lys Tyr Gln Lys Val Ala Pro
        115                 120                 125

Thr Val Val Asp Tyr Asn Lys His Lys Tyr Leu Glu Gln Gln Glu
130                 135                 140

Met Leu Gly Lys Ile Val Gly Lys Glu Asp Lys Val Lys Ala Trp Lys
145                 150                 155                 160

Lys Asp Trp Glu Glu Thr Thr Ala Lys Asp Gly Lys Glu Ile Lys Lys
                165                 170                 175

Ala Ile Gly Gln Asp Ala Thr Val Ser Leu Phe Asp Glu Phe Asp Lys
            180                 185                 190

Lys Leu Tyr Thr Tyr Gly Asp Asn Trp Gly Arg Gly Gly Glu Val Leu
        195                 200                 205

Tyr Gln Ala Phe Gly Leu Lys Met Gln Pro Glu Gln Gln Lys Leu Thr
210                 215                 220

Ala Lys Ala Gly Trp Ala Glu Val Lys Gln Glu Glu Ile Glu Lys Tyr
225                 230                 235                 240

Ala Gly Asp Tyr Ile Val Ser Thr Ser Glu Gly Lys Pro Thr Pro Gly
                245                 250                 255

Tyr Glu Ser Thr Asn Met Trp Lys Asn Leu Lys Ala Thr Lys Glu Gly
            260                 265                 270

His Ile Val Lys Val Asp Ala Gly Thr Tyr Trp Tyr Asn Asp Pro Tyr
        275                 280                 285

Thr Leu Asp Phe Met Arg Lys Asp Leu Lys Glu Lys Leu Ile Lys Ala
290                 295                 300

Ala Lys Gln Leu Glu Ser Ile Ile Asn Phe Glu Lys Leu Thr Glu Gly
305                 310                 315                 320

Gly Gln Leu Glu Ser Ile Ile Asn Phe Glu Lys Leu Thr Glu Gly Gly
                325                 330                 335

Gln Leu Glu Ser Ile Ile Asn Phe Glu Lys Leu Thr Glu
            340                 345

<210> SEQ ID NO 79
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 79
taattaaagc tgcaaaacag ctggaaagca ttattaactt tgaaaaac                48

<210> SEQ ID NO 80
<211> LENGTH: 50
<212> TYPE: DNA
<213> ORGANISM: Artificial Sequence
<220> FEATURE:
<223> OTHER INFORMATION: oligonucleotide primer

<400> SEQUENCE: 80
tggtgatggt gatgttattc ggtcagtttt tcgaagttga tgatgctttc              50